United States Patent
Seul

(10) Patent No.: US 9,400,259 B2
(45) Date of Patent: Jul. 26, 2016

(54) METHOD OF MAKING A MICROBEAD ARRAY WITH ATTACHED BIOMOLECULES

(71) Applicant: Bioarray Solutions, Ltd, Warren, NJ (US)

(72) Inventor: Michael Seul, Fanwood, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 0 days.

(21) Appl. No.: 14/181,028

(22) Filed: Feb. 14, 2014

(65) Prior Publication Data

US 2014/0262782 A1   Sep. 18, 2014

Related U.S. Application Data

(63) Continuation of application No. 13/664,953, filed on Oct. 31, 2012, now Pat. No. 8,691,594, which is a (Continued)

(51) Int. Cl.
*G01N 33/543* (2006.01)
*G01N 27/447* (2006.01)

(Continued)

(52) U.S. Cl.
CPC ........... *G01N 27/447* (2013.01); *B01J 19/0046* (2013.01); *B01L 3/50273* (2013.01);

(Continued)

(58) Field of Classification Search
CPC ............ B01J 19/0046; B01L 3/50273; B01L 3/502761; B01L 3/502707; C12Q 1/6825; C12Q 1/6837; C40B 40/04; C40B 40/00; G02B 3/0012; G02B 3/0056; G02B 3/0075; G01N 33/54313; G01N 33/54386; G01N 33/6845; G01N 15/1468; H05H 3/04
USPC ........... 436/518, 525, 528, 534, 63, 164, 165, 436/172
See application file for complete search history.

(56) References Cited

U.S. PATENT DOCUMENTS

| 3,329,638 A | 7/1967 | Blyth |
| 3,574,614 A | 4/1971 | Carreira |

(Continued)

FOREIGN PATENT DOCUMENTS

| CA | 1248873 | 1/1989 |
| DE | 4035714 | 5/1992 |

(Continued)

OTHER PUBLICATIONS

Armstrong et al., "Suspension arrays for high throughput, multiplexed single nucleotide polymorphism genotyping" Cytometry. vol. 40:102-108 (2000).

(Continued)

*Primary Examiner* — Mark Shibuya
*Assistant Examiner* — Pensee Do
(74) *Attorney, Agent, or Firm* — Mintz, Levin, Cohn, Ferris, Glovsky and Popeo P.C.

(57) ABSTRACT

A method and apparatus for the manipulation of colloidal particulates and biomolecules at the interface between an insulating electrode such as silicon oxide and an electrolyte solution. Light-controlled electrokinetic assembly of particles near surfaces relics on the combination of three functional elements: the AC electric field-induced assembly of planar aggregates; the patterning of the electrolyte/silicon oxide/silicon interface to exert spatial control over the assembly process; and the real-time control of the assembly process via external illumination. The present invention provides a set of fundamental operations enabling interactive control over the creation and placement of planar arrays of several types of particles and biomolecules and the manipulation of array shape and size. The present invention enables sample preparation and handling for diagnostic assays and biochemical analysis in an array format, and the functional integration of these operations. In addition, the present invention provides a procedure for the creation of material surfaces with desired properties and for the fabrication of surface-mounted optical components.

21 Claims, 13 Drawing Sheets

Related U.S. Application Data continuation of application No. 11/760,814, filed on Jun. 11, 2007, now Pat. No. 8,309,368, which is a continuation of application No. 10/910,466, filed on Aug. 3, 2004, now Pat. No. 7,427,512, which is a continuation of application No. 09/690,040, filed on Oct. 17, 2000, now Pat. No. 6,797,524, which is a continuation of application No. 09/171,550, filed as application No. PCT/US97/08159 on Apr. 24, 1997, now Pat. No. 6,251,691.

(60) Provisional application No. 60/016,642, filed on Apr. 25, 1996.

(51) Int. Cl.
- *B01J 19/00* (2006.01)
- *C12Q 1/68* (2006.01)
- *C40B 40/04* (2006.01)
- *G01N 33/68* (2006.01)
- *G02B 3/00* (2006.01)
- *H05H 3/04* (2006.01)
- *B01L 3/00* (2006.01)
- *C40B 40/00* (2006.01)
- *G01N 15/14* (2006.01)

(52) U.S. Cl.
CPC ......... *B01L3/502761* (2013.01); *C12Q 1/6825* (2013.01); *C12Q 1/6837* (2013.01); *C40B 40/04* (2013.01); *G01N 33/54313* (2013.01); *G01N 33/54386* (2013.01); *G01N 33/6845* (2013.01); *G02B 3/0012* (2013.01); *G02B 3/0056* (2013.01); *G02B 3/0075* (2013.01); *H05H 3/04* (2013.01); *B01J 2219/00585* (2013.01); *B01J 2219/00596* (2013.01); *B01J 2219/00648* (2013.01); *B01J 2219/00653* (2013.01); *B01J 2219/00659* (2013.01); *B01J 2219/00713* (2013.01); *B01L 3/502707* (2013.01); *B01L 2200/0647* (2013.01); *B01L 2200/0652* (2013.01); *B01L 2200/0663* (2013.01); *B01L 2200/0668* (2013.01); *B01L 2300/0636* (2013.01); *B01L 2300/089* (2013.01); *B01L 2300/0816* (2013.01); *B01L 2300/0864* (2013.01); *B01L 2300/0877* (2013.01); *B01L 2400/0415* (2013.01); *B01L 2400/0427* (2013.01); *B01L 2400/0454* (2013.01); *C40B 40/00* (2013.01); *G01N 15/1468* (2013.01); *G01N 2015/149* (2013.01); *G01N 2015/1497* (2013.01); *Y10S 435/808* (2013.01); *Y10S 435/81* (2013.01); *Y10S 435/814* (2013.01); *Y10S 436/806* (2013.01); *Y10S 436/808* (2013.01); *Y10S 436/809* (2013.01); *Y10T 436/25125* (2015.01)

(56) References Cited

U.S. PATENT DOCUMENTS

| | | |
|---|---|---|
| 3,790,492 A | 2/1974 | Fulwyler |
| 3,957,741 A | 5/1976 | Rembaum et al. |
| 3,982,182 A | 9/1976 | Hogg |
| 3,989,775 A | 11/1976 | Jack et al. |
| 3,998,525 A | 12/1976 | Giglia |
| 4,003,713 A | 1/1977 | Bowser |
| 4,046,667 A | 9/1977 | Goetz |
| 4,055,799 A | 10/1977 | Coster et al. |
| 4,075,013 A | 2/1978 | Ward et al. |
| 4,102,990 A | 7/1978 | Uzgiris |
| 4,140,937 A | 2/1979 | Vecht et al. |
| 4,143,203 A | 3/1979 | Rigopulos et al. |
| 4,199,363 A | 4/1980 | Chen |
| 4,258,001 A | 3/1981 | Pierce et al. |
| 4,267,235 A | 5/1981 | Rembaum et al. |
| 4,275,053 A | 6/1981 | Rosenfield et al. |
| 4,326,008 A | 4/1982 | Rembaum |
| 4,336,173 A | 6/1982 | Ugelstad |
| 4,339,337 A | 7/1982 | Tricot et al. |
| 4,358,388 A | 11/1982 | Daniel et al. |
| 4,383,529 A | 5/1983 | Webster |
| 4,421,896 A | 12/1983 | Dorman |
| 4,456,513 A | 6/1984 | Kawai et al. |
| 4,459,378 A | 7/1984 | Ugelstad |
| 4,487,855 A | 12/1984 | Shih et al. |
| 4,497,208 A | 2/1985 | Oja et al. |
| 4,499,052 A | 2/1985 | Fulwyler |
| 4,575,407 A | 3/1986 | Diller |
| 4,591,550 A | 5/1986 | Hafeman et al. |
| 4,602,989 A | 7/1986 | Culkin |
| 4,613,559 A | 9/1986 | Ober et al. |
| 4,647,544 A | 3/1987 | Nicoli et al. |
| 4,654,267 A | 3/1987 | Ugelstad et al. |
| 4,663,408 A | 5/1987 | Schulz et al. |
| 4,665,020 A | 5/1987 | Saunders |
| 4,672,040 A | 6/1987 | Josephson |
| 4,679,439 A | 7/1987 | Culkin |
| 4,680,332 A | 7/1987 | Hair et al. |
| 4,702,598 A | 10/1987 | Böhmer |
| 4,717,655 A | 1/1988 | Fulwyler |
| 4,753,775 A | 6/1988 | Ebersole et al. |
| 4,774,189 A | 9/1988 | Schwartz |
| 4,774,265 A | 9/1988 | Ugelstad et al. |
| 4,791,310 A | 12/1988 | Honig et al. |
| 4,795,698 A | 1/1989 | Owen et al. |
| 4,806,313 A | 2/1989 | Ebersole et al. |
| 4,806,776 A | 2/1989 | Kley |
| 4,822,746 A | 4/1989 | Walt |
| 4,824,941 A | 4/1989 | Gordon et al. |
| 4,829,101 A | 5/1989 | Kraemer et al. |
| 4,832,814 A | 5/1989 | Root |
| 4,851,331 A | 7/1989 | Vary et al. |
| 4,873,102 A | 10/1989 | Chang et al. |
| 4,891,324 A | 1/1990 | Pease et al. |
| 4,911,806 A | 3/1990 | Hofmann |
| 4,920,056 A | 4/1990 | Dasgupta |
| 4,994,373 A | 2/1991 | Stavrianopoulos et al. |
| 4,996,265 A | 2/1991 | Okubo et al. |
| 5,002,867 A | 3/1991 | Macevicz |
| 5,015,452 A | 5/1991 | Matijevic |
| 5,028,545 A | 7/1991 | Soini |
| 5,073,498 A | 12/1991 | Schwartz et al. |
| 5,075,217 A | 12/1991 | Weber |
| 5,091,206 A | 2/1992 | Wang et al. |
| 5,105,305 A | 4/1992 | Betzig et al. |
| 5,114,864 A | 5/1992 | Walt |
| 5,126,239 A | 6/1992 | Livak et al. |
| 5,128,006 A | 7/1992 | Mitchell et al. |
| 5,132,097 A | 7/1992 | Van Deusen et al. |
| 5,132,242 A | 7/1992 | Cheung |
| 5,143,853 A | 9/1992 | Walt |
| 5,143,854 A | 9/1992 | Pirrung et al. |
| 5,147,777 A | 9/1992 | Sutton et al. |
| 5,155,044 A | 10/1992 | Ledis et al. |
| 5,173,159 A | 12/1992 | Dutertre |
| 5,185,066 A | 2/1993 | Golias |
| 5,187,096 A | 2/1993 | Giaever et al. |
| 5,194,300 A | 3/1993 | Cheung |
| 5,194,393 A | 3/1993 | Hugl et al. |
| 5,208,111 A | 5/1993 | Decher et al. |
| 5,221,417 A | 6/1993 | Basavanhally |
| 5,234,809 A | 8/1993 | Boom et al. |
| 5,241,012 A | 8/1993 | Clark |
| 5,244,630 A | 9/1993 | Khalil et al. |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,266,238 A | 11/1993 | Haacke et al. |
| 5,266,427 A | 11/1993 | Iwase et al. |

(56) References Cited

U.S. PATENT DOCUMENTS

| | | |
|---|---|---|
| 5,266,497 A | 11/1993 | Imai et al. |
| 5,281,370 A | 1/1994 | Asher et al. |
| 5,283,079 A | 2/1994 | Wang et al. |
| 5,288,577 A | 2/1994 | Yamaguchi et al. |
| 5,298,741 A | 3/1994 | Walt et al. |
| 5,301,044 A | 4/1994 | Wright |
| 5,306,618 A | 4/1994 | Prober et al. |
| 5,308,586 A | 5/1994 | Fritsche et al. |
| 5,308,749 A | 5/1994 | Sutton et al. |
| 5,320,814 A | 6/1994 | Walt et al. |
| 5,326,691 A | 7/1994 | Hozier |
| 5,326,692 A | 7/1994 | Brinkley et al. |
| 5,329,461 A | 7/1994 | Allen et al. |
| 5,348,853 A | 9/1994 | Wang et al. |
| 5,356,713 A | 10/1994 | Charmot et al. |
| 5,362,653 A | 11/1994 | Carr et al. |
| 5,364,759 A | 11/1994 | Caskey et al. |
| 5,382,512 A | 1/1995 | Smethers et al. |
| 5,382,801 A | 1/1995 | Kanayama |
| 5,389,549 A | 2/1995 | Hamaguchi et al. |
| 5,395,688 A | 3/1995 | Wang et al. |
| 5,405,784 A | 4/1995 | Van Hoegaerden |
| 5,412,087 A | 5/1995 | McGall et al. |
| 5,415,835 A | 5/1995 | Brueck et al. |
| 5,422,246 A | 6/1995 | Koopal et al. |
| 5,436,327 A | 7/1995 | Southern et al. |
| 5,442,246 A | 8/1995 | Azegami et al. |
| 5,444,330 A | 8/1995 | Leventis et al. |
| 5,447,440 A | 9/1995 | Davis et al. |
| 5,468,649 A | 11/1995 | Shah et al. |
| 5,470,534 A | 11/1995 | Imai et al. |
| 5,474,796 A | 12/1995 | Brennan |
| 5,474,895 A | 12/1995 | Ishii et al. |
| 5,480,723 A | 1/1996 | Klainer et al. |
| 5,488,567 A | 1/1996 | Allen et al. |
| 5,496,997 A | 3/1996 | Pope |
| 5,498,392 A | 3/1996 | Wilding et al. |
| 5,510,270 A | 4/1996 | Fodor et al. |
| 5,512,157 A | 4/1996 | Guadagno et al. |
| 5,512,439 A | 4/1996 | Hornes et al. |
| 5,512,490 A | 4/1996 | Walt et al. |
| 5,514,785 A | 5/1996 | VanNess et al. |
| 5,516,635 A | 5/1996 | Ekins et al. |
| 5,518,883 A | 5/1996 | Soini |
| 5,523,231 A | 6/1996 | Reeve |
| 5,527,710 A | 6/1996 | Nacamulli et al. |
| 5,528,392 A | 6/1996 | Nakagawa et al. |
| 5,532,128 A | 7/1996 | Eggers et al. |
| 5,536,648 A | 7/1996 | Kemp et al. |
| 5,545,522 A | 8/1996 | Van Gelder et al. |
| 5,545,531 A | 8/1996 | Rava et al. |
| 5,552,086 A | 9/1996 | Siiman et al. |
| 5,552,270 A | 9/1996 | Khrapko et al. |
| 5,556,752 A | 9/1996 | Lockhart et al. |
| 5,565,324 A | 10/1996 | Still et al. |
| 5,567,304 A | 10/1996 | Datta et al. |
| 5,567,627 A | 10/1996 | Lehnen |
| 5,573,909 A | 11/1996 | Singer et al. |
| 5,582,988 A | 12/1996 | Backus et al. |
| 5,585,069 A | 12/1996 | Zanzucchi et al. |
| 5,587,128 A | 12/1996 | Wilding et al. |
| 5,593,838 A | 1/1997 | Zanzucchi et al. |
| 5,593,839 A | 1/1997 | Hubbell et al. |
| 5,602,042 A | 2/1997 | Farber |
| 5,604,097 A | 2/1997 | Brenner |
| 5,604,099 A | 2/1997 | Erlich et al. |
| 5,610,287 A | 3/1997 | Nikiforov et al. |
| 5,627,040 A | 5/1997 | Bierre et al. |
| 5,632,957 A | 5/1997 | Heller et al. |
| 5,633,724 A | 5/1997 | King et al. |
| 5,633,972 A | 5/1997 | Walt et al. |
| 5,637,508 A | 6/1997 | Kidwell et al. |
| 5,639,603 A | 6/1997 | Dower et al. |
| 5,639,606 A | 6/1997 | Willey |
| 5,643,765 A | 7/1997 | Willey |
| 5,648,124 A | 7/1997 | Sutor |
| 5,650,488 A | 7/1997 | O'Hare |
| 5,650,489 A | 7/1997 | Lam et al. |
| 5,652,059 A | 7/1997 | Margel |
| 5,652,107 A | 7/1997 | Lizardi et al. |
| 5,653,939 A | 8/1997 | Hollis et al. |
| 5,660,990 A | 8/1997 | Rao et al. |
| 5,667,667 A | 9/1997 | Southern |
| 5,674,686 A | 10/1997 | Schumm et al. |
| 5,674,698 A | 10/1997 | Zarling et al. |
| 5,679,524 A | 10/1997 | Nikiforov et al. |
| 5,690,894 A | 11/1997 | Pinkel et al. |
| 5,698,271 A | 12/1997 | Liberti et al. |
| 5,700,637 A | 12/1997 | Southern |
| 5,700,897 A | 12/1997 | Klainer et al. |
| 5,714,340 A | 2/1998 | Sutton et al. |
| 5,714,521 A | 2/1998 | Kedem et al. |
| 5,716,852 A | 2/1998 | Yager et al. |
| 5,722,470 A | 3/1998 | Kedar et al. |
| 5,723,218 A | 3/1998 | Haugland et al. |
| 5,723,233 A | 3/1998 | Garza et al. |
| 5,728,529 A | 3/1998 | Metzker et al. |
| 5,736,349 A | 4/1998 | Sasaki et al. |
| 5,744,299 A | 4/1998 | Henrickson et al. |
| 5,744,305 A | 4/1998 | Fodor et al. |
| 5,747,349 A | 5/1998 | van den Engh et al. |
| 5,751,629 A | 5/1998 | Nova et al. |
| 5,763,175 A | 6/1998 | Brenner |
| 5,763,198 A | 6/1998 | Hirth et al. |
| 5,763,263 A | 6/1998 | Dehlinger |
| 5,766,711 A | 6/1998 | Barmakian |
| 5,766,963 A | 6/1998 | Baldwin et al. |
| 5,770,358 A | 6/1998 | Dower et al. |
| 5,770,367 A | 6/1998 | Southern et al. |
| 5,770,455 A | 6/1998 | Cargill et al. |
| 5,770,721 A | 6/1998 | Ershov et al. |
| 5,773,222 A | 6/1998 | Scott |
| 5,776,711 A | 7/1998 | Vyas et al. |
| 5,779,976 A | 7/1998 | Leland et al. |
| 5,786,219 A | 7/1998 | Zhang et al. |
| 5,789,147 A | 8/1998 | Rubinstein et al. |
| 5,792,430 A | 8/1998 | Hamper |
| 5,800,992 A | 9/1998 | Fodor et al. |
| 5,807,755 A | 9/1998 | Ekins |
| 5,812,272 A | 9/1998 | King et al. |
| 5,814,524 A | 9/1998 | Walt et al. |
| 5,831,045 A | 11/1998 | Stolowitz et al. |
| 5,834,590 A | 11/1998 | Vinik et al. |
| 5,837,501 A | 11/1998 | Beumer et al. |
| 5,837,551 A | 11/1998 | Ekins |
| 5,837,832 A | 11/1998 | Chee et al. |
| 5,840,485 A | 11/1998 | Lebl et al. |
| 5,843,660 A | 12/1998 | Schumm et al. |
| 5,844,304 A | 12/1998 | Kata et al. |
| 5,846,708 A | 12/1998 | Hollis et al. |
| 5,855,753 A | 1/1999 | Trau et al. |
| 5,856,092 A | 1/1999 | Dale et al. |
| 5,858,804 A | 1/1999 | Zanzucchi et al. |
| 5,866,099 A | 2/1999 | Owen et al. |
| 5,866,331 A | 2/1999 | Singer et al. |
| 5,874,219 A | 2/1999 | Rava et al. |
| 5,876,946 A | 3/1999 | Burbaum et al. |
| 5,898,071 A | 4/1999 | Hawkins |
| 5,900,481 A | 5/1999 | Lough et al. |
| 5,922,617 A | 7/1999 | Wang et al. |
| 5,939,021 A | 8/1999 | Hansen et al. |
| 5,942,388 A | 8/1999 | Willner et al. |
| 5,945,525 A | 8/1999 | Uematsu et al. |
| 5,948,621 A | 9/1999 | Turner et al. |
| 5,948,627 A | 9/1999 | Lee et al. |
| 5,952,131 A | 9/1999 | Kumacheva et al. |
| 5,952,174 A | 9/1999 | Nikiforoy et al. |
| 5,959,098 A | 9/1999 | Goldberg et al. |
| 5,961,923 A | 10/1999 | Nova et al. |
| 5,965,235 A | 10/1999 | McGuire et al. |
| 5,965,452 A | 10/1999 | Kovacs |
| 5,968,736 A | 10/1999 | Still et al. |
| 5,981,176 A | 11/1999 | Wallace |
| 5,981,180 A | 11/1999 | Chandler et al. |

(56) References Cited

U.S. PATENT DOCUMENTS

| | | |
|---|---|---|
| 5,988,432 A | 11/1999 | Sun |
| 5,989,835 A | 11/1999 | Dunlay et al. |
| 5,993,935 A | 11/1999 | Rasmussen et al. |
| 5,994,066 A | 11/1999 | Bergeron et al. |
| 6,001,614 A | 12/1999 | Akhavan-Tafti |
| 6,004,744 A | 12/1999 | Goelet et al. |
| 6,007,996 A | 12/1999 | McNamara et al. |
| 6,013,531 A | 1/2000 | Wang et al. |
| 6,014,451 A | 1/2000 | Berry et al. |
| 6,015,664 A | 1/2000 | Henrickson et al. |
| 6,015,666 A | 1/2000 | Springer et al. |
| 6,017,696 A | 1/2000 | Heller |
| 6,018,350 A | 1/2000 | Lee et al. |
| 6,023,540 A | 2/2000 | Walt et al. |
| 6,023,590 A | 2/2000 | Abe et al. |
| 6,025,905 A | 2/2000 | Sussman |
| 6,027,889 A | 2/2000 | Barany et al. |
| 6,027,945 A | 2/2000 | Smith et al. |
| 6,033,547 A | 3/2000 | Trau et al. |
| 6,043,354 A | 3/2000 | Hillebrand et al. |
| 6,048,690 A | 4/2000 | Heller |
| 6,054,270 A | 4/2000 | Southern |
| 6,060,243 A | 5/2000 | Tang et al. |
| 6,063,569 A | 5/2000 | Gildea et al. |
| 6,068,818 A | 5/2000 | Ackley et al. |
| 6,075,905 A | 6/2000 | Herman et al. |
| 6,077,669 A | 6/2000 | Little et al. |
| 6,077,674 A | 6/2000 | Schleifer et al. |
| 6,080,585 A | 6/2000 | Southern et al. |
| 6,083,699 A | 7/2000 | Leushner et al. |
| 6,083,763 A | 7/2000 | Balch |
| 6,084,991 A | 7/2000 | Sampas |
| 6,086,736 A | 7/2000 | Dasgupta et al. |
| 6,090,458 A | 7/2000 | Murakami |
| 6,090,545 A | 7/2000 | Wohlstadter et al. |
| 6,090,555 A | 7/2000 | Fiekowsky et al. |
| 6,090,912 A | 7/2000 | Lebl et al. |
| 6,096,368 A | 8/2000 | Sun |
| 6,100,030 A | 8/2000 | Feazel et al. |
| 6,103,379 A | 8/2000 | Margel et al. |
| 6,106,685 A | 8/2000 | McBride et al. |
| 6,120,666 A | 9/2000 | Jacobson et al. |
| 6,122,599 A | 9/2000 | Mehta |
| 6,123,263 A | 9/2000 | Feng |
| 6,124,092 A | 9/2000 | O'Neill et al. |
| 6,126,731 A | 10/2000 | Kemeny et al. |
| 6,130,101 A | 10/2000 | Mao et al. |
| 6,132,685 A | 10/2000 | Kercso et al. |
| 6,132,997 A | 10/2000 | Shannon |
| 6,133,436 A | 10/2000 | Koster et al. |
| 6,136,171 A | 10/2000 | Frazier et al. |
| 6,136,468 A | 10/2000 | Mitchell, Jr. et al. |
| 6,139,831 A | 10/2000 | Shivashankar et al. |
| 6,141,046 A | 10/2000 | Roth et al. |
| 6,143,499 A | 11/2000 | Mirzabekov et al. |
| 6,149,789 A | 11/2000 | Benecke et al. |
| 6,150,095 A | 11/2000 | Southern et al. |
| 6,151,062 A | 11/2000 | Inoguchi et al. |
| 6,153,375 A | 11/2000 | Kobylecki et al. |
| 6,153,389 A | 11/2000 | Haarer et al. |
| 6,156,502 A | 12/2000 | Beattie |
| 6,167,910 B1 | 1/2001 | Chow |
| 6,172,218 B1 | 1/2001 | Brenner |
| 6,180,226 B1 | 1/2001 | McArdle et al. |
| 6,183,970 B1 | 2/2001 | Okano et al. |
| 6,187,540 B1 | 2/2001 | Staub et al. |
| 6,193,866 B1 | 2/2001 | Bader et al. |
| 6,193,951 B1 | 2/2001 | Ottoboni et al. |
| 6,200,737 B1 | 3/2001 | Walt et al. |
| 6,200,814 B1 | 3/2001 | Malmqvist et al. |
| 6,203,993 B1 | 3/2001 | Shuber et al. |
| 6,207,369 B1 | 3/2001 | Wohlstadter et al. |
| 6,209,589 B1 | 4/2001 | Hare et al. |
| 6,218,111 B1 | 4/2001 | Southern et al. |
| 6,221,598 B1 | 4/2001 | Schumm et al. |
| 6,232,066 B1 | 5/2001 | Felder et al. |
| 6,235,471 B1 | 5/2001 | Knapp et al. |
| 6,238,863 B1 | 5/2001 | Schumm et al. |
| 6,245,508 B1 | 6/2001 | Heller et al. |
| 6,251,592 B1 | 6/2001 | Tang et al. |
| 6,251,595 B1 | 6/2001 | Gordon et al. |
| 6,251,687 B1 | 6/2001 | Buechler et al. |
| 6,251,691 B1 | 6/2001 | Seul |
| 6,254,754 B1 | 7/2001 | Ross et al. |
| 6,254,827 B1 | 7/2001 | Ackley et al. |
| 6,261,430 B1 | 7/2001 | Yager et al. |
| 6,261,782 B1 | 7/2001 | Lizardi et al. |
| 6,264,815 B1 | 7/2001 | Pethig et al. |
| 6,264,825 B1 | 7/2001 | Blackburn et al. |
| 6,266,459 B1 | 7/2001 | Walt et al. |
| 6,267,858 B1 | 7/2001 | Parce et al. |
| 6,268,219 B1 | 7/2001 | Mcbride et al. |
| 6,268,222 B1 | 7/2001 | Chandler et al. |
| 6,271,856 B1 | 8/2001 | Krishnamurthy |
| 6,277,579 B1 | 8/2001 | Lazar et al. |
| 6,280,618 B2 | 8/2001 | Watkins et al. |
| 6,287,778 B1 | 9/2001 | Huang et al. |
| 6,294,063 B1 | 9/2001 | Becker et al. |
| 6,297,062 B1 | 10/2001 | Gombinski |
| 6,303,316 B1 | 10/2001 | Kiel et al. |
| 6,306,643 B1 | 10/2001 | Gentalen et al. |
| 6,307,039 B1 | 10/2001 | Southern et al. |
| 6,309,602 B1 | 10/2001 | Ackley et al. |
| 6,312,134 B1 | 11/2001 | Jain et al. |
| 6,316,186 B1 | 11/2001 | Ekins |
| 6,318,970 B1 | 11/2001 | Backhouse |
| 6,319,472 B1 | 11/2001 | Ackley et al. |
| 6,319,674 B1 | 11/2001 | Fulcrand et al. |
| 6,321,791 B1 | 11/2001 | Chow |
| 6,327,410 B1 | 12/2001 | Walt et al. |
| 6,342,355 B1 | 1/2002 | Hacia et al. |
| 6,349,144 B1 | 2/2002 | Shams |
| 6,355,419 B1 | 3/2002 | Alfenito |
| 6,355,431 B1 | 3/2002 | Chee et al. |
| 6,355,491 B1 | 3/2002 | Zhou et al. |
| 6,358,387 B1 | 3/2002 | Kopf-Sill et al. |
| 6,361,916 B1 | 3/2002 | Chen et al. |
| 6,361,945 B1 | 3/2002 | Becker et al. |
| 6,365,418 B1 | 4/2002 | Wagner et al. |
| 6,368,799 B1 | 4/2002 | Chee |
| 6,387,707 B1 | 5/2002 | Seul et al. |
| 6,399,328 B1 | 6/2002 | Vournakis et al. |
| 6,403,309 B1 | 6/2002 | Iris et al. |
| 6,406,921 B1 | 6/2002 | Wagner et al. |
| 6,426,615 B1 | 7/2002 | Mehta |
| 6,429,027 B1 | 8/2002 | Chee et al. |
| 6,448,012 B1 | 9/2002 | Schwartz |
| 6,451,191 B1 | 9/2002 | Bentsen et al. |
| 6,458,547 B1 | 10/2002 | Bryan et al. |
| 6,468,811 B1 | 10/2002 | Seul |
| 6,480,791 B1 | 11/2002 | Strathmann |
| 6,488,872 B1 | 12/2002 | Beebe et al. |
| 6,494,924 B1 | 12/2002 | Auweter et al. |
| 6,498,863 B1 | 12/2002 | Gaidoukevitch et al. |
| 6,500,620 B2 | 12/2002 | Yu et al. |
| 6,503,680 B1 | 1/2003 | Chen et al. |
| 6,506,564 B1 | 1/2003 | Mirkin et al. |
| 6,509,158 B1 | 1/2003 | Schwartz |
| 6,514,688 B2 | 2/2003 | Muller-Schulte |
| 6,514,714 B1 | 2/2003 | Lee et al. |
| 6,514,771 B1 | 2/2003 | Seul |
| 6,515,649 B1 | 2/2003 | Albert et al. |
| 6,521,747 B2 | 2/2003 | Anastasio et al. |
| 6,528,264 B1 | 3/2003 | Pal et al. |
| 6,531,292 B1 | 3/2003 | Rine et al. |
| 6,531,323 B1 | 3/2003 | Shinoki et al. |
| 6,534,274 B2 | 3/2003 | Becker et al. |
| 6,534,293 B1 | 3/2003 | Barany et al. |
| 6,540,895 B1 | 4/2003 | Spence et al. |
| 6,605,453 B2 | 8/2003 | Ozkan et al. |
| 6,605,474 B1 | 8/2003 | Cole |
| 6,610,256 B2 | 8/2003 | Schwartz |
| 6,620,584 B1 | 9/2003 | Chee et al. |
| 6,642,062 B2 | 11/2003 | Kauver et al. |

(56) References Cited

U.S. PATENT DOCUMENTS

| | | |
|---|---|---|
| 6,645,432 B1 | 11/2003 | Anderson et al. |
| 6,650,703 B1 | 11/2003 | Schwarzmann et al. |
| 6,670,128 B2 | 12/2003 | Smith et al. |
| 6,692,914 B1 | 2/2004 | Klaerner et al. |
| 6,703,288 B2 | 3/2004 | Nagasawa et al. |
| 6,706,163 B2 | 3/2004 | Seul et al. |
| 6,713,309 B1 | 3/2004 | Anderson et al. |
| 6,730,515 B2 | 5/2004 | Kocher |
| 6,743,581 B1 | 6/2004 | Vo-Dinh |
| 6,760,157 B1 | 7/2004 | Allen et al. |
| 6,779,559 B2 | 8/2004 | Parce et al. |
| 6,797,524 B1 | 9/2004 | Seul |
| 6,806,050 B2 | 10/2004 | Zhou et al. |
| 6,812,005 B2 | 11/2004 | Fan et al. |
| 6,838,289 B2 | 1/2005 | Bell et al. |
| 6,844,156 B2 | 1/2005 | Rosen |
| 6,869,798 B2 | 3/2005 | Crews et al. |
| 6,887,701 B2 | 5/2005 | Anderson et al. |
| 6,890,741 B2 | 5/2005 | Fan et al. |
| 6,897,271 B1 | 5/2005 | Domschke et al. |
| 6,905,881 B2 | 6/2005 | Sammak et al. |
| 6,908,737 B2 | 6/2005 | Ravkin et al. |
| 6,942,968 B1 | 9/2005 | Dickinson et al. |
| 6,955,751 B1 | 10/2005 | Seul |
| 6,955,889 B1 | 10/2005 | Mercolino et al. |
| 6,955,902 B2 | 10/2005 | Chumakov et al. |
| 6,958,245 B2 | 10/2005 | Seul et al. |
| 6,991,941 B1 | 1/2006 | Seul |
| 6,993,156 B1 | 1/2006 | Szeliski et al. |
| 7,015,047 B2 | 3/2006 | Huang et al. |
| 7,041,453 B2 | 5/2006 | Yang |
| 7,049,077 B2 | 5/2006 | Yang |
| 7,056,746 B2 | 6/2006 | Seul et al. |
| 7,060,431 B2 | 6/2006 | Chee et al. |
| 7,090,759 B1 | 8/2006 | Seul |
| 7,097,974 B1 | 8/2006 | Stahler et al. |
| 7,099,777 B1 | 8/2006 | Ghandour |
| 7,115,884 B1 | 10/2006 | Walt et al. |
| 7,132,239 B2 | 11/2006 | Livak et al. |
| 7,141,217 B2 | 11/2006 | Karlsson et al. |
| 7,144,119 B2 | 12/2006 | Seul et al. |
| 7,157,228 B2 | 1/2007 | Hashmi et al. |
| 7,195,913 B2 | 3/2007 | Guire et al. |
| 7,229,840 B1 | 6/2007 | Wischerhoff |
| 7,262,016 B2 | 8/2007 | Huang et al. |
| 7,291,504 B2 | 11/2007 | Seul |
| 7,306,918 B2 | 12/2007 | Hashmi et al. |
| 7,320,864 B2 | 1/2008 | Yang |
| 7,335,153 B2 | 2/2008 | Seul et al. |
| 7,344,841 B2 | 3/2008 | Hashmi et al. |
| 7,358,097 B2 | 4/2008 | Seul et al. |
| 7,390,676 B2 | 6/2008 | Seul et al. |
| 7,425,416 B2 | 9/2008 | Hashmi et al. |
| 7,427,512 B2 | 9/2008 | Seul |
| 7,501,253 B2 | 3/2009 | Pourmand et al. |
| 7,526,114 B2 | 4/2009 | Xia et al. |
| 7,582,488 B2 | 9/2009 | Banerjee et al. |
| 7,595,279 B2 | 9/2009 | Wang et al. |
| 7,615,345 B2 | 11/2009 | Seul |
| 7,732,575 B2 | 6/2010 | Wang et al. |
| 7,737,088 B1 | 6/2010 | Stahler et al. |
| 7,749,774 B2 | 7/2010 | Seul |
| 7,790,380 B2 | 9/2010 | Yang |
| 7,848,889 B2 | 12/2010 | Xia et al. |
| 7,940,968 B2 | 5/2011 | Seul et al. |
| 2001/0034614 A1 | 10/2001 | Fletcher-Haynes et al. |
| 2001/0044531 A1 | 11/2001 | McGall et al. |
| 2001/0046602 A1 | 11/2001 | Chandler et al. |
| 2001/0049095 A1 | 12/2001 | Webster |
| 2002/0006634 A1 | 1/2002 | Han et al. |
| 2002/0015952 A1 | 2/2002 | Anderson et al. |
| 2002/0022276 A1 | 2/2002 | Zhou et al. |
| 2002/0029235 A1 | 3/2002 | Lock et al. |
| 2002/0031841 A1 | 3/2002 | Asher et al. |
| 2002/0032252 A1 | 3/2002 | Ishizuka |
| 2002/0039728 A1 | 4/2002 | Kain et al. |
| 2002/0045169 A1 | 4/2002 | Shoemaker et al. |
| 2002/0081714 A1 | 6/2002 | Jain et al. |
| 2002/0102567 A1 | 8/2002 | Fodor et al. |
| 2002/0125138 A1 | 9/2002 | Medoro |
| 2002/0127603 A1 | 9/2002 | Basiji et al. |
| 2002/0137074 A1 | 9/2002 | Piunno et al. |
| 2002/0142318 A1 | 10/2002 | Cattell et al. |
| 2002/0150909 A1 | 10/2002 | Stuelpnagel et al. |
| 2002/0155481 A1 | 10/2002 | Hirota et al. |
| 2002/0166766 A1 | 11/2002 | Seul et al. |
| 2002/0182609 A1 | 12/2002 | Arcot |
| 2002/0187501 A1 | 12/2002 | Huang et al. |
| 2002/0197728 A1 | 12/2002 | Kaufman et al. |
| 2002/0198665 A1 | 12/2002 | Seul et al. |
| 2003/0003272 A1 | 1/2003 | Laguitton |
| 2003/0004594 A1 | 1/2003 | Liu et al. |
| 2003/0006143 A1 | 1/2003 | Banerjee et al. |
| 2003/0012693 A1 | 1/2003 | Otillar et al. |
| 2003/0012699 A1 | 1/2003 | Moore et al. |
| 2003/0022370 A1 | 1/2003 | Casagrande et al. |
| 2003/0022393 A1 | 1/2003 | Seul et al. |
| 2003/0031351 A1 | 2/2003 | Yim |
| 2003/0038812 A1 | 2/2003 | Bartell |
| 2003/0040129 A1 | 2/2003 | Shah |
| 2003/0062422 A1 | 4/2003 | Fateley et al. |
| 2003/0077607 A1 | 4/2003 | Hopfinger et al. |
| 2003/0082487 A1 | 5/2003 | Burgess |
| 2003/0082530 A1 | 5/2003 | Soderlund et al. |
| 2003/0082531 A1 | 5/2003 | Soderlund et al. |
| 2003/0082587 A1 | 5/2003 | Seul et al. |
| 2003/0087228 A1 | 5/2003 | Bamdad et al. |
| 2003/0108913 A1 | 6/2003 | Schouten |
| 2003/0129296 A1 | 7/2003 | Kelso |
| 2003/0134326 A1 | 7/2003 | Hansen et al. |
| 2003/0138842 A1 | 7/2003 | Seul et al. |
| 2003/0148335 A1 | 8/2003 | Shen et al. |
| 2003/0152931 A1 | 8/2003 | Chiou et al. |
| 2003/0154108 A1 | 8/2003 | Fletcher-Haynes et al. |
| 2003/0177036 A1 | 9/2003 | Oka et al. |
| 2003/0182068 A1 | 9/2003 | Battersby et al. |
| 2003/0186220 A1 | 10/2003 | Zhou et al. |
| 2003/0228610 A1 | 12/2003 | Seul |
| 2004/0002073 A1 | 1/2004 | Li et al. |
| 2004/0009614 A1 | 1/2004 | Ahn et al. |
| 2004/0014073 A1 | 1/2004 | Trau et al. |
| 2004/0048259 A1 | 3/2004 | Hashmi et al. |
| 2004/0093238 A1 | 5/2004 | Deakter |
| 2004/0106121 A1 | 6/2004 | Ugolin et al. |
| 2004/0132122 A1 | 7/2004 | Banerjee et al. |
| 2004/0137641 A1 | 7/2004 | Holtlund et al. |
| 2004/0175734 A1 | 9/2004 | Stahler et al. |
| 2004/0219520 A1 | 11/2004 | Mirkin et al. |
| 2004/0229269 A1 | 11/2004 | Hashmi et al. |
| 2005/0048570 A1 | 3/2005 | Weber et al. |
| 2005/0112585 A1 | 5/2005 | Zichi et al. |
| 2005/0143928 A1 | 6/2005 | Moser et al. |
| 2005/0239098 A1 | 10/2005 | Hastings et al. |
| 2006/0024732 A1 | 2/2006 | Huang et al. |
| 2006/0035240 A1 | 2/2006 | Seul et al. |
| 2006/0275799 A1 | 12/2006 | Banerjee et al. |
| 2007/0031877 A1 | 2/2007 | Stahler et al. |
| 2007/0231810 A1 | 10/2007 | Todd et al. |
| 2007/0243534 A1 | 10/2007 | Seul et al. |
| 2008/0020374 A1 | 1/2008 | Greene et al. |
| 2008/0123089 A1 | 5/2008 | Seul et al. |
| 2008/0200349 A1 | 8/2008 | Wu et al. |
| 2008/0214412 A1 | 9/2008 | Stahler et al. |
| 2008/0261205 A1 | 10/2008 | Denomme |
| 2010/0062518 A1 | 3/2010 | Banerjee |

FOREIGN PATENT DOCUMENTS

| | | |
|---|---|---|
| EP | 0126450 | 11/1984 |
| EP | 179039 | 4/1986 |
| EP | 246864 | 11/1987 |
| EP | 269764 | 6/1988 |
| EP | 472990 | 3/1992 |
| EP | 478319 | 4/1992 |

(56) References Cited

FOREIGN PATENT DOCUMENTS

| | | |
|---|---|---|
| EP | 0529775 | 3/1993 |
| EP | 1394270 | 3/2004 |
| EP | 1564306 | 2/2005 |
| JP | 62265567 | 11/1987 |
| JP | 03-236777 | 10/1991 |
| WO | WO8911101 | 5/1989 |
| WO | WO 9109141 | 6/1991 |
| WO | WO 9119023 | 12/1991 |
| WO | WO 9210092 | 6/1992 |
| WO | WO 9302360 | 2/1993 |
| WO | WO 9306121 | 4/1993 |
| WO | WO 9324517 | 12/1993 |
| WO | WO 9325563 | 12/1993 |
| WO | WO 9400810 | 1/1994 |
| WO | WO 9428028 | 9/1994 |
| WO | WO 9509248 | 4/1995 |
| WO | WO 9512608 | 5/1995 |
| WO | WO 9512808 | 5/1995 |
| WO | WO 9600148 | 1/1996 |
| WO | WO 9602558 | 2/1996 |
| WO | WO 9603212 | 2/1996 |
| WO | WO 9604547 | 2/1996 |
| WO | WO 9607917 | 3/1996 |
| WO | WO 9630392 | 10/1996 |
| WO | WO9641011 | 12/1996 |
| WO | WO 9714028 | 4/1997 |
| WO | WO 9722720 | 6/1997 |
| WO | WO 9739151 | 10/1997 |
| WO | WO 9740383 | 10/1997 |
| WO | WO 9740385 | 10/1997 |
| WO | WO 9745559 | 12/1997 |
| WO | WO 9802752 | 1/1998 |
| WO | WO 9804950 | 2/1998 |
| WO | WO 9806007 | 2/1998 |
| WO | WO 9820153 | 5/1998 |
| WO | WO 9821593 | 5/1998 |
| WO | WO 9838334 | 9/1998 |
| WO | WO 9840726 | 9/1998 |
| WO | WO 9853093 | 11/1998 |
| WO | WO 9909217 | 2/1999 |
| WO | WO 9918434 | 4/1999 |
| WO | WO 9919515 | 4/1999 |
| WO | WO 9924822 | 5/1999 |
| WO | WO 9935499 | 7/1999 |
| WO | WO 9936564 | 7/1999 |
| WO | WO 9941273 | 8/1999 |
| WO | WO 9951773 | 10/1999 |
| WO | WO 9960170 | 11/1999 |
| WO | WO 9967641 | 12/1999 |
| WO | WO 0003004 | 1/2000 |
| WO | WO 0004372 | 1/2000 |
| WO | WO 0007019 | 2/2000 |
| WO | WO 0013004 | 3/2000 |
| WO | WO 0020593 | 4/2000 |
| WO | WO 0022172 | 4/2000 |
| WO | WO 0026920 | 5/2000 |
| WO | WO 0031356 | 6/2000 |
| WO | WO 0039587 | 7/2000 |
| WO | WO 0046602 | 8/2000 |
| WO | WO 0051058 | 8/2000 |
| WO | WO 0062048 | 10/2000 |
| WO | WO 0073777 | 12/2000 |
| WO | WO 0075373 | 12/2000 |
| WO | WO 0101184 | 1/2001 |
| WO | WO 0120179 | 3/2001 |
| WO | WO 0136679 | 5/2001 |
| WO | WO 0154813 | 8/2001 |
| WO | WO 0156216 | 8/2001 |
| WO | WO 0184150 | 11/2001 |
| WO | WO 0188535 | 11/2001 |
| WO | WO 0194947 | 12/2001 |
| WO | WO 0198765 | 12/2001 |
| WO | WO 0212888 | 2/2002 |
| WO | WO 0214864 | 2/2002 |
| WO | WO 0231182 | 4/2002 |
| WO | WO 0233084 | 4/2002 |
| WO | WO 0235441 | 5/2002 |
| WO | WO 0237209 | 5/2002 |
| WO | WO02057496 | 7/2002 |
| WO | WO02058379 | 7/2002 |
| WO | WO02061121 | 8/2002 |
| WO | WO 02079490 | 10/2002 |
| WO | WO 02084285 | 10/2002 |
| WO | WO 02096979 | 12/2002 |
| WO | WO 03020968 | 3/2003 |
| WO | WO 03025011 | 3/2003 |
| WO | WO 03034029 | 4/2003 |
| WO | WO 03058196 | 7/2003 |
| WO | WO 03079401 | 9/2003 |
| WO | WO 03092546 | 11/2003 |
| WO | WO 2004035426 | 4/2004 |
| WO | WO 2005000236 | 1/2005 |
| WO | WO 2005042763 | 5/2005 |
| WO | WO 2005045059 | 5/2005 |
| WO | WO 2005095650 | 10/2005 |
| WO | WO 2008040257 | 4/2008 |
| WO | WO 2009088893 | 7/2009 |
| WO | WO 2010025002 | 3/2010 |
| WO | WO2010026038 | 3/2010 |
| WO | WO2010098765 | 9/2010 |
| WO | WO 2010143678 | 12/2010 |

OTHER PUBLICATIONS

Bortolin, S. et al. "Analytical validation of the tag-it high-throughput microsphere-based universal arrray genotyping platform: application to the multiplex detection of a panel of thrombophilia-associated single-nucleotide polymorphisms" Clinical Chemistry, vol. 50 (11), pp. 2028-2036 (Sep. 13, 2004).

B. -Y. HA et al., "Counterion-Mediated Attraction between Two Like-Charged Rods," Physical Review Letters, Aug. 18, 1997, vol. 79, No. 7, pp. 1289-1292.

A. Hatch, et al., "Diffusion Immunoassay in Polyacrylamide Hydrogels". Micro Total Analysis Systems, pp. 571-572 (2001).

Aho et al., "Efficient String Matching: An Aid to Bibliographic Search". Communications of the ACM, vol. 18, No. 6, pp. 333-340 (Jun. 1975).

Albergo et al., "Solvent effects on the thermodynamics of double-helix formation in (dG-sC) 3". Biochemistry, vol. 20, No. 6: 1413-1418 (1981).

Albrecht et al, "Probing the role of multicellular organization in three-dimensional microenvironments". Nature Methods, vol. 3, No. 5, pp. 369-375 (May 2006).

Albrecht et al., "Photo and electropatterning of hydrogel-encapsulated living cell arrays", Lab on a Chip, vol. 5, Issue 1, pp. 111-118 (2004).

Alford, R. L., "DNA Analysis in forensics, disease and animal/plant identification". Current Opinions in Biotechnology, vol. 5(1), pp. 29-33 (1994).

Al-Soud, W. A., "Purification and Characterization of PCR-Inhibitory Components in Blood Cells". Journal of Clinical Microbiology, vol. 39, No. 2, pp. 485-493 (Feb. 2001).

Al-Soud, W. A., et al., "Identification and characterization of immunoglobulin G in blood as a major inhibitor of diagnostic PCR". Journal of Clinical Microbiology, vol. 38, No. 1, pp. 345-350 (Jan. 2000).

Ambruso, D. R., et al., "Experience with donors matched for minor blood group antigens in patients with sickle cell anemia who are receiving chronic transfusion therapy", Transfusion, vol. 27, No. 1, 1987, pp. 94-98.

Zhang, Y., et al., "Reproducible and inexpensive probe preparation for oligonucleotide arrays". Nucleic Acids Research, vol. 29, No. 13, pp. E66-E6 (Jul. 1, 2001).

Arenko, et al., "Protein microchips: Use for immunoassay and enzymatic reactions". Analytical Biochemistry, vol. 278, pp. 123-131 (2000).

Assie et al., Correlation between low/high affinity ratios for 5-HT Receptors and Intrinsic Activity, European Journal of Pharmacology, vol. 386, pp. 97-103 (1999).

(56) References Cited

OTHER PUBLICATIONS

Bakewell et al., "Characterization of the dielectrophoretic movement of DNA in micro-fabricated structures", Institute of Physics Conference Series (1999) Electrostatics (1999).
Balass et al. "Recovery of high-affinity phage from a Nitrostretavidin matrix in phage-display technology". Analytical Biochemistry. vol. 243: 264-269 (1996).
Baldwin, et al., "Phosphorylation of gastrin-17 by epidermal growth factor-stimulated tyrosine kinase". Nature, vol. 44, pp. 2403-2404 (1998).
Bandeira-Melo, C., et al., "EliCell: A gel-phase dual antibody capture and detection assay to measure cytokine release from eosinophils". Journal of Immunological Methods, vol. 244, pp. 105-115 (2000).
Bao, Y. P., et al., "Detection of Protein Analytes via Nanoparticle-Based Bio Bar Code Technology". Anal. Chem., vol. 78, pp. 2055-2059 (2006).
Barany, Francis, "Genetic Disease Detection and DNA Amplification using Cloned Thermostable Ligase". Proceedings of the National Academy of Sciences of the United States of America, vol. 88, pp. 189-193 (Jan. 1991).
Barnard et al. "A fibre-optic chemical sensor with descrete sensing sites". Nature, vol. 353:338-340 (1991).
Basu, S., et al., "Synthesis and Characterization of a Peptide Nucleic Acid Conjugated to a D-Peptide Analog of Insulin-like Growth Factor 1 for Increased Cellular Uptake". Bioconjugate Chem, vol. 8, No. 4, pp. 481-488 (1997).
Battersby et al., "Toward Larger Chemical Libraries: Encoding with Fluorescent Colloids in Combinatorial Chemistry". J. Amer Chem Soc, vol. 122, pp. 2138-2139 (2000).
Baumgarth N. et al., A practical approach to multicolor flow cytometry for immunophenotyping, J. Immunological Methods, 2000, pp. 77-97, vol. 243.
Bavykin, S.G., et al., "Portable system for microbial sample preparation and oligonucleotide microarray analysis". Appl. Environmental Microbiol. 67(2), 922-928 (2001).
Beatty et al. "Probability of Finding HLA-mismatched Related or Unrelated Marrow or Cord Blood Donors", Human Immunology, 2001, vol. 61, pp. 834-840.
Beebe et al., "Functional Hydrogel structures for autonomous flow control inside microfluidic channels". Nature, vol. 404, No. 6778, pp. 588-590 (Apr. 6, 2000).
Beiboer, S. W., et al., "Rapid genotyping of blood group antigens by multiplex polymerase chain reaction and DNA microarray hybridization" 45 Transfusion 667-679 (2005).
Bennett, P. R., et al., "Prenatal Determination of Fetal RhD Type by DNA Amplification". The New England Journal of Medicine, vol. 329, No. 9, pp. 607-610 (Aug. 26, 1993).
Bernard, Philip S., "Homogenous Multiplex Genotyping of Hemochromatasis Mutations with Fluorescent Hybridization Probes". American Journal of Pthology, vol. 153, No. 4, pp. 1055-1061 (1998).
Bessetti, J., "An introduction to PCT Inhibitors". Profiles in DNA-PCR Inhibition, pp. 9-10 (Mar. 2007).
Bickel, P. J., "Discussion of The Evaluation of Forensic DNA Evidence". Proc. Natl. Acad. Sci., vol. 94, p. 5497 (May 1997).
Zhang, X., et al., "Strand invasion by mixed base PNAs and a PNA-peptide chimera". Nucleic Acids Research, vol. 28, No. 17, pp. 3332-3338 (2000).
Blaaderen, et al., "Synthesis and Characterization of Colloidal Dispersions of Fluorescent, Monodisperse Silica Spheres". Langmuir, vol. 8, No. 2, pp. 2921-2931 (1992).
Bonnet, G., et al., "Thermodynamic basis of the enhanced specificity of structured DNA probes," Proc. Natl. Acad. Science, USA, vol. 96, pp. 6171-6176, May 1999.
Bos et al., "Controlled release of pharmaceutical protein from hydrogels". Business Briefing: Pharmatech, pp. 184-187 (2002).
Boyce, et al. "Peptidosteroidal Receptors for Opioid Peptides. Sequence-Selective Binding Using a Synthetic Receptor Library". J. Am. Chem. Soc., vol. 116, No. 17, pp. 7955-7956 (1994).

Boyd et al., "Tosyl Chloride activation of a rayon/polyester cloth for protein immobilization", Biotechnology Techniques, Apr. 1993, vol. 7, 4:277-282.
Braga et al., "Hydrophobic Polymer Modification with Ionic Reagents: Polysterene Staining with Water-Soluble Dyes". Langmuir, vol. 19, No. 18, pp. 7580-7586 (2003).
Breslauer, K.J. et al., "Predicting DNA duplex stability from the base sequence". PNAS USA, vol. 83, pp. 3746-3750 (1986).
Brick, et al., "Formation of Colloidal Dispersions of Organic Materials in Aqueous Media by Solvent Shifting". Langmuir, vol. 19, No. 16, pp. 6367-6380 (Jan. 31, 2003).
Broude et al., "Multiplex allele-specific target amplification based on PCR suppression". PNAS. vol. 98, No. 1, pp. 206-211 (2001).
Brown, Patrick O., et al., "Exploring the new world of the genome with DNA microarrays". Nature Genetics Supplement, vol. 21, pp. 33-37 (Jan. 1999).
Buck et al., "Design Strategies and Performance of Custom DNA Sequence Primers". BioTechniques, vol. 27, pp. 528-536 (Sep. 1999).
Bunce et al., "Phototyping: Comprehensive DNA Typing for HLA-A, B, C, DRB1, DRB2, DRB3, DRB4, DRB5 & DQB1 by PCR with 144 primer mixes utilizing sequence-specific primers (PCR-SSP)". Tissue Antigens, vol. 46, No. 5, pp. 355-367 (Nov. 1995).
Bunce, M., et al., "Comprehensive serologically equivalent DNA typing for HLA-A by PCR using sequence specific primers (PCR_SSP)", Tissue Anitigens 45 : 81-90 (1995).
Burbulis, I, et al., "Using protein-DNA chimeras to detect and count small numbers of molecules". Nature Methods, vol. 2, No. 1, pp. 31-37 (Jan. 2005).
Cai et al., "Flow cytometry-based minisequencing: A new platform for high-throughput single-nucleotide polymorphism scoring", Genomics 66:135-143 (2000).
Campbell, C. J., et al., "Cell Interaction Microarray for Blood Phenotyping". Analytical Chemistry, vol. 78, pp. 1930-1938 (2006).
Campian et al. Colored and fluorescent solid supports. Innovation and Perspectives in Solid Phase Synthesis. Ed: E. Birmingham (Mayflower, London), pp. 469-474 (1994).
Cao et al., "High and intermediate resolution DNA typing systems for class I HLA-A, B, C genes by hybridization with sequence-specific oligonnucleotide probes (SSOP)", Rev Immunogenetics 1:177-208 (1999).
Cao et al., "Nanoparticles with Raman Spectroscopic Fingerprints for DNA and RNA Detection" , Science 197:1536-1539 (2002).
Caruso et al., "Magnetic Core-Shell Particles: Preparation of Magnetite Multilayers on Polymer Latex Microspheres". Advanced materials, vol. 11, No. 11, pp. 950-953 (1999).
Caruso, et al., "Magnetic Nanocomposite Particles and Hollow Spheres Constructed by a Sequential Layering Approach". Chem Mater, vol. 13, No. 1, pp. 109-116 (2001).
Caruso. "Nanoengineering of Particle Surfaces". Advanced Materials, vol. 12, No. 1, pp. 11-22 (2001).
Casnellie JE, et al., "Phosphorylation of synthetic peptides by a tyrosine protein kinase from the particulate fraction of a lymphoma cell line". Proc natl Sci USA, vol. 79, No. 2, pp. 282-286 (1982).
Chalmers, et al., "An instrument to determine the magnetophoretic mobility of labeled, biological cells and paramagnetic particles". Journal of Magnetism and Magnetic Materials, vol. 194, pp. 231-241 (1999).
Chan et al. The Bipohysics of DNA Hybridization with Immobilized Oligonucleotide Probes. Biophysical Journal 69: pp. 2243-2255 (1995).
Chang, et al., "New Approach to Produce monosized Polymer Microcapsules by the Solute Co-diffusion Method". Langmuir, vol. 17, No. 18, pp. 5435-5439 (2001).
Zhang et al., "Reconstruction of DNA sequencing by hybridization". Bioinformatics, vol. 19, No. 1, pp. 14-21 (2003).
Chaudhry et al., "Reactivity of human apurinic/apyrimidinic endonucleoase and *Escheria coli* exonucleonase III with bistranded abasic sites in DNA". The Journal of Biological Chemisty., vol. 272: 15650-15655 (1997).
Chee, M. et al., "Accessing genetic information with high-density DNA arrays". Science, vol. 274, pp. 610-613 (1996).

(56) References Cited

OTHER PUBLICATIONS

Chen et al., "A Microsphere-Based assay for multiplexed single nucleotide polymorphism analysis using single base chain extension", Genome Research, Cold Spring Harbor Laboratory Press 10:549-557 (2000).
Zhang et al., "Nuclear DNA analysis in genetic studies of populations; practice, problems and prospects" Molecular Ecology. vol. 12:563-584 (2003).
Chen, YX, et al., "Deletion of arginine codon 229 in the Rhce gene alters e and f but not c antigen expression". vol. 44, No. 3, pp. 391-398 (Mar. 2004).
Cheng, et al., "A Synthetic peptide derived from p34cdc2 is a Specific and Efficient Substrate of SRC-Family Tyrosine Kinases". J Biol Chem, pp. 9248-9256. vol. 267, No. 13 (1992).
Zborowski, et al., "Continuous cell separation using novel magnetic quadruple flow sorter". Journal of Magnetism and Magnetic Materials, vol. 194, pp. 224-230 (1999).
Cherepinsky, Vera, "On mathematical aspects of genomic analysis", Ph.D. Thesis, published Mar. 2004.
Cheung, V. G., et al., "Making and Reading Microarrays". vol. 21, pp. 15-19 (Jan. 1999).
Choi, et al., "An on-chip magnetic separator using spiral electromagnets with semi-encapsulated permalloy". Biosensors & Bioelectronics, vol. 16, pp. 409-416 (2001).
Yellen, B. B., et al., "Programmable Assembly of Colloidal Particles Using Magnetic Microwell Templates". Langmuir, p. est 6.5 (2004).
Clerc, P., et al., "Advanced deep reactive ion etching: a versatile tool for microelectromechanical systems". J. Micromech Microeng, vol. 8, No. 4, pp. 272-278 (Dec. 1998).
Coffer et al., "Characterization of Quanum-Confined CdS Nanocrystallites Stabilized by Deoxyribonucleic Acid (DNA)" Nanotechnology, 1992 3:69-75.
Yeh, S. R., et al., "Assembly of ordered colloidal aggregares by electric-field-induced fluid flow". Nature, Mar. 6, 1997; vol. 386, No. 6620, pp. 57-59.
Colombie, et al., "Role of Mixed Anionic-Nonionic Systems of Surfactants in the Emulsion Polymerization of Styrene: Effect on Particle Nucleation". Macromolocules, vol. 33, No. 20, pp. 7283-7291 (2000).
Cosgrove et al. "A Small-angle neutron scattering study of the structure of gelatin at the surface of polystyrene latex particles". Langmuir. vol. 14:5376-5382 (1998).
Coyne et al., "Assymetric PCR for ssDNA Production", Molecular Biology Techniques Manual. Third Edition. Jan. 1994, Feb. 2001; http://www.mcb.uct.ac.za/percond.htm.
Crisp, M., et al., "Preparation of Nanoparticle Coatings on Surfaces of Complex Geometry". Nano Letters, vol. 3, No. 2, pp. 173-177 (2003).
Cronin M.T. et al., "Cystic Fibrosis Mutation Detection by Hybridization to Light-Generated DNA Probe Arrays," Human Mutation, John Wiley & Sons, Inc., US, vol. 7, No. 3, pp. 244-255 (Jan. 1996).
Cruse et al., "Illustrated Dictionary of Immunology". Boca Raton: CRC Press, p. 512 (2003).
Dai-Wu Seol, et al., "Signaling Events Triggered by Tumor Necrosis Factor-related Apoptosis-inducing Ligand (TRAIL): Caspase-8 is Required for TRAIL-Induced Apoptosis". Cancer Research, vol. 61, pp. 1138-1143 (2001).
Dasgupta, et al., "Flow of multiple fluids in a small dimension". Analytical Chemistry, vol. 74, No. 7, pp. 208-213 (2002).
De Farias, P., et al., Investigation of red blood cell antigens with highly fluorescent and stable semiconductor quantum dots, J. Bimedical Optics, 2005, pp. 1-4, vol. 10(4).
Decher, G., "Fuzzy Nanoassemblies: Toward Layered Polymeric Multicomposites". Science, vol. 277, pp. 1232-1237 (Aug. 29, 1997).
Denomme, G. A., et al., "High throughput multiplex single-nucleotide polymorphism analysis for red cell and platelet antigen genotypes". Transfusion, vol. 45, pp. 660-666 (May 2005).
Denkov et al. "Mechanism of Formation of Two-Dimensional Crystals from Latex Particles on Substrates," langmuir, 1992, pp. 3183-3190, vol. 8.

Ding et al., "Direct molecular haplotyping of long-range genomic DNA with M1-PCR", Jun. 2003, vol. 100, 13: 7449-7453.
Du et al., "Sensitivity and Specificity of Metal Surface-Immobilized," Molecular Beacon, Biosensors; JACS 2005, vol. 127, No. 21, pp. 7932-7940.
Duggan, David J., et al., "Expression profiling using cDNA microarrays". Nature Genetics Supplement, vol. 21, pp. 10-14 (Jan. 1999).
Dunbar SA et al. "Application of the luminex LabMAP in rapid screening for mutations in the cystic fibrosis transmembrane conductance regulator gene: A pilot study" Clin Chem Sep. 2000; 46(9): 1498-500. with Abstract data, pp. 1 and 2.
Duquesnoy HLA Matchmaker: A Molecularly Based Algorithm for Histocompatibility Determination. I. Description of the Algorithm. Human Immunology, vol. 63, pp. 339-352 (2002).
Dziennik, S. R., et al., "Nondiffusive mechanisms enhance protein uptake rates in ion exchange particles". PNAS, vol. 100, No. 2, pp. 420-425 (2003).
Easteal, S. "DNA Fingerprinting by PCR Amplification of HLA Genes". DNA and Criminal Justice; Human Genetics Group, John Curtin School of Medical Research, pp. 121-127 (1991).
Egner et al. "Tagging in combinatorial chemistry: the use of coloured and fluorescent beads". Chem. Commun. pp. 735-736 (1997).
Elaissari et al., "Hydrophilic and cationic latex particles for the specific extraction of nucleic acids". J. Biomater, Sci Polymer Edn, vol. 10, pp. 403-420 (1999).
Erdogan et al., "Detection of mitochondrial single nucleotide polymorphisms using a primer elongation reaction on oligonucleotide microarrays", Nucleic Acid Research, 29 : 1-7 (2001).
Ericsson, O., et al., "A dual-tag microarray platform for high-performance nucleic acid and protein analyses". Nucleic Acids Research, vol. 36, No. 8 e45, pp. 1-9 (2008).
Erlich, et al., "HLA DNA Typing and Transplantation", Immunity, 14: 347-356 (2001).
Fan et al., "Parallel Genotyping of Human SNPs Using Generic High-density Oligonucleotide Tag Arrays", Genome Research, vol. 10, pp. 853-860 (2000).
Fatin-Rouge, N., et al., "Diffusion and Partitioning of Solutes in Agarose Hydrogels: The Relative Influence of Electrostatic and Specific Interactions", J. Phys. Chem. B., vol. 107, pp. 12126-12137 (2003).
Ferguson et al., "High-Density Fiber-Optic DNA Random Microsphere Array". Anal. Chem, vol. 72, pp. 5618-5624 (2000).
Filipovich et al., "Impact of donor type on outcome of bone marrow transplantation for Wiskott-Aldrich syndrome: collaborative study of the International Bone Marrow Transplant Registry and the National Marrow Donor Program", Blood, vol. 97, No. 6, pp. 1598-1603 (2001).
Finkel, et al. "Barcoding the Microworld". Analytical Chemistry, pp. 353-359 (Oct. 1, 2004).
Fitch, J.P. et al., "Rapid Development of Nucleic Acid Diagnostics", Proceedings of the IEEE 90 (11): 1708-1720 (Nov. 2002).
Fluorescent Microspheres (Tech. Note #19). Bangs Laboratories (1997).
Fodor, S., et al., "Light-Directed, Spatially Addressable Parallel Chemical Synthesis". Research Article (Authors are at the Affymax Research Institute, 3180 Porter Drive, Palo Alto, CA 94304), pp. 767-773 (Feb. 15, 1991).
Fowke, Keith R., et al. "Genetic analysis of human DNA recovered from minute amounts of serum or plasma". Journal of Immunological Methods, vol. 80, pp. 45-51 (1995).
Frengen, Jomar, et al., "Demonstration and Minimization of Serum Interference in Flow Cytometric Two-Site Immunoassays". Clinical Chemistry, vol. 40, No. 3, pp. 420-425 (1994).
Fuh et al. Single Fibre Optic Fluorescence pH Probe. Analyst, 112:1159-1163 (1987).
Fuh et al., "A Method for Determination of Particle Magnetic Susceptibility with Analytical Magnetapheresis". Anal. Chem, vol. 72, pp. 3590-3595 (2000).
Fulton et al. "Advanced multiplexed analysis with the FlowMetrix system". Clinical Chemistry, vol. 43:9, pp. 1749-1756 (1997).

(56) References Cited

OTHER PUBLICATIONS

Gahan, P. B., "Circulating Nucleic Acid in Plasma and Serum: Diagnosis and Prognosis in Cancer". Oncology, vol. 32, No. 6, pp. 20-22 (Oct. 2008); Weekly news updates on www.cli-online.com.
Garber, K. "More SNPs on the Way". Science, vol. 281, No. 5384, pp. 1788-1790 (Sep. 18, 1998).
Gates, et al., "Photonic Crystals that can be Addressed with an External Magnetic Feld". Adv Mater, vol. 13, No. 21, pp. 1605-1608 (2001).
Gelfi, C., et al., "Investigation of the Properties of Novel Acrylamido Monomers by Capilary Zone Electrophoresis", Journal of Chromatography, vol. 608, pp. 333-341 (1992).
Gerlach. Human Lymphocyte Antigen Molecular Typing. Archives of Pathology & Laboratory Medicine. vol. 126, pp. 281-284 (2002).
Ghazaly, et al., "Synthesis and Characterization of a Macromonomer Crosslinker". Journal of Applied Polymer Science, vol. 77, pp. 1362-1368 (2000).
Ghosh et al. "Covalent attachement of oligonucleotides to solid supports". Nucleic Acids Research. vol. 16, No. 13; pp. 5363-5371 (1987).
Ghosh, P., et al., "A Simple Lithographic Approach for Preparing Patterned, Micron-Scale Corrals for Controlling Cell Growth". Angew. Chem. Int. Ed., vol. 38, No. 11, pp. 1592-1595 (1999).
Giersig et al. Formation of ordered two-dimensional gold colloid lattices by electrophoretic deposition. J. Phys. Chem., vol. 97: 6334-6336 (Apr. 29, 1993).
Giorgi, R., et al., "Nanotechnologies for Conservation of Cultural Heritage: Paper and Canvas Deacidification". Langmuir, vol. 18, pp. 8198-8203 (2002).
Good, L., et al., "Bactericidal antisense effects of peptide-DNA conjugates". Nature Biotechnology, vol. 19, pp. 360-364 (2001).
Goodey et al., "Development of multianalyte sensor arrays composed of chemically derivatized polymeric microspheres localized in micromachined cavitites". Journal of American Chemical Society, vol. 123, pp. 2559-2570 (2001).
Graf et al., "A general method to coat colloidal particles with silica". Langmuir, vol. 19, pp. 6693-6700 (2003).
Grazia et al. In-vivo biomedical monitoring by fiber-optic system. Journal of Lightwave Technology. 13, 1396-1406 (1995).
Yellen, et al., "Statistical Analysis of Weakest Link in Chains of Magnetic Particle Carriers for Applications in Printing Biochemical Arrays". European Cells and Materials, vol. 3, pp. 88-91 (2002).
Grondahl, et al., "Encoding Combinatorial Libraries: A Novel Application of Fluorescent Silica Colloids". Langmuir, vol. 16, No. 25, pp. 9709-9715 (2000).
Gruttner, et al., "New types of silica-fortified magnetic nanoparticles as tools for molecular biology applications". Journal of Magnetism and Magnetic Materials, vol. 94, pp. 8-15 (1999).
Gubin et al., "Identification of the Dombrock blood group glycoprotein as a polymorphic member of the ADP-ribosyltransferase gene family", Blood, Oct. 1, 2000, vol. 96, No. 7, pp. 2621-2627.
Gullberg, M., et al., "Cytokine detection by antibody-based proximity ligation". PNAS, vol. 101, No. 22, pp. 8420-8424 (Jun. 2004).
Guo, Zhen et al. "Oligonucleotide arrays for high-throughput SNPs detection in the MHC class I genes: HLA-B as a model system". Genome Research; vol. 12, No. 3, pp. 447-457 (Mar. 2002).
Guo, Zhen, "Direct fluorescence analysis of genetic polymorphisms . . . oligonucleotide arrays on glass supports". Nucleic Acids Research, Jul. 1994, Oxford Univ Press, pp. 5456-5465.
Gupta et al. ("Hydrogels: from controlled release to pH-responsive drug delivery" Drug Discov Today. May 15, 2002;7(10):569-79.
Gustafsdottir, S. M., "In vitro analysis of DNA—protein interactions by proximity ligation". PNAS, vol. 104, No. 9, pp. 3067-3072 (Feb. 2007).
Haab et al. Single Molecule Fluorescence Burst Detection of DNA Fragments Separated by Capillary Electrophoresis. Analytical Chemistry, vol. 67 (No. 18) : 3253-3256 (1995).
Hacis et al., "Resequencing and mutational analysis using oligonucleotide nnicroarrays", Nature America; 21 : 42-47 (1999).

Hakala, H., et al. "Simultaneous detection of several oligonucleotides by time-resolved fluorometry: the use of a mixture of categorized microparticles in a sandwich type mixed-phase hybridization assay". Nucleic Acids Research, vol. 26, pp. 5581-5585 (1998).
Hashimi et al., "A Flexible Array format for large-scale, rapid blood group DNA typing". Transfusion, Published Online Apr. 6, 2004, vol. 45, Issue 5, pp. 680-688 (May 2005).
Hashmi, G., et al, "Determination of 24 minor red blood cell antigens for more than 2000 blood donors by high-throughput DNA analysis". Transfusion, vol. 47, No. 4, pp. 736-747 (Apr. 2007).
Zaer, Farid, et al., "Antibody Screening by Enzyme-Linked Immunosorbent Assay Using Pooled Soluble HLA in Renal Transplant Candidates". Transplantation, vol. 63, No. 1, pp. 48-51 (Jan. 15, 1997).
Heinrich, et al., "Interleukin-6-type Cytokine Signaling through the gp 130/Jak/STAT pathway". Biochem J, vol. 334, pp. 297-314 (1998).
Helgesen, et al., "Aggregation of magnetic microspheres: experienents and simulations". Physical Review Letters, vol. 61, No. 15, pp. 1736-1739 (1998).
Helmuth, R., et al., "HLA-DQ Allele and Genotype Frequencies in Various Human Populations, Determined by Using Enzymatic Amplification and Oligonucleotide Probes". Am. J. Hum. Genet, vol. 47, pp. 515-523 (1990).
Hermanson, G. T., "Nucleic Acid and Oligonucleotide Modification and Conjugation". Bioconjugate Techniques, Academic Press, Chapter 17, pp. 639-671 (Jan. 15, 1996).
Yershov et al., "DNA analysis and diagnostics on oligonulceotide microchips". Proceedings of the National Academy of Sciences of the United States of America, vol. 93, No. 10, pp. 4913-4918 (May 14, 1996).
Hiller, J., et al., "Reversibly erasable nanoporous anti-reflection coatings from polyelectrolyte nnultilayers". Nature Materials, vol. 1, pp. 59-63 (Sep. 2002).
Hirata, H., et al., "Caspases Are Activated in a Branched Protease Cascade and Control Distinct Downstream Processes in Fas-induced Apoptosis". J. Exp. Med., vol. 187, No. 4, pp. 587-600 (1998).
Hizume, et al., "Tandem repeat DNA localizing on the proximal DAPI bands of chromosomes in Larix, pinaceae". Genome, vol. 45, pp. 777-783 (2002).
Holtz, J., et al., "Intelligent Polymerized Crystalline Colloidal Array Novel Sensor Materials", Analytical Chemistry, vol. 70, No. 4, pp. 780-791 (1998).
Houghton. "General method for the rapid solid-phase synthesis of large numbers of peptides: specificity of anitgen-antibody interaction at the level of individual amino acids". Proc. Natl. Avad. Sci. USA. vol. 82:5131-5135 (1985).
Huff et al., "Technical Milestone: Development of the Logical Observation Identifier Names and Codes (LOINC) Vocabulary". JAIMA, vol. 5, pp. 276-292 (1998).
Iannone, Marie A., et al., "Multiplexed Single Nucelotide Polymorphism Genotyping by Oligonucleotide Ligation and Flow Cytometry". Cytometry, vol. 39, Issue 2, pp. 131-140 (Feb. 17, 2000).
Ide et al., "Synthesis and damage specificity of a novel probe for the detection of abasic sites in DNA". Biochemistry. vol. 32: 8276-8283 (1993).
Ito, Y., et al., "Patterned Immobilization of Thermoresponsive Polymer", Langmuir, vol. 13, pp. 2756-2759 (1997).
Iwayama, et al., "Optically Tunable Gelled Photonic Crystal Covering Almost the Entire Visible Light Wavelength Region", Langmuir (2002).
Jackman, R. J., et al., "Using Elastomeric Membranes as Dry Resists and for Dry Lift-Off", Langmuir, vol. 15, pp. 2973-2984 (1999).
Jeon, N. L., et al., "Patterned polymer growth on silicon surfaces using microcontact printing and surface-initiated polymerization", Applied Physics Letters, vol. 75, No. 26, pp. 4201-4203 (1999).
John C. Guatelli et al., "Isothermal, in vitro amplification of nucleic acids by a multienzyme reaction modeled after retroviral replication," Proc. Nat'l Academy of Science USA, vol. 87: pp. 1874-1878 (1990).

(56) References Cited

OTHER PUBLICATIONS

Johnson, K. L., et al., "Surface Energy and the Contact of Elastic Solids". Proceedings of the Royal Society of London, Series A, Mathematical and Physical Sciences, vol. 324, No. 1558, pp. 301-313 (Sep. 8, 1971).

Jones et al., "Constraint, Optimization, and Hierarchy: Reviewing Stereoscopic Correspondence of Complex Features". Computer Vision and Image Understanding, vol. 65, No. 1, pp. 57-78 (1997).

Jones et al., "Dielectrophoretic liquid actuation and nanodroplet formation", Journal of Applied Physics, vol. 89, No. 2, pp. 1441-1448 (Jan. 15, 2001).

Kakabakos et al. "Immobilization of Immunoglobulins onto Surface-treated and Untreated Polystyrene Beads for Radioimmunoassays" Clin. Chem. 36 (1990), 492-496.

Kalinina, O., et al., "A core-shell Approach to Producing 3D Polymer Nanocomposites", Macromolecules, vol. 32, pp. 4122-4129 (1999).

Kamholz, et al., "Optical measurement of transverse molecular diffusion in a microchannel". Biophysical Journal, vol. 80, pp. 1967-1972 (2001).

Kamm, R. C., et al. "Nucleic Acid Concentrations in Normal Human Plasma". Clinical Chemistry, vol. 18, pp. 519-522 (1972).

Kandimalla et al., "Cyclicons" as Hybridization-Based Fluorescent Primer-Probes: Bioorganic & Medicinal Chemistry 8 (2000) 1911 to 1916".

Kelly, J.J., et al., "Radical-generating coordination complexes as tools for rapid and effective fragmentation and fluorescent labeling of nucleic acids for microchip hybridization". Analytical Biochemisty, vol. 311, No. 2, pp. 103-118 (Dec. 15, 2002).

Klintschar, et al., "Genetic variation at the STR loci D12S391 and CSF1PO in four populations from Austria, Italy, Egypt and Yemen". Forensic Sci. Int. vol. 97:37-45 (1998).

Kim, E., et al., "Polymer microstructures formed by moulding in capillaries", Nature, vol. 376, pp. 581-584 (1995).

Knipper, et al., Accession No. AF221125.1.1 on Electronic Database at NCBI (Feb. 16, 2000).

Koch et al., "PNA-Peptide Chimerae". Tetrahedron Letters, vol. 36, pp. 6933-6936 (1995).

Koh, et al., "Molding of Hydrogel Microstructures to Create Multiphenotype Cell Microarrays". Analytical Chemistry (2003).

Koh, et al., "Poly(ethylene glycol) Hydrogel Microstructures Encapsulating Living Cells". Langmuir, vol. 18, pp. 2459-2462 (2002).

Kolch. "Meaningful Relationships: The Regulation of the Ras/Raf/MEK/ERK pathway by protein interactions". Biochem J, vol. 351, pp. 289-305 (2000).

Kotov, N., et al., "Layer-by-Layer Self-Assembly of Polyelectrolyte-Semicondictor Nanoparticle Composite Films". J. Phy Chem, vol. 99, pp. 13065-13069 (1995).

Krausa et al. "A Comprehensive PCR-ssP typing system for identification of HLA-A locus alleles", Tissue Antigens, 47 (3) : 237-244 (1996).

Krsko, P., et al., "Electron-Beam Surface Patterned Poly(ethylene glycol) Microhydrogels". Langmuir, vol. 19, pp. 5618-5625 (2003).

Krutzik P.O. et al., "Fluorescent cell barcoding in flow cytometry allows high-throughput drug screening and signal profiling". Nature Methods, vol. 3, No. 5, pp. 361-368 (2006).

Kubo et al., "A Novel Sensitive and specific assay for abasic sites, the most commonly produced DNA lesion". Biochemistry, vol. 13:3703-3708 (1992).

Kumacheva, E., et al., "Three-dimensional Arrays in Polymer Nanocompositites", Advanced Materials, vol. 11, No. 3, pp. 231-234 (1999).

Kurita-Ochiai, T., et al., "Butyric Acid-Induced T-Cell Apoptosis is Mediated by Caspase-8 and -9 Activation in a Fas-Independent Manner". Clinical and Diagnostic Laboratory Immunology, vol. 8, No. 2, pp. 325-332 (2001).

Vorlop, K. D., et al., "Entrapment of Microbial Cells within Polyurethane Hydrogel Beads with the Advantage of Low Toxicity", Biotechnology Techniques, vol. 6, No. 6, pp. 483-488 (1992).

Kwoh et al., "Transcription based amplification system and detection of amplified human immunodeficiency virus type 1 with a bead-based sandwich hybridization format". Proc. Natl. Acad. Sci, vol. 86, pp. 1173-1177 (Feb. 1989).

LaForge, K. S., et al., "Detection of Single Nucleotide Polymorphisms of the Human Mu Opioid Receptor Gene by Hybridization of Single Nucleotide Extension on Custom Oligonucleotide Gelpad Microchips: Potential in Studies of Addiction". American Journal of Medical Genetics (Neuropsychiatric Genetics), vol. 96, pp. 604-615 (2000).

Lagerholm et al., "Theory for Ligand Rebinding at Cell Membrane Surfaces," Biophysical Journal (1998), vol. 74, pp. 1215-1228.

Lamb, D. J., et al., "Modification of Natural and Artificial Polymer Colloids by Topology-Controlled Emulsion Polymerization". Biomacromolecules, vol. 2, No. 2, pp. 518-525 (2001).

Lander, E. S. "The New Genomics: Global Views of Biology". Sciences, vol. 274, No. 5287, pp. 536-539 (Oct. 25, 1996).

Lander, E. S., et al., "Array of Hope". Nature Genetics Supplement, Perspective, vol. 21, pp. 3-4, (Jan. 1999).

Latour, P., et al., "Polymorphic Short Tandem Repeats for Diagnosis of the Charot-Marie-Tooth IA Duplication". Clinical Chemistry, vol. 47, pp. 829-837 (2001).

Lau, F. Y., et al., "Provision of phenotype-matched blood units: no need for pre-transfusion antibody screening", Haematologica, vol. 86, No. 7, Jul. 2001, pp. 742-748.

Lee et al. "Quantitation of residual WBCs in filtered blood components by high-throughput, real time kinetic PCR", Blood Components, transfusion, vol. 42, pp. 87-93 (Jan. 2002).

Lee, et al., "Combination of Insulin-like Growth FActor (IGF)-1 and IGF-Binding Protein-1 Promotes Fibroblast-Embedded Collagen Gel Contraction". Endocrinology, vol. 137, pp. 5278-5283 (1996).

Lee, H. J., et al., "Fabricating RNA Microarrays with RNA-DNA Surface Ligation Chemistry". Analytical Chemistry, vol. 77, No. 23, pp. 7832-7837 (Dec. 1, 2005).

Lee, S., et al., "Control of Core-Shell Latex Morphology". Polymer Latexes, ACS Symposium, American Chemical Society, pp. 234-253 (1992).

Lemieux: "high throughput single nucleotide polymorphism genotyping technology" Current Genomics. vol. 1:301-311 (2000).

Lhomme et al. "Abasic DNA structure, reactivity and recognition". Biopolymers. vol. 52 : 65-83 (1999).

Li, A., et al., "Multiplexed analysis of polymorphisms in the HLA gene complex using bead array chips". Tissue Anitigens, vol. 63, pp. 518-528 (2004).

Liang L., et al., "Preparation of Composite-Crosslinked Poly(N-isopropylacrylamide) Gel Layer and Characteristics of Reverse Hydrophilic-Hydrophobic Surface", Journal of Applied Polymer Science, vol. 72, pp. 1-11 (1999).

Liang, L., et al., "Temperature-sensitive membranes prepared by UV photopolymerization of N-isoproprylacrylamide on a surface of porous hydrophilic polypropylene membranes", Journal of Membrane Science, vol. 162, pp. 235-246 (1999).

Liebert, M. R., et al., "Dynamics of the holes in human erythrocyte membrane ghosts". J. Biological Chemistry, vol. 257, No. 19, pp. 11660-11666 (1982).

Lin et al. "Raman Studies of Bovine Serum Albumin". Biopolymers 15:203-218 (1976).

Lindahl et al., "Rate of depuriniation of native deoxyribonucleic acid". Biochemistry. vol. 11, No. 19: 3610-1617 (1972).

Lindahl et al., "Rate of chain breakage at apurinic sites in double-stranded deoxyribonclueic acid" Biochemistry, vol. 11, No. 19:3618-3623 (1972).

Lipshutz, R. J., et al., "High Density Synthetic Oligonucleotide Arrays". vol. 21, pp. 20-24 (Jan. 1999).

Liu, et al., "Development of a Carbon Dioxide-Base Microencapsulation Technique for Aqueous and Ethanol-Based Latexes". Langmuir (2002).

Liu, V, et al, "Three-Dimensional Photopatterning of Hydrogels Containing Living Cell". Biomedical Microdevices, vol. 4, No. 4, pp. 257-266 (2002).

Lofas, et al., "Methods for site controlled coupling to carboxymethyldextran surfaces in surface plasmon resonance sensors". Biosensors & Bioelectronics, vol. 10, pp. 813-822 (1995).

(56) References Cited

OTHER PUBLICATIONS

Loomans, E., et al., "Assessment of the functional affinity constant of monoclonal antibodies using an improved enzyme-linked immunosorbent assay". Journal of Immunological Methods, vol. 184, pp. 207-217 (1995).

Ye et al., "Fluorescent Microsphere-Based Readout Technology for Multiplexed Human Single Nucleotide Polymorphism Analysis and Bacterial Identification" Human Mutation, Apr. 17, 2001 (4); 305-16).

Lund et al. Assessment of Methods for Covalent Bonding of Nucleic Acids to Magnetic Beads, Bynabeads, and the Characteristics of the Bound Nucleic Acids in Hybridization Reactions, Nucleic Acids REsearch vol. 16, No. 22, 10861-10880 (1988).

Luo et al., "Emulsion Copolymerization of Butyl Acrylate with Cationic Monomer Using Interfacial Redox Initiator System". Journal of Polymer Science, vol. 39, pp. 2696-2709 (2001).

Lvov, Y, et al., "Alernate Assembly of Ordered Multilayers of SiO2 and Other Nanoparticles and Polyions". Langmuir, vol. 13, pp. 6195-6203 (1997).

MacBeath et al., "Printing proteins as microarrays for high-throughput function determination". Science, vol. 289; pp. 1760-1763 (Sep. 8, 2000).

Maldonado-Rodriguez et al., "Hybridization of glass-tethered oligonucleotide probes to . . . ", Molecular Biotechnology, vol. 11, No. 1, pp. 1-12 (1999).

Marras et al., Multiplex detection of single-nucleotide variations using molecular beacons: Genetic Analysis: Biomolecular Engineering 14 (1999) 151-156.

Marsh, S. G. E., et al., The HLA Facts Book, "HLA Typing at the DNA Level", Academic Press, Chapter 6, pp. 37-39 (2000).

Martin, M., et al. "A Method for Using Serum or Plasma as a Source of DNA for HLA Typing". Human Immunology, vol. 33, pp. 108-113 (1992).

Martinell, J. et al., "Three mouse models of human thalassemia", Proc. Natl. Acad. Sci, USA. Aug. 1981, vol. 78, No. 8, pp. 5056-5060 (see especially p. 5057, col. 1, last paragraph, Figure 4, and the legend to Figure 4.

Maskos, U. et al., "Parallel analysis of oligodeoxyribonucleotide (oligonucleotide) interactions. I. Analysis of factors influencing oligonucleotide duplex formation". Nucleic Acids Research, vol. 20, No. 7, pp. 1675-1678 (1992).

Maskos, U., et al., "Oligonucleotide hybridisations on glass supports: a novel linker for oligonucleoptide synthesis and hybridisation properties of oligonucleotides synthesized in situ". Nucleic Acids Research, vol. 20, No. 7, pp. 1679-1684 (1992).

Matthews et al., "Biochemistry: A Short Course". New York: John Wiley & Sons, Inc, p. 25 (1997).

Maxam et al., "A new method for sequencing DNA," Proc. Natl. Acad. Sci. USA. vol. 74, No. 2, pp. 560-564, Feb. 1977.

McCloskey, et al., "Magnetic Cell Separation: Characterization of Magnetophoretic Mobility". Anal. Chem., vol. 75, pp. 6868-6874 (2003).

McCloskey, et al., "Magnetophoretic Mobilities Correlate to Antibody Binidng Capacities". Cytometry, vol. 40, pp. 307-315 (2000).

Mei et al. "Genome-wide Detection of Allelic Imbalance Using Human SNPs and High-Density DNA Arrays". Genome Research. vol. 10, pp. 1126-1137 (2000).

Michael, et al., "Randomly ordered addressable high-density optical ssensor arrays". Anal. Chem, vol. 70, pp. 1242-1248 (1999).

Micheletto et al., "A simple method for the production of a two-dimensional ordered array of small latex particles". Langmuir, vol. 11, pp. 3333-3336 (1995).

Moller, E., et al., "The Use of Magnetic Beads Coated with Soluble HLA Class I or Class II Proteins in Antibody Screening and for Specificity Determination of Donor-Reactive Antibodies". Transplantation, vol. 61, No. 10, pp. 1539-1545 (May 27, 1996).

Moore, et al., "The use of magnetite-doped polymeric microspheres in calibrating cell tracking velocimetry". J. Biochem. Biophys. Methods, vol. 44, pp. 115-130 (2000).

Morag et al. "Immobilized nitro-avidin and nitro-streptavidin as reusable affinity matrices for application in avidin-biotin technology". Analytical Biochemistry. vol. 243: 257-263 (1996).

Mori, et al., Computer program to predict liklihood of finding an HLA-matched donor: Methodology, validation, and application. Biology of Blood and Marrow Transplantation, vol. 2, pp. 134-144 (1996).

Morishima et al., "Microflow system and transportation of DNA molecule by dielectrophoretic force utilizing the conformational transition in the higher order structure of DNA molecule". Proceedings—IEEE Annual International Workshop on Micro Electro Mechanical Systems: An investigation of micro structures, sensors, actuators, machines and robots. Nagoya, Jan. 26-30, 1997.

Muller et al., "Gene and Haplotype Frequencies for the Loci HLA-A, HLB-B, and HLA-DR Based on Over 13,000 German Blood Donors". Human Immunology, 2003, 64: 137-151.

Mullis et al. Specific Synthesis of DNA in Vitro via a Polymerase-Catalyzed Chain Reaction Methods in Enzymology, 1987; vol. 155, pp. 335-350.

Nagarajan et al., "Identifying Spots in Microarray Images", IEEE Transactions on Nanobioscience, vol. 1, No. 2, pp. 78-84 (Jun. 2002).

Nagayama et al., "Fabrication of two-dimensional colloidal arrays". Phase Transitions, vol. 45, 185-203 (1993).

Nam, J., et a., "Colorimetric Bio-Barcode Amplification Assay for Cytokines". Anal. Chem., vol. 77, pp. 6985-6988 (2005).

Nau et al., "A Command Processor for the Determination of Specificities fro Matrices of Reactions Between Blood Cells and Antisera". Computers and Biomedical Research, vol. 10, pp. 259-269 (1977).

Nazarenko et al. (2002) Multiplexed quantitiative PCR using self-quenched primers labeled with a single fluorophore. Nucleic Acids Research, 30 (9), e37.

Niemeyer et al., "DNA-directed Immobilization: Efficient, Reversible, and Site- Selective Surface Binding of Proteins by means of Covalent Stretavidin Conjugates". Analytical Biochemistry, vol. 268, pp. 54-63 (1999).

Niemeyer et al., "Oligonucleotide-directed self-assembly of proteins: semisynthetic DNA—streptavidin hybrid molecules as connectors for the generation of macroscopic arrays and the construction of supramolecular bioconjugates". Nucleic Acids Research, vol. 22, pp. 5530-5539 (1994).

Nygren, "Molecular Diagnostics of Infectious Diseases" Royal Institute of Technology Department of Biotechnology, Stockholm 2000, pp. 1-68.

Ohlmeyer, M. H. J. et al. "Complex Synthetic Chemical Libraries Indexed with Molecular Tags". Proceedings of the National Academy of Sciences, USA, National Academy of Science, Washington DC. vol. 90, Dec. 1, 1993, pp. 10922-10926.

Okubo, and Yamashita. "Thermodynamics for the preparation of micorn-sized, monodispersed highly monomer-'absorbed' polymer particles utilizing the dynamic swelling method." Colloids and Surfaces, 1999:153-159.

Okubo, et al., "Preparation of micron-size monodisperse polymer particles by seeded polymerization utilizing the dynamic monomer swelling method". Colloid and Polymer Science, vol. 269, No. 3, pp. 222-226 (1991).

Olejnik et al., "Photocleavable biotin phosphoramidite for 5'-end-labeling, purification & phosphorylation of oligonucleotides", Nucleic Acids Research 1996, vol. 24, 2:361-366.

Oliver, D., et al, "Use of Single Nucleotide Polymorphisms (SNP) and Real-Time Polymerase Chain Reaction for Bone Marrow Engraftment Analysis". Journal of Molecular Diagnostics, vol. 2, No. 4, pp. 202-208 (Nov. 2000).

Olson et al. "A common langauage for physical mapping of the human genome". Science, vol. 245, pp. 1434-1435 (1989).

Otero, T. F., et al., "Electrochemically initiated acrylic acid/acrylamide copolymerization", J. Electroanal. Chem., vol. 256, pp. 433-439 (1998).

Otero, T. F., et al., "Electroinitiated polymerization of acrylamide in DMG: Attempts at an interfacial model", J. Electroanal. Chem., vol. 304, pp. 153-170 (1991).

Pastinen, et al., "A System for specific, high-throughput genotyping by allele-specific primer extension on microarrays". Genome Res., vol. 10, pp. 1031-1042 (2000).

(56) References Cited

OTHER PUBLICATIONS

Peter, C., et al., "Optical DNA-sensor chip for real-time detection of hybridization events". Fresenius J. Anal. Chem, vol. 371, pp. 120-127 (Jun. 2001); Published online Springer-Verlay 2001.

Wilson, M. R., et al., "A New Microsphere-based Immunofluorescence Assay for Antibodies to Membrane-associated Antigens". Journal of Immunological Methods, vol. 107, pp. 231-237 (1988).

Peterson, et al. "Fiber Optic pH probe for physiological use". Anal. Chem. vol. 52, 864-869 (1980).

Peterson, et al., "Fiber Optic Sensors for Biomedical Applications". Science, vol. 13; pp. 123-127 (1984).

Peytavi et al., "Correlation between microarray DNA hybridization efficiency and the position of short capture probe on the target nucleic acid". Biotechniques, vol. 39, No. 1, pp. 89-96 (2005).

Pooga, M., et al., "Cell-Penetrating constructs regulate galanin receptor levels and modify pain transmission in vivo" Nature Biotechnology, vol. 16, pp. 857-861 (1998).

Pope. "Fiber optic chemical microsensors employing optically active silica microspheres". SPIE, vol. 2388; pp. 245-256 (1995).

Prati D. et al., DNA Enzyme Immunoassay of the PCR-Amplified HLA-DQ Alpha Gene for Estimating Residual Leukocytes in Filtered Blood Clincial and Diagnostic Laboratory Immunology, Mar. 1995, p. 182-185.

Pregibon et al, "Magnetically and Biologically Active Bead-Patterned Hydrogels". Langmuir, vol. 22, pp. 5122-5128 (2006).

Preza, "Phase Estimation using rotational diversity for differential interference contrast microscopy". DISSERATION presented to the Washington University, Server Institute of Technology, Department of Electrical Engineering; St. Louis, MO (Aug. 1998).

Proudinikov et al., "Chemical methods of DNA and RNA fluorescent labeling". Nucleic Acids Research. vol. 24, No. 22: 4535-4542 (1996).

Proudnikov, D., et al., "Immobilization of DNA in Polyacrimide Gel for the Manufacture of DNA and DNA-Oligonucleotide Microchips", Analytical Biochemistry, vol. 259, pp. 34-41 (1998).

Quon, R., et al., "Measurement of the Deformation and Adhesion of Rough Solids in Contact". J. Phys. Chem., vol. 103, pp. 5320-5327 (1999).

Rabbany et al., "Assessment of hetrogeneity in antibody displacement reactions". Anal Chem, vol. 69, pp. 175-182 (1997).

Radtchecnko et al., "Core-shell structures formed by the solvent-controlled precipitation of luminescent ScTe nanocrystals on latex spheres". Advanced Materials, vol. 13, No. 22, pp. 1684-1687 (2001).

Radtkey et al., "Rapid, high-fidelity analysis of simple sequence repeats on an electronically active DNA microchip". Nucleic Acids Research, vol. 28, No. 7, p. e17 (2000).

Ramsay, G., "DNA Chips: State-of-the-Art". Nature Biotechnology, vol. 16, pp. 40-44 (Jan. 1998).

Reddy et al., "Determination of the Magnetic Susceptibility of Labeled Particles by Video Imaging". Chemical Engineering Science, vol. 51, No. 6, pp. 947-956 (1996).

Reid M.E., et al., "Novel Dombrock blood group genetic variants . . . ", Blood (ASH Annual Meeting Abstract) 2004, 104: Abstract 383.

Relogio, A. et al., "Optimization of oligonucleotide-based DNA microarrays", Nucl. Acids Res., vol. 30, e51, pp. 1-10 (2002).

Richardson et al., "The use of coated paramagnetic particles as a physical label in a magneto-immunassay". Biosensors & Bioelectronics, vol. 16, pp. 989-993 (2001).

Richardson, et al., "A novel measuring system for the determination of paramagnetic particle lables for use in magneto-immunoassays". Biosensors & Bioelectronics, vol. 16, pp. 1127-1132 (2001).

Richetti et al., "Two-dimensional aggregations and crystallization of a colloidal suspension of latex spjeres", J. Physique Letter. vol. 45, pp. L-1137 to L-1143 (1984).

Righetti, P. G., et al., "Electrophoresis gel media: the state of the art", J. Chromatogr B., Biomed Sci Appl, vol. 699, No. 1-2, pp. 63-75 (Oct. 10, 1997).

Roberts et al. "Patterned magnetic bar array for high-thoughput DNA detection" IEEE Transaction on Magnetics. vol. 40, No. 4: 3006-3008 (2004).

Rubina et al, "Hydrogel drop microchips with immobilized DNA: properties and methods for large-scale production". Analytical Biochemistry, vol. 325, pp. 92-106 (2004).

Rudzinski, et al., "pH-sensitive acrylic-based copolymeric hydrogels for the controlled release of a pesticide and a micronutrient". Journal of Applied Polymer Science, vol. 87, pp. 394-403 (2003).

Sacchetti, et al. "Efficiency of Two Different Nine-Loci Short Tandem Repeat Systems for DNA Typing Purposes". Clinical Chemistry, vol. 45, No. 2, pp. 178-183 (1999).

Saito, K., et al., "Detection of Human Serum Tumor Necrosis Factor-alpha in Healthy Donors, Using a Highly Sensitive Immuno-PCR Assay". Clinical Chemistry, vol. 45, No. 5, pp. 665-669 (1999).

Sambrook et al., "Precipitation with Ethanol or Isopropanol", Concentrating Nucleic Aicds, Molecular Cloning vol. 3, pp. E3-E4 and E.10-E.15 (1989).

Sano, T, et al., "Immuno-PCR: Very Senisitive Antigen Detection by Means of Specific Antibody-DNA Conjugates". Science, vol. 258, pp. 120-122 (Oct. 2, 1992).

Santa Lucia, J. Jr., "A unified view of polymer, dumbbell, and oligonucleotide DNA nearest-neighbor thermodynamics". PNAS USA, vol. 95, pp. 1460-1465 (1998).

Schaid et al., "Score Tests for Association between traits and Haplotypes when Linkage Phase is Ambiguous", American Journal of Genetics. vol. 70, pp. 425-434 (2002).

Schena et al., "Quantitative Monitoring of Gene Expression Patterns with a Complementary DA Microarray". Science, vol. 270, pp. 467-470 (1995).

Schouten, Jan P., et al., "Relative Quantification of 40 Nucleic Acid Sequences by Multiplex Ligation-Dependent Probe Amplification". Nucleic Acids Research, vol. 30, No. 12, e57 (Jun. 15, 2002).

Schreiber, G. B., et al., "Increasing Blood Availability by changing Donation Patterns". Transfusion, vol. 43, pp. 591-597 (2003).

Schreuder et al., "The HLA Dictionary 1999: A Summary of HLA-A, B, C, DRB1/3/4/5, DOB1 alleles and their association with serologically defined HLA-A, B, C, DR and DQ antigens", Tissue Antigens 54 : 409-437 (1999).

Schumaker, et al., "Mutation Detection by solid phase primer extension", Human Mutation 7:346-354 (1996).

Wilson et al., "A generalized method for magnetite nanoparticle steric stabilization utilizing block copolymers containing carboxylic acids". European Cells and Materials, vol. 2, Suppl 2, pp. 202-209 (2002).

Schuster et al. "Allele-specific and asymetric polymerase chain reacton amplification in combination: a one step polymerase chain protocol for rapid diagnosis of familial defective apolipoprotein B-100", Anal Biochem. Jul. 1992; 204 (1):22-5).

Scillian, James J., et al., "Early Detection of Antibodies Against rDNA-Produced HIV Proteins with a Flow Cytometric Assay". Clinical Chemistry, vol. 40, No. 3, pp. 420-425 (1994).

Scott et al., "Properties of Fluorophores on solid phase resins; Implications for screening, encoding and reaction monitoring". Bioorganic & Medicinal Chemistry Letter, vol. 7, No. 12, pp. 1567-1572 (1997).

S. Dubiley et al., "Polymorphism Analysis and Gene Detection by minsequencing on an array of gel immobilized primers." Nucleic Acids Research, 1999;i-vi. vol. 27, No. 16.

S. Ebel et al. "Very Stable Mismatch Duplexes: Structural and Thermodynamic Studies on G-A Mismatches in DNA" Biochemistry 31:12083-86 (1992).

Seeman, P., et al., "Structure of Membrane Holes in Osmotic and Saponin Hennolysis"; The Journal of Cell Biology, vol. 56; pp. 519-527 (1973).

Sehgal et al. "A method for the high effieiency of water-soluble carbodiimide-mediated amidation". Analytical Biochemistry. vol. 218:87-91 (1994).

Seltsam, et al., Systematic analysis of the ABO gene diversity within exons 6 and 7 by PCR screening reveals new ABO alleles, Transfusion, vol. 43, pp. 428-439 (2003).

(56) References Cited

OTHER PUBLICATIONS

Sennerfors, T., et al., "Adsorption of Polyelectrolyte-Nanoparticle Systems on Silica: Influence of Ionic Strength". Journal of Colloid and Interface Science, vol. 254, pp. 222-226 (2002).
Serizawa, T., et al., "Electrostatic Adsorption of Polystyrene Nanospheres onto the Surface of an Ultrathin Polymer Film prepared by Using an Alternate Adsorption Technique". Langmuir, vol. 14, pp. 4088-4094 (1998).
Sethu, P; "Microfluidic diffusive filter for apheresis (leukopheresis)"; Lab Chip, vol. 6, No. 1, pp. 83-89 (Jan. 2006); Published electronically Nov. 11, 2005.
Seul et al., "Domain Shapes and Patterns: The Phenomenology of Modulated Phases". Science, vol. 267:476-483 (1995).
Seul et al., "Scale transformation of magnetic bubble arrays: coupling of topological disorder and polydispersity". Science, vol. 262: 558-560 (1993).
Sgaramella, V., et al., "Total Synthesis of the Structural Gene for an Alanine Transfer RNA from Yeast. Enzymic Joining of the Chemically Synthesized Polydeoxynucleotides to form the DNA Duplex Representing Nucleotide Sequence 1 to 20". J. Mol. Biology, vol. 72, pp. 427-444 (1972).
Sham, P. et al., "Haplotype Association of Discrete and Continuous Traits Using Mixture of Regression Models", Behavior Genetics, Mar. 2004, 34(2), pp. 207-214.
Shevkoplyas, S., et al., "Biomimetic autoseparation of leukocytes from whole blood in a microfluidic device"; American Chemical Society; vol. 77, No. 3, pp. 933-937 (Feb. 1, 2005).
Shon. "Application Note—New Best Practices for Biosample Management: Moving Beyond Freezers". American Biotechnology Laboratory, vol. 23, No. 2, pp. 10-13 (2005).
Shoyer, Terrie W., et al., "A Rapid Flow Cytometry Assay for HLA Antibody Detection Using a Pooled Cell Panel Convering 14 Serological Crossreacting Groups". Transplantation, vol. 59, No. 4, pp. 626-630 (1995).
Siegel, D., "Phage display-based molecular methods in immunohematology". Transfusion, vol. 47, pp. 89S-94S (Jul. 2007 Supplement).
Simon, R. "Application of optimization methods to the hematological support of patients with disseminated malignacies", Mathematical Biosciences, vol. 25, 1975, pp. 125-138.
Skalnik et al., "A Rapid Method for Characterizing transgenic Mice", S. Biotechniques 8:34 (1990).
Skolnick et al. "Simultaneous analysis of multiple polymorphic loci using amplified sequence polymorphisms (ASPs)". Genomics, vol. 2, pp. 273-279 (1988).
Smay, J., et al., "Colloidal Inks for Directed Assembly of 3-D Peridoic Structures". Langmuir, vol. 18, pp. 5429-5437 (2002).
Smith, J. W., et al., "RED: A Red-Cell Antibody Identification Expert Module". Journal of Medical Systems, vol. 9, No. 3, pp. 121-138 (1985).
Southern E. M., "DNA Fingerprinting by hybridisation to oligonucleotide arrays". Electrophoresis, vol. 16, No. 9, pp. 1539-1542 (1995).
Southern, E. M., et al., "Analyzing and comparing nucleic acid sequences by hybridization to arrays of oligonucleotides: evaluation using experimental models". vol. 13, No. 4, pp. 1008-1017 (Aug. 1992).
St. Louis, M, et al., "The Dombrock blood group system: A Review", Transfusion 43: 1126-1132 (2003).
Steemers, F.J. (2000) Screening unlabeled DNA targets with randomly ordered fiber-optic gene arrays. Nat. Biotechnol, 18, 91-94.
Stemmer, C., et al., "Use of Magnetic Beads for Plasma Cell-free DNA Extraction: Toward Automation of Plasma DNA Analysis for Molecular Diagnostics". Clinical Chemistry, vol. 49, No. 11, pp. 1953-1955 (2003).
Stevens, P. W., et al. "Imaging and Analysis of Immobilized Particle Arrays". Analytical Chemistry. vol. 75, pp. 1147-1154 (2003).
Storry et al, "Genetic Basis of blood group diversity". British Journal of Haematology, vol. 126, pp. 759-771 (2004).
Strobel E., et al., "The molecular basis of Rhesus antigen E", Transfusion 44:407-409 (2004).
Sukhishvili, S.A. et al. "Adsorption of human serum albumin: Dependence on molecular architecture of the oppositely charged surface" J. Chem. Phys. 110, 10153-10161 (1999).
Sun et al., "Continuous, Flow-Through Immunomagnetic Cell Sorting in a Quadrupole Field". Cytometry, vol. 33, pp. 469-475 (1998).
Suzawa et al., "Adsorption of Plasma Proteins onto Polymer Latices". Advances in Colloid and Interface Science, vol. 35, pp. 139-172 (1991).
Svitel, et al., "Combined Affinity and Rate Constant Distributions of Ligand Populations from Experimental Surface Binding Kinetics and Equilibria". Biophysical Journal, vol. 84, pp. 4062-4077 (Jun. 2003).
Syvanen, "From Gels to Chips: Minisequencing Primer Extensions for Analysis of Pont Mutations and Single Nucelotide Polymorphisms", Human Mutation 13:1-10 (1999).
Syvanen, A., et al., "Identification of Individuals by Analysis of Biallelic DNA Markers, Using PCR and Solid-Phase Minisequencing". Am. J. Hum. Genet, vol. 52, pp. 46-59 (1993).
Syvannen, A. "Toward genone-wide SNP genotyping". Nature Genetics Supplement. vol. 37: s5-s10 (2005).
Sze. MIS Diode and Charge-Coupled Device. The Physics of Semiconductors, Chapter 7, pp. 362-430 (2nd Edition) (1981).
Takeda et al. "Conformational Change of Bovine Serum Albumin by Heat Treatment", J. Protein Chemistry 8:653-659, No. 5 (1989).
Tanaka, T., et al., "Mechanical instability of gels at the phase transition", Nature, vol. 325, pp. 796-798 (1987).
Taniguchi et al. "Adsorption/desorption behavior and covalent grafting of an antibody onto cationic amino-functionalized poly(styrene-N-isoprapylacrylamide) core-shell latex particles". Colloids and Surfaces B: Biointerfaces. vol. 29: 53-65 (2003).
Tarnok et al., "Cytometric Bead Array to Measure Six Cytokines in Twenty-Five Microliters of Serum," Clinical Chemistry, (2003), vol. 49, No. 6, pp. 1000-1002.
Taylor et al., "Linked oligodeoxynucleotides show binding cooperativity and can selectively impair replication of deleted mitochondrial DNA templates", Nucleic Acids Research. vol. 29, No. 16, pp. 3404-3412 (2001).
Tobitani et al. "Heat-induced gelation of globular proteins. 1. Model for the effects of time and temperature onthe gelation time of BSA gels." Macromolecules. vol. 30:4845-4854 (1997).
Tokumasu F. et al., Development and application of quantum dots for immunocytochemistry of human erythrocytes, J. Microscopy, 2003, pp. 256-261, vol. 211, pt. 3.
Tonisson et al., "Arrayed primer extension on the DNA chip; Method and applications", Microarray Biochip Technology, Biotechniques Books, 247-262 (2000).
Tsuchihashi, Z. et al. "Progress in high throughput SNP genotyping methods", The Pharmacogenomics Journal 2:103-110 (Apr. 2002).
Trau et al., "Field-induced layering of colloidal crystal", Science, vol. 272; pp. 706-709 (1996).
Trang D.T.X. et al. "One step concentration of malarial parasite-infected red blood cells and removal of contaminating white blood cells", Malaria Journal (2004) pp. 1-7 from http://www.malariajournal.com/content/3/1/7.
Trau et al., "Nanoencapsulated microcrystalline particles for superamplified biochemical assays". Anal. Chem, vol. 74, No. 21, pp. 5480-5486. Web Release Date: Sep. 25, 2002.
Turcanu et al, "Cell Identification and isolation on the basis of cytokine secretion: A novel tool for investigating immune responses". Nature Medicine, vol. 7, No. 3, pp. 373-376 (Mar. 2001).
Tyagi et al., Molecular Beacons: Probes that Flouresce upon Hybridization, Nature Biotechnology vol. 14, pp. 303-308 (1996).
Vainrub, A., et al., "Sensitive quantitative nucleic acid detection using oligonucleotide microarrays". Journal of the American Chemical Society, vol. 125, No. 26, pp. 7798-7799, (Jun. 2003).
Van Kempen, et al., "Mean and Variance of Ratio Estimators Used in Fluorescence Ratio Imaging". Cytometry, vol. 39, pp. 300-305 (2000).
Van Zoelen, "Receptor-ligan interaction: a new method for determing binding parameters without a priori assumptions on non-specific binding". Biochem J., vol. 262, pp. 549-556 (1989).

(56) References Cited

OTHER PUBLICATIONS

Vasiliskov, A. V., et al., "Fabrication of Microarray of Gel-Immobilized Compounds on a Chip by Copolymerization". BioTechniques, vol. 27, pp. 592-606 (Sep. 1999).

Vaynberg et al. "Structure and extent of absorbed gelatin on acrylic latex and polystyrene collodial particles". Journal of Colloid and Interface Science. vol. 205:131-140 (1998).

Vet, J.A.M. (1999) Multiplex detection of four pathogenic retroviruses using molecular beacon. Proc. Natl. Acad. Sci. USA, 96, 6394-6399.

Vilain. "CYPs, SNPs, and Molecular Diagnosis in the Postgenomic Era". Clinical Chemistry, vol. 44, pp. 2403-2404 (1998).

Wahl et al., "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).

Wang, D., et al, "Large-Scale Identification, Mapping, and Genotyping of Single-Nucleotide Polymorphisms in the Human Genome". Science, vol. 280, No. 5366, pp. 1077-1082 (May 15, 1998).

Warren, J. A., "Selected Spacings During Directional Solidification of a Binary Alloy", Spatio-Temporal Patterns, Ed. P. E., Cladis and P. Palffy-Muhoray, SFI Studies in the Science of Complexity, Addison-Wesley, pp. 91-105 (1995).

Weinfeld et al., "Selective hydrolysis by exo- and endonucleases of phosphodiester bonds adjacent to an apurinic site". Nucleic Acids Research, vol. 17, No. 10: 3735-3744 (1989).

Weissenbach et al. "A Second generation linkage map of the human genome". Nature, vol. 359, pp. 794-801 (1992).

Wen, et al., "Planar Magnetic Colloidal Crystals". Physical Review Letters, vol. 85, No. 25, pp. 5464-5467 (2000).

Wiedmann, M., et al., Ligase Chain Reaction (LCR)—Overview and Applications, PCR Methods and Applications, Genome Research, vol. 3, pp. s51-s64 (1994).

Yeang et. al. Molecular classification of multiple tumor types. Bioinformatics vol. 17 Suppl. 1, pp. s316-s322 (2001).

J.F. Chapman et al., "Working Party of the BCSH:" Guidelines for compatibility procedures in blood transfusion laboratories, Transfusion Medicine, vol. 14, pp. 59-73 (2004).

Yamashita et al., "Thermodynamics for the preparation of micron-sized, monodispersed highly monomer absorbed polymer particles utilizing the dynamic selling method". Colloids and Surfaces, vol. 153, pp. 153-159 (1999).

Yao et al., "Molecular-beacon-based array for sensitive DNA analysis". Analytical Biochemistry, vol. 331, pp. 216-223 (2004).

Fukuda et al., "Noncontact manipulation of DNA molecule 1. Transportation of DNA molecule by dielectric force". Nippon Kikai Gakkai Ronbunshu, vol. 62: 2765-2772 (1996).

Hermanson, Greg T., "Zero Length Cross-Linkers"; Bioconjugate Techniques; Academic Press, pp. 170-176 (1996).

Hermanson, Greg T., "Bioconjugate Techniques", Bioconjugate Techniques; Academic Press, San Diego, 430-33, (1996).

MacBeath et al., "Printing proteins as microarrays for high-throughput function determination," Science vol. 289: 1760-1763 (2000).

Tobitani et al. "Heat-induced gelation of globular proteins 2. Effect of environmental factors on single-component and mixed-protein gels," Macromolecules; vol. 30: 4855-4862 (1997).

Wittemann et al., "Interaction of Proteins with Spherical Polyelectrolyte Brushes" (Polyer Institute, University of Karisruhe, Karisruhe, Germany) Poster Oct. 2001.

Hogue et al., "Extraction of DNA from Serum for High-Throughput Genotyping: Findings from Pilot Studies Within the Prostate Cancer Prevention Trial," Basic and Translational Science, Urology 71 (5), pp. 967-970 (2008).

FIG. 1A
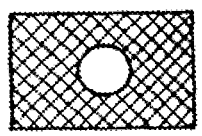
FIG. 1B
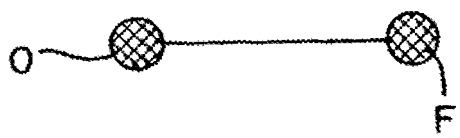
FIG. 1C
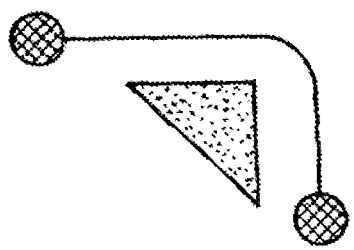
FIG. 1D
FIG. 1E
FIG. 1F
FIG. 1G
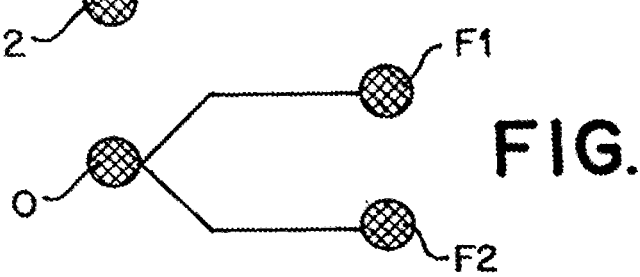
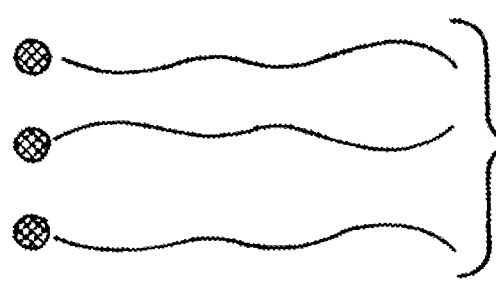
FIG. 1H

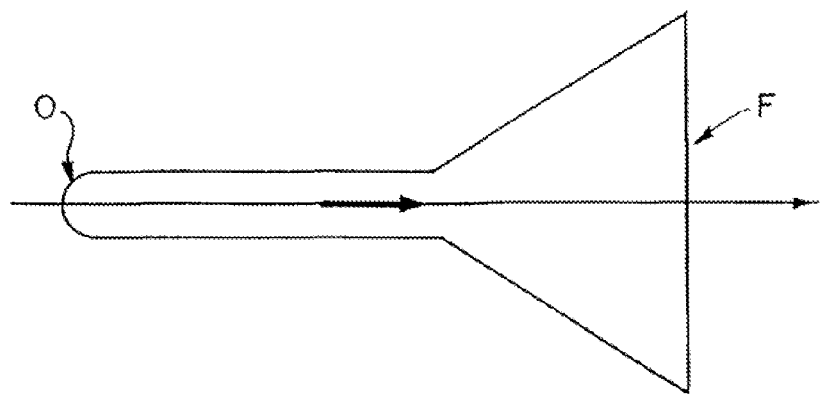
FIG. 3A
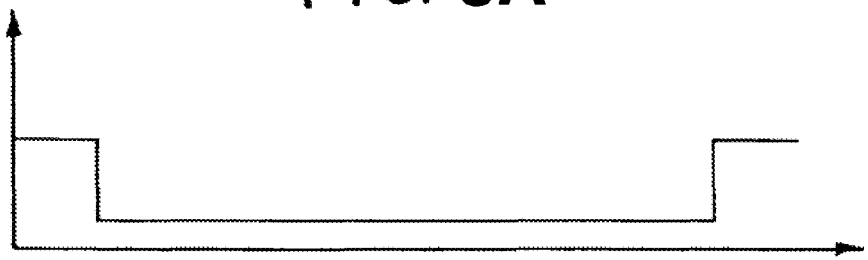
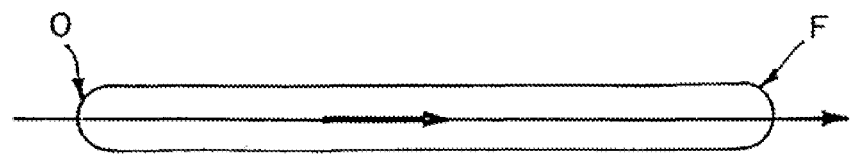
FIG. 3B
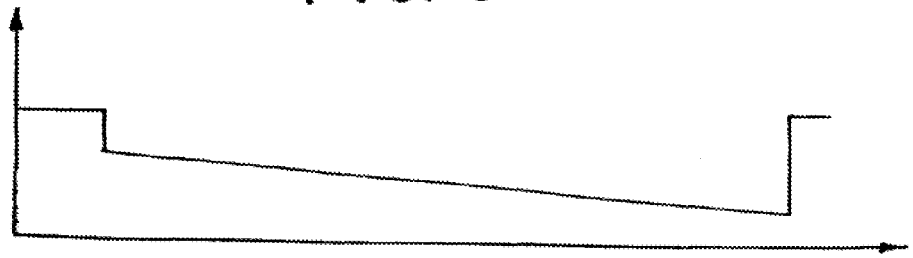

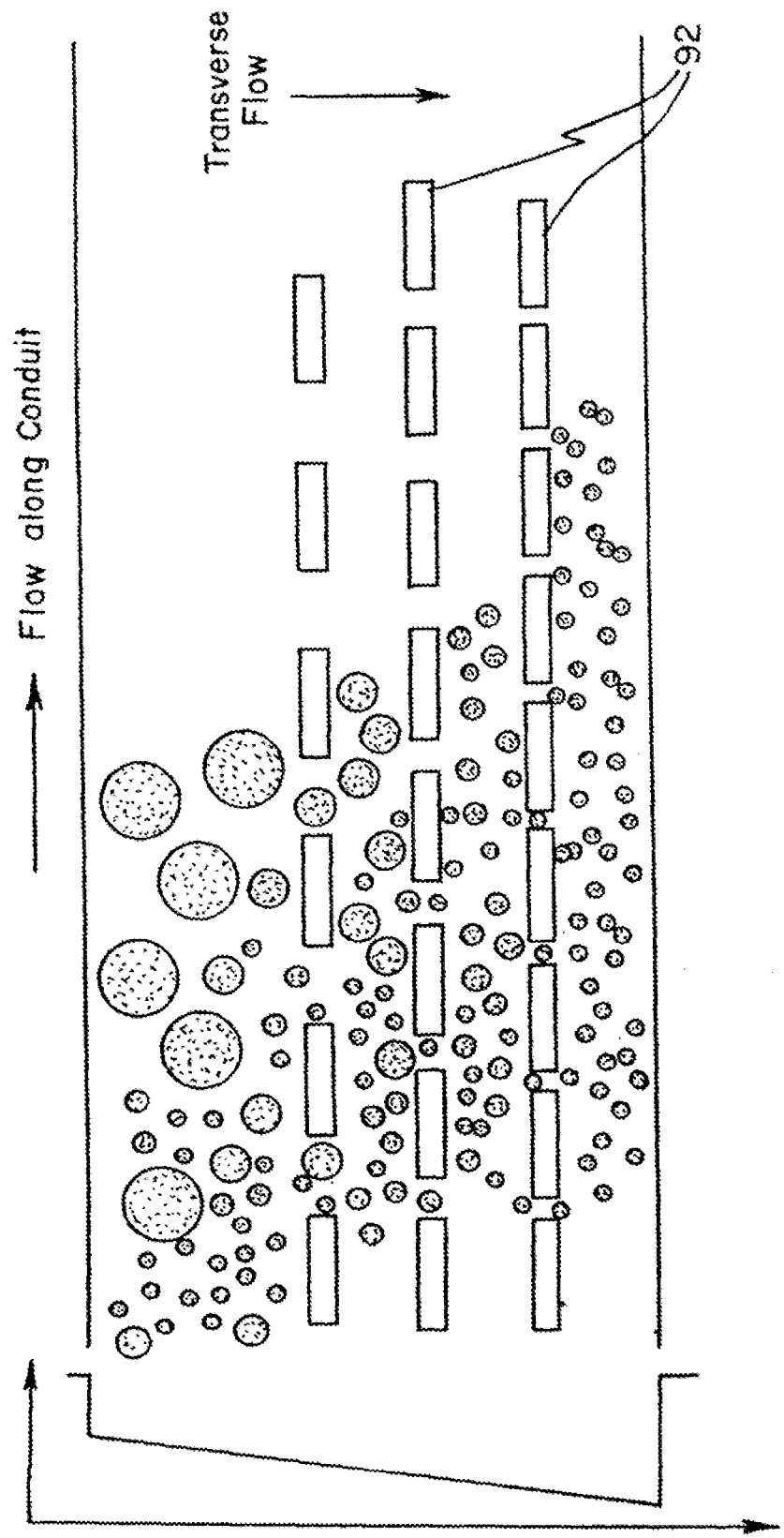

Illuminated Zone
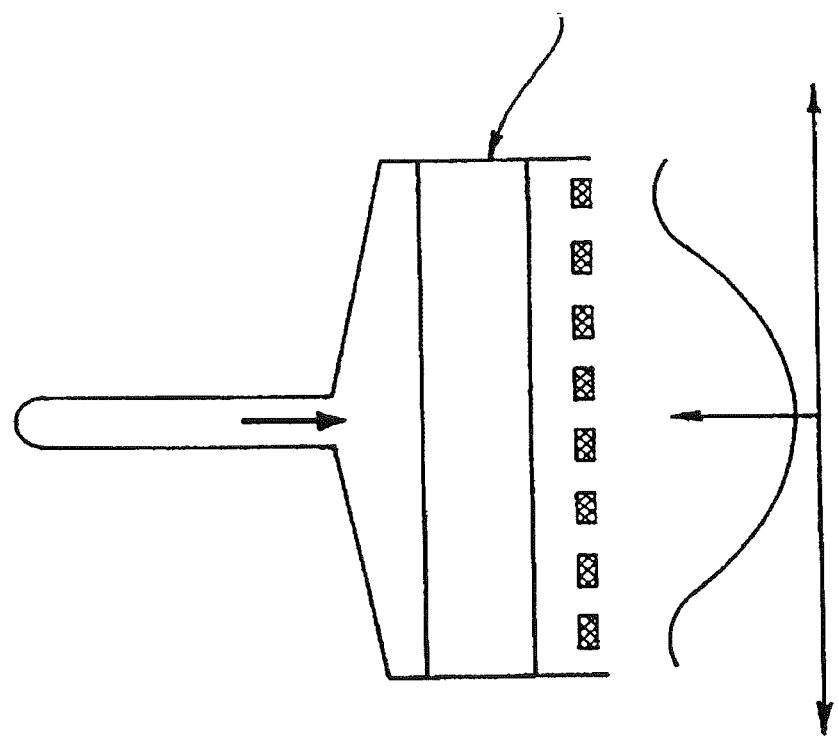
Oxide Profile
FIG. 9B

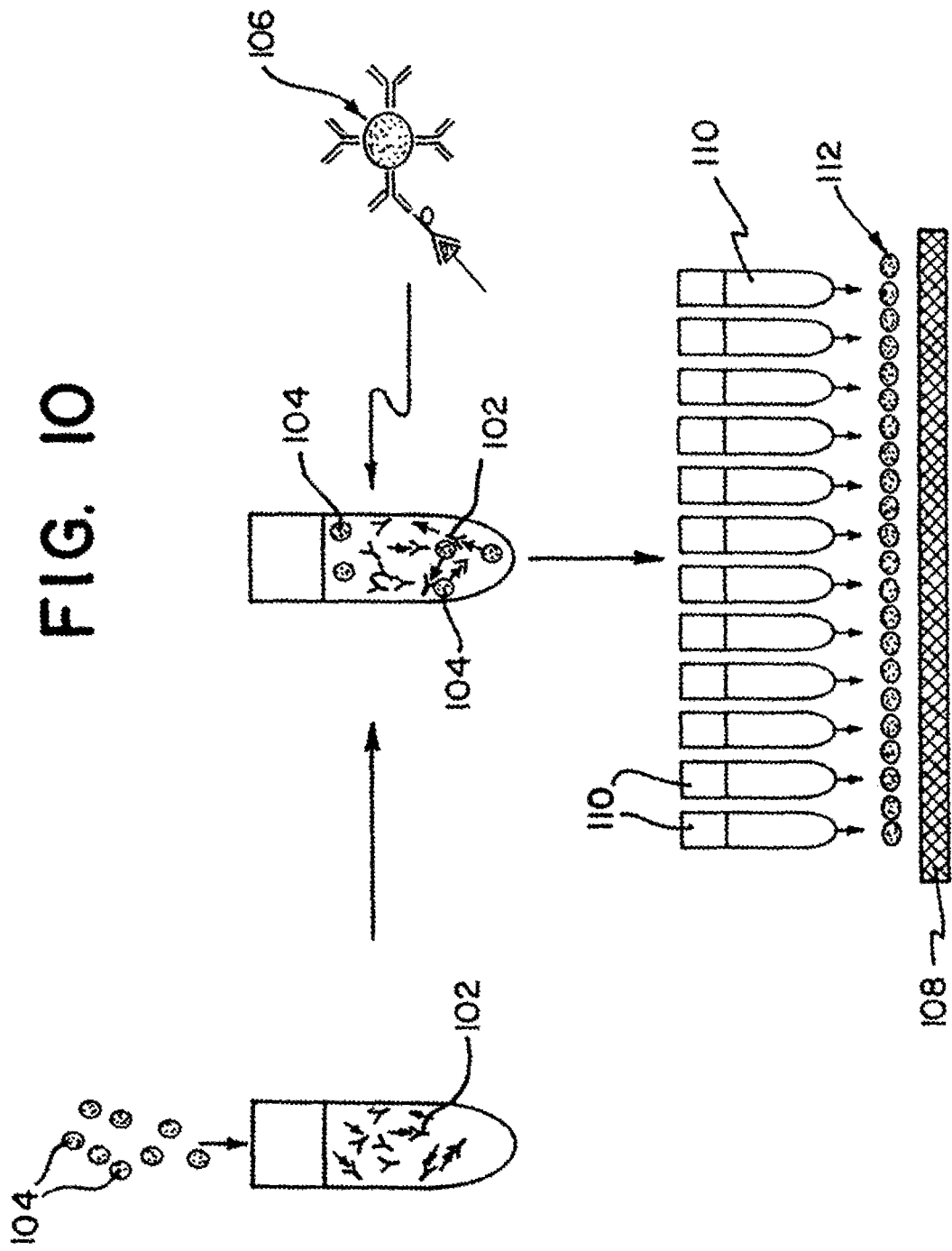

METHOD OF MAKING A MICROBEAD ARRAY WITH ATTACHED BIOMOLECULES

CROSS-REFERENCE TO RELATED APPLICATIONS

This application is a continuation of U.S. application Ser. No. 13/664,953 filed Oct. 31, 2012, (now U.S. Pat. No. 8,691, 594) which is a continuation of U.S. application Ser. No. 11/760,814, filed Jun. 11, 2007 (now U.S. Pat. No. 8,309, 368), which is a continuation of U.S. application Ser. No. 10/910,466, filed Aug. 3, 2004 (now U.S. Pat. No. 7,427,512), which is a continuation of U.S. application Ser. No. 09/690, 040, filed Oct. 17, 2000 (now U.S. Pat. No. 6,797,524), which is a continuation of U.S. application Ser. No. 09/171,550, filed Oct. 26, 1998 (now U.S. Pat. No. 6,251,691), which is a 35 U.S.C. Section 371 national stage entry of PCT/US97/08159, filed Apr. 24, 1997, which claims priority to U.S. Provisional Application No. 60/016,642, filed Apr. 25, 1996. All of the applications and patents cited above are hereby incorporated by reference in their entireties.

FIELD OF THE INVENTION

The present invention generally relates to the field of materials science and analytical chemistry.

The present invention specifically relates to the realization of a complete, functionally integrated system for the implementation of biochemical analysis in a planar, miniaturized format on the surface of a conductive and/or photoconductive substrate, with applications in pharmaceutical and agricultural drug discovery and in in-vitro or genomic diagnostics. In addition, the method and apparatus of the present invention may be used to create material surfaces exhibiting desirable topographical relief and chemical functionality, and to fabricate surface-mounted optical elements such as lens arrays.

BACKGROUND OF THE INVENTION

I—Ions, Electric Fields, and Fluid Flow: Field-Induced Formation of Planar Bead Arrays Electrokinesis refers to a class of phenomena elicited by the action of an electric field on the mobile ions surrounding charged objects in an electrolyte solution. When an object of given surface charge is immersed in a solution containing ions, a diffuse ion cloud forms to screen the object's surface charge. This arrangement of a layer of (immobile) charges associated with an immersed object and the screening cloud of (mobile) counterions in solution is referred to as a "double layer". In this region of small but finite thickness, the fluid is not electroneutral. Consequently, electric fields acting on this region will set in motion ions in the diffuse layer, and these will in turn entrain the surrounding fluid. The resulting flow fields reflect the spatial distribution of ionic current in the fluid. Electroosmosis represents the simplest example of an electrokinetic phenomenon. It arises when an electric field is applied parallel to the surface of a sample container or electrode exhibiting fixed surface charges, as in the case of a silicon oxide electrode (in the range of neutral pH). As counterions in the electrode double layer are accelerated by the electric field, they drag along solvent molecules and set up bulk fluid flow. This effect can be very substantial in narrow capillaries and may be used to advantage to devise fluid pumping systems.

Electrophoresis is a related phenomenon which refers to the field-induced transport of charged particles immersed in an electrolyte. As with electroosmosis, an electric field accelerates mobile ions in the double layer of the particle. If, in contrast to the earlier case, the particle itself is mobile, it will compensate for this field-induced motion of ions (and the resulting ionic current) by moving in the opposite direction. Electrophoresis plays an important role in industrial coating processes and, along with electroosmosis, it is of particular interest in connection with the development of capillary electrophoresis into a mainstay of modern bioanalytical separation technology.

In confined geometries, such as that of a shallow experimental chamber in the form of a "sandwich" of two planar electrodes, the surface charge distribution and topography of the bounding electrode surfaces play a particularly important role in determining the nature and spatial structure of electroosmotic flow. Such a "sandwich" electrochemical cell may be formed by a pair of electrodes separated by a shallow gap. Typically, the bottom electrode will be formed by an oxide-capped silicon wafer, while the other electrode is formed by optically transparent, conducting indium tin oxide (ITO). The silicon (Si) wafer represents a thin slice of a single crystal of silicon which is doped to attain suitable levels of electrical conductivity and insulated from the electrolyte solution by a thin layer of silicon oxide (SiOx).

The reversible aggregation of beads into planar aggregates adjacent to an electrode surface may be induced by a (DC or AC) electric field that is applied normal to the electrode surface. While the phenomenon has been previously observed in a cell formed by a pair of conductive ITO electrodes (Richetti, Prost and Barois, J. Physique Lettr. 45, L-1137 through L-1143 (1984)), the contents of which are incorporated herein by reference, it has been only recently demonstrated that the underlying attractive interaction between beads is mediated by electrokinetic flow (Yeh, Seul and Shraiman, "Assembly of Ordered Colloidal Aggregates by Electric Field Induced Fluid Flow", Nature 386, 57-59 (1997), the contents of which are incorporated herein by reference. This flow reflects the action of lateral non-uniformities in the spatial distribution of the current in the vicinity of the electrode. In the simplest case, such non-uniformities are introduced by the very presence of a colloidal bead near the electrode as a result of the fact that each bead interferes with the motion of ions in the electrolyte. Thus, it has been observed that an individual bead, when placed near the electrode surface, generates a toroidal flow of fluid centered on the bead. Spatial non-uniformities in the properties of the electrode can also be introduced deliberately by several methods to produce lateral fluid flow toward regions of low impedance. These methods are described in subsequent sections below.

Particles embedded in the electrokinetic flow are adverted regardless of their specific chemical or biological nature, while simultaneously altering the flow field. As a result, the electric field-induced assembly of planar aggregates and arrays applies to such diverse particles as: colloidal polymer lattices ("latex beads"), lipid vesicles, whole chromosomes, cells and biomolecules including proteins and DNA, as well as metal or semiconductor colloids and clusters.

Important for the applications to be described is the fact that the flow-mediated attractive interaction between beads extends to distances far exceeding the characteristic bead dimension. Planar aggregates are formed in response to an externally applied electric field and disassemble when the field is removed. The strength of the applied field determines the strength of the attractive interaction that underlies the array assembly process and thereby selects the specific arrangement adopted by the beads within the array. That is, as a function of increasing applied voltage, beads first form planar aggregates in which particles are mobile and loosely packed, then assume a tighter packing, and finally exhibit a spatial arrangement in the form of a crystalline, or ordered, array resembling a raft of bubbles. The sequence of transitions between states of increasing internal order is reversible, including complete disassembly of planar aggregates when the applied voltage is removed. In another arrangement, at low initial concentration, beads form small clusters which in turn assume positions within an ordered "superstructure".

II—Patterning of Silicon Oxide Electrode Surfaces

Electrode patterning in accordance with a predetermined design facilitates the quasi-permanent modification of the electrical impedance of the EIS (Electrolyte-Insulator-Semiconductor) structure of interest here. By spatially modulating the EIS impedance, electrode-patterning determines the ionic current in the vicinity of the electrode. Depending on the frequency of the applied electric field, beads either seek out, or avoid, regions of high ionic current. Spatial patterning therefore conveys explicit external control over the placement and shape of bead arrays.

While patterning may be achieved in many ways, two procedures offer particular advantages. First, UV-mediated re-growth of a thin oxide layer on a properly prepared silicon surface is a convenient methodology that avoids photolithographic resist patterning and etching. In the presence of oxygen, UV illumination mediates the conversion of exposed silicon into oxide. Specifically, the thickness of the oxide layer depends on the exposure time and may thus be spatially modulated by placing patterned masks into the UV illumination path. This modulation in thickness, with typical variations of approximately 10 Angstroms, translates into spatial modulations in the impedance of the Si/SiOx interface while leaving a flat and chemically homogeneous top surface exposed to the electrolyte solution. Second, spatial modulations in the distribution of the electrode surface charge may be produced by UV-mediated photochemical oxidation of a suitable chemical species that is first deposited as a monolayer film on the SiOx surface. This method permits fine control over local features of the electrode double layer and thus over the electrokinetic flow.

A variation of this photochemical modulation is the creation of lateral gradients in the EIS impedance and hence in the current generated in response to the applied electric field. For example, this is readily accomplished by controlling the UV exposure so as to introduce a slow lateral variation in the oxide thickness or in the surface charge density. As discussed below, control over lateral gradients serves to induce lateral bead transport and facilitates the implementation of such fundamental operations as capturing and channeling of beads to a predetermined destination along conduits in the form of impedance features embedded in the Si/SiOx interface. Photochemical patterning of functionalized chemical overlayers also applies to other types of electrode surfaces including ITO.

III—Light-Controlled Modulation of the Interfacial Impedance

The spatial and temporal modulation of the EIS-impedance in accordance with a pattern of external illumination provides the basis to control the electrokinetic forces that mediate bead aggregation. The light-modulated electrokinetic assembly of planar colloidal arrays facilitates remote interactive control over the formation, placement and rearrangement of bead arrays in response to corresponding illumination patterns and thereby offers a wide range of interactive manipulations of colloidal beads and biomolecules.

To understand the principle of this methodology, it will be helpful to briefly review pertinent photoelectric properties of semiconductors, or more specifically, those of the EIS structure formed by the Electrolyte solution (E), the Insulating SiOx layer (I) and the Semiconductor (S). The photoelectric characteristics of this structure are closely related to those of a standard Metal-Insulator-Semiconductor (MIS) or Metal-Oxide-Semiconductor (MOS) devices which are described in S. M. Sze, "The Physics of Semiconductors", 2nd Edition, Chapt. 7 (Wiley Interscience 1981), the contents of which art incorporated herein by reference.

The interface between the semiconductor and the insulating oxide layer deserves special attention. Crucial to the understanding of the electrical response of the MOS structure to light is the concept of a space charge region of small but finite thickness that forms at the Si/SiOx interface in the presence of a bias potential. In the case of the EIS structure, an effective bias, in the form of a junction potential, is present under all but very special conditions. The space charge region forms in response to the distortion of the semiconductor's valence and conduction bands ("band bending") in the vicinity of the interface. This condition in turn reflects the fact that, while there is a bias potential across the interface, there is ideally no charge transfer in the presence of the insulating oxide. That is, in electrochemical language, the EIS structure eliminates Faradaic effects. Instead, charges of opposite sign accumulate on either side of the insulating oxide layer and generate a finite polarization.

In the presence of a reverse bias, the valence and conduction band edges of an n-doped semiconductor bend upward near the Si/SiOx interface and elections flow out of the interfacial region in response to the corresponding potential gradient. As a result, a majority carrier depletion layer is formed in the vicinity of the Si/SiOx interface. Light absorption in the semiconductor provides a mechanism to create electron-hole pairs within this region. Provided that they do not instantaneously recombine, electron-hole pairs are split by the locally acting electric field, and a corresponding photocurrent flows. It is this latter effect that affords control over the electrokinetic assembly of beads in the electrolyte solution.

To understand in more detail the pertinent frequency dependence of the light-induced modulation of the EIS impedance, two aspects of the equivalent circuit representing the EIS structure are noteworthy. First, there are close analogies between the detailed electrical characteristics of the electric double layer at the electrolyte-oxide interface, and the depletion layer at the interface between the semiconductor and the insulator. As with the double layer, the depletion layer exhibits electrical characteristics similar to those of a capacitor with a voltage-dependent capacitance. As discussed, illumination serves to lower the impedance of the depletion layer. Second, given its capacitive electrical response, the oxide layer will pass current only above a characteristic ("threshold") frequency. Consequently, provided that the frequency of the applied voltage exceeds the threshold, illumination can lower the effective impedance of the entire EIS structure.

This effective reduction of the EIS impedance also depends on the light intensity which determines the rate of generation of electron-hole pairs. In the absence of significant recombination, the majority of photogenerated electrons flow out of the depletion region and contribute to the photocurrent. The remaining hole charge accumulates near the Si/SiOx interface and screens the electric field acting in the depletion region. As a result, the rate of recombination increases, and the efficiency of electron-hole separation, and hence the photocurrent, decreases. For given values of frequency and amplitude of the applied voltage, one therefore expects that as the illumination intensity increases, the current initially increases to a maximum level and then decreases. Similarly, the impedance initially decreases to a minimum value (at maximum current) and then decreases.

This intensity may be used to advantage to induce the lateral displacement of beads between fully exposed and partially masked regions of the interface. As the illumination intensity is increased, the fully exposed regions will correspond to the regions of interface of lowest impedance, and hence of highest current, and beads will be drawn into these regions. As the fully exposed regions reach the state of decreasing photocurrent, the effective EIS impedance in those regions may exceed that of partially masked regions, with a resulting inversion of the lateral gradient in current. Beads will then be drawn out of the fully exposed regions. Additionally, time-varying changes in the illumination pattern may be used to effect bead motion.

IV—Integration of Biochemical Analysis in a Miniaturized, Planar Format

The implementation of assays in a planar array format, particularly in the context of biomolecular screening and medical diagnostics, has the advantage of a high degree of parallelity and automation so as to realize high throughput in complex, multi-step analytical protocols. Miniaturization will result in a decrease in pertinent mixing times reflecting the small spatial scale, as well as in a reduction of requisite sample and reagent volumes as well as power requirements. The integration of biochemical analytical techniques into a miniaturized system on the surface of a planar substrate ("chip") would yield substantial improvements in the performance, and reduction in cost, of analytical and diagnostic procedures.

Within the context of DNA manipulation and analysis, initial steps have been taken in this direction (i.e., miniaturization) by combining on a glass substrate, the restriction enzyme treatment of DNA and the subsequent separation of enzyme digests by capillary electrophoresis, see, for example, Ramsey, PCT Publication No. WO 96/04547, the contents of which are incorporated herein by reference, or the amplification of DNA sequences by application of the polymerase chain reaction (PCR) with subsequent electrophoretic separation, see, for example, U.S. Pat. Nos. 5,498,392 and 5,587,128 to Wilding et al., the contents of which are incorporated herein by reference.

While these standard laboratory processes have been demonstrated in a miniaturized format, they have not been used to form a complete system. A complete system will require additional manipulation such as front-end sample processing, binding and functional assays and the detection of small signals followed by information processing. The true challenge is that of complete functional integration because it is here that system architecture and design constraints on individual components will manifest themselves. For example, a fluidic process is required to concatenate analytical steps that require the spatial separation, and subsequent transport to new locations, of sets of analyte. Several possibilities have been considered including electroosmotic pumping and transport of droplets by temperature-induced gradients in local surface tension. While feasible in demonstration experiments, these techniques place rather severe requirements on the overall systems lay-out to handle the very considerable DC voltages required for efficient electroosmotic mixing or to restrict substrate heating when generating thermally generated surface tension gradients so as to avoid adverse effects on protein and other samples.

SUMMARY OF THE INVENTION

The present invention combines three separate functional elements to provide a method and apparatus facilitating the real-time, interactive spatial manipulation of colloidal particles ("beads") and molecules at an interface between a light sensitive electrode and an electrolyte solution. The three functional elements are: the electric field-induced assembly of planar particle arrays at an interface between an insulating or a conductive electrode and an electrolyte solution; the spatial modulation of the interfacial impedance by means of UV-mediated oxide regrowth or surface-chemical patterning; and, finally, the real-time, interactive control over the state of the interfacial impedance by light. The capabilities of the present invention originate in the fact that the spatial distribution of ionic currents, and thus the fluid flow mediating the array assembly, may be adjusted by external intervention. Of particular interest is the introduction of spatial non-uniformities in the properties of the pertinent EIS stricture. As described herein, such inhomogeneities, either permanent or temporary in nature, may be produced by taking advantage of the physical and chemical properties of the EIS structure.

The invention relates to the realization of a complete, functionally integrated system for the implementation of biochemical analysis in a planar, miniaturized format on the surface of a silicon wafer or similar substrate. In addition, the method and apparatus of the present invention may be used to create material surfaces exhibiting desirable topographical relief and chemical functionality, and to fabricate surface-mounted optical elements such as lens arrays.

The combination of three functional elements endows the present invention with a set of operational capabilities to manipulate beads and bead arrays in a planar geometry to allow the implementation of biochemical analytical techniques. These fundamental operations apply to aggregates and arrays of particles such as: colloidal polymer lattices, vesicles, whole chromosomes, cells and biomolecules including proteins and DNA, as well as metal or semiconductor colloids and clusters.

Sets of colloidal particles may be captured, and arrays may be formed in designated areas on the electrode surface (FIGS. 1a, 1b and FIGS. 2a-d). Particles, and the arrays they form in response to the applied field, may be channeled along conduits of any configuration that are either embedded in the Si/SiOx interface by UV-oxide patterning or delineated by an external pattern of illumination. This channeling (FIGS. 1c, 1d, 1e, FIGS. 3c, 3d), in a direction normal to that of the applied electric field, relies on lateral gradients in the impedance of the EIS structure and hence in the field-induced current. As discussed herein, such gradients may be introduced by appropriate patterns of illumination, and this provides the means to implement a gated version of translocation (FIG. 1e). The electroltinetic flow mediating the array assembly process may also be exploited for the alignment of elongated particles, such as DNA, near the surface of the electrode. In addition, the present invention permits the realization of methods to sort and separate particles.

Arrays of colloidal particles may be placed in designated areas and confined there until released or disassembled. The overall shape of the array may be delineated by UV-oxide patterning or, in real time, by shaping the pattern of illumination. This capability enables the definition of functionally distinct compartments, permanent or temporary, on the electrode surface. Arrays may be subjected to changes of shape imposed in real time, and they may be merged with other ways (FIG. 1f) or split into two or more subarrays or clusters (FIG. 1g, FIGS. 4a, 4b). In addition, the local state of order of the array as well as the lateral particle density may be reversibly adjusted by way of the external electric field or modified by addition of a second, chemically inert bead component.

The present invention also allows for the combination of fundamental operations to develop increasingly complex products and processes. Examples given herein describe the implementation of analytical procedures essential to a wide range of problems in materials science, pharmaceutical drug discovery, genomic mapping and sequencing technology. Important to the integration of these and other functionalities in a planar geometry is the capability, provided by the present invention, to impose temporary or permanent compartmentalization in order to spatially isolate concurrent processes or sequential steps in a protocol and the ability to manipulate sets of particles in a manner permitting the concatenation of analytical procedures that are performed in different designated areas on the substrate surfaces.

BRIEF DESCRIPTION OF DRAWINGS

Other objects, features and advantages of the invention discussed in the above brief explanation will be more clearly understood when taken together with the following detailed description of an embodiment which will be understood as being illustrative only, and the accompanying drawings reflecting aspects of that embodiment, in which:

FIGS. 1A-1H are illustrations of the fundamental operations for bead manipulation;

FIGS. 3A and 3B are illustrations of the oxide profile of an Si/SiOx electrode;

FIGS. 9A and 9B are illustrations of two mechanisms of particle sorting;

FIG. 10 is an illustration of a planar array of bead-anchored probe-target complexes.

DETAILED DESCRIPTION OF THE PREFERRED EMBODIMENTS

Figure 2A:
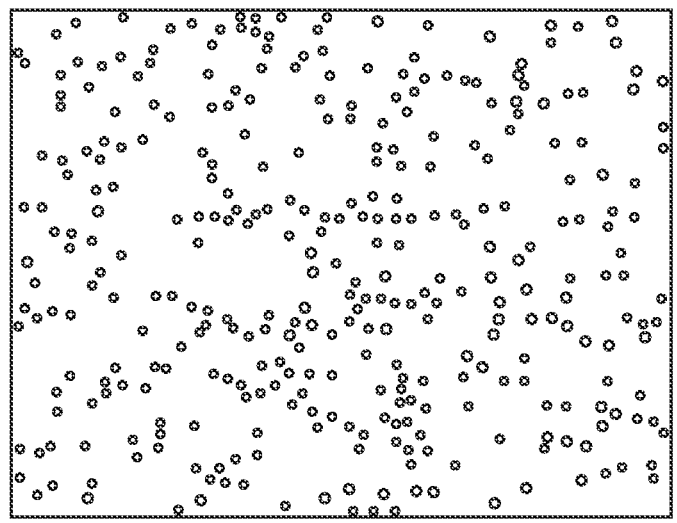
FIGS. 2A and 2B are photographs illustrating the process of capturing particles in designated areas on the substrate surface.

The three functional elements of the present invention may be combined so as to provide a set of fundamental operations for the interactive spatial manipulation of colloidal particles and molecules, assembled into planar aggregates adjacent to an electrode surface. In the following description, fundamental operations in this "toolset" are described in order of increasing complexity. Specifically, it is useful to adopt a classification scheme based on the total number of inputs and outputs, or "terminals", involved in a given operation. For example, the merging of two separate arrays, or sets of particles, into one would be a "three-terminal" operation, involving two inputs and one output. The converse three-terminal operation, involving one input and two outputs, is the splitting of a given array into two subarrays.

Experimental conditions yielding the phenomena depicted in the various photographs included herein are as follows. An electrochemical cell is formed by a pair of planar ITO electrodes, composed of an ITO layer deposited on a glass substrate, or by a Si/SiOx electrode on the bottom and an ITO electrode on the top, separated by a typical gap of 50 microns or less. Given its dependence on the photoelectric properties of the Si/SiOx interface, light control is predicated on the use of a Si/SiOx electrode. Leads, in the form of platinum wires, are attached to the ITO and to the silicon electrode, which is first etched to remove the insulating oxide in the contact region, by means of silver epoxy. The cell is first assembled and then filled, relying on capillary action, with a suspension of colloidal beads, 1 or 2 microns in diameter, at a typical concentration of 0.1% solids in 0.1 mM azide solution, corresponding to approximately $2 \times 10^8$ particles per milliliter. The number is chosen so as to yield between ½ and 1 full monolayer of particles on the electrode surface. Anionic (e.g., carboxylated polystyrene, cationic (e.g., aminated polystyrene) or nominally neutral (e.g., polystyrene) have all been used to demonstrate the basic phenomena underlying the three functional elements of the present invention. The silicon electrode was fabricated from a 1 inch-square portion of a Si (100) wafer, typically 200-250 microns thick, n-doped to typically 0.01 Ohm cm resistivity, and capped with a thin oxide of typically 30-40 Angstroms thickness. A thick oxide layer of typically 6000-8000 Angstrom thickness, grown under standard conditions in a furnace at 950 degrees C., may be etched by standard photolithography to define the structures of interest. Alternatively, a thin oxide layer may be regrown on a previously stripped surface of (100)-orientation under UV illumination. Given its ease of implementation and execution, UV-mediated oxide regrowth is the preferable technique: it provides the means to pattern the surface by placing a quartz mask representing the desired pattern in the path of UV illumination and it leaves a chemically homogeneous, topographically flat top surface. To avoid non-specific particle adsorption to the electrode surface, stringent conditions of cleanliness should be followed, such as those set forth in the General Experimental Conditions below.

Figure 2B:
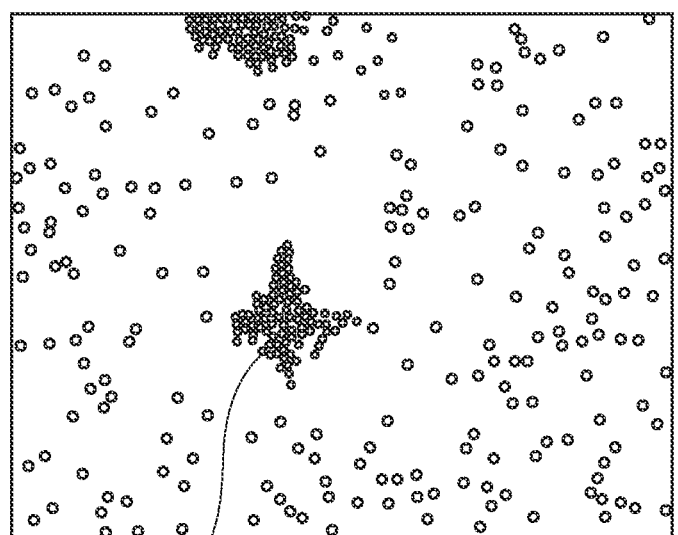
Figure 2C:
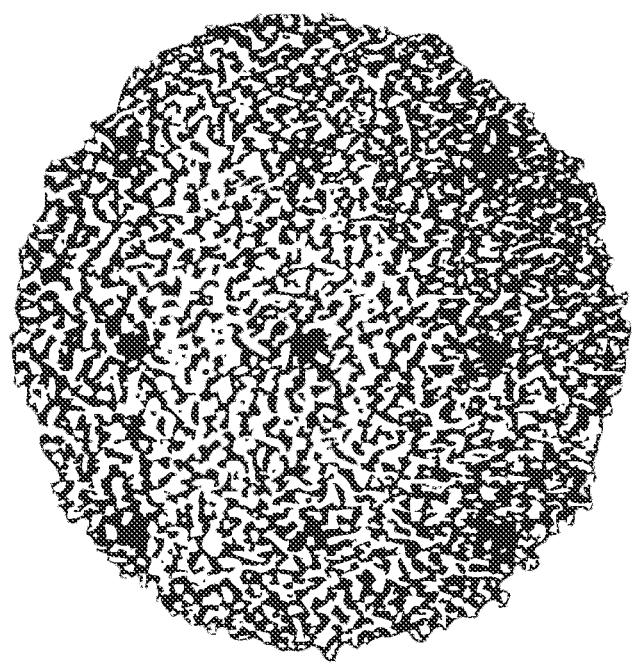
FIGS. 2C and 2D are photographs illustrating the process of excluding particles from designated areas on the substrate surface.

The fundamental one-terminal operation is a "capture-and-hold" operation (FIG. 1a) which forms an array of particles in a designated area of arbitrary outline on the surface that is delineated by UV-mediated oxide patterning or by a corresponding pattern of illumination projected on an otherwise uniform Si/SiOx substrate surface. FIGS. 2a and 2b illustrate bead capture on a surface characterized by a very thin oxide region 22 (approximately 20-30 Angstroms in thickness) and correspondingly low impedance, while the remaining surface is covered with the original, thick oxide with correspondingly high impedance. In FIG. 2a, there is no applied field, and hence, no bead capture. In contrast, in FIG. 2b, an electric field is applied (10 Vp-p source, 1 kHz) and bead capture occurs within the thin oxide region 22. Under these conditions, an array starts to grow within less than a second and continues to grow over the next approximately 10 seconds as beads arrive from increasingly larger distances to add to the outward growing perimeter of region 22. Growth stops when the array approaches the outer limit of the delineated target area, i.e., the area defined by the thin oxide having a low impedance. The internal state of order of the captured aggregate of beads is determined by the strength of the applied voltage, higher values favoring increasingly denser packing of beads and the eventual formation of ordered arrays displaying a hexagonally crystalline configuration in the form of a bubble raft. The array remains in place as long as the applied voltage is present. Removal of the applied voltage results in the disassembly of the array.

The "capture-and-hold" operation may also be implemented under illumination with visible or infrared light, for example by simply projecting a mask patterned with the desired layout onto the Si/SiOx electrode. A regular 100 W quartz microscope illuminator has been used for this purpose on a Zeiss UEM microscope, with apertures or masks inserted in the intermediate image plane to provide the required shape in the plane of the electrode (when focused properly under conditions of Koehler illumination). Alternatively, an IR laser diode with output of 3 mW at 650-680 nm also has been used. The use of external illumination rather than oxide patterning for the spatial confinement of particles allows the confinement pattern to be easily modified.

Figure 2D:
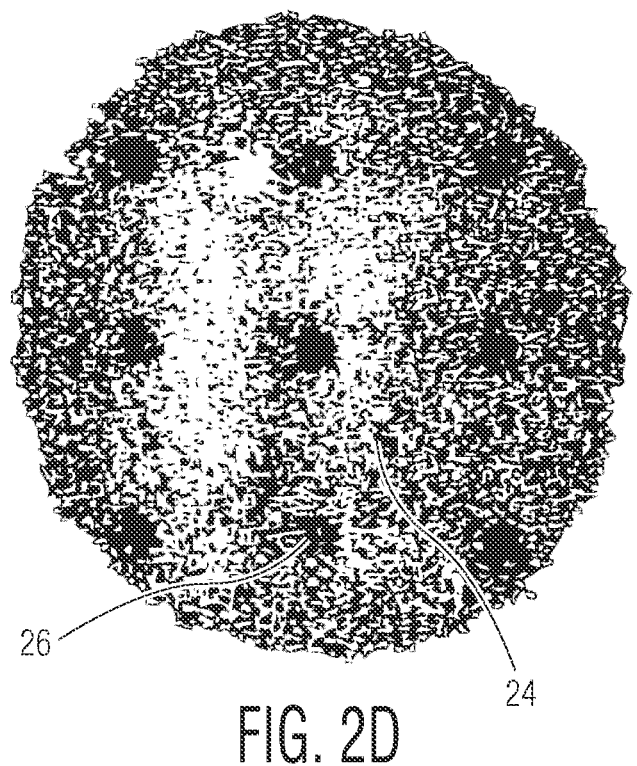

Related to "capture-and-hold" is the one-terminal operation of "exclude-and-hold" (FIG. 1b) which clears particles from a designated area on the surface. Increasing the frequency of the applied voltage to approximately 100 kHz leads to an inversion in the preference of particles which assemble is the thin-oxide portion of the surface (e.g., region 22, FIG. 2b) and instead form structures decorating the outside of the target area perimeter. Rather than relying on this effect, the exclusion of particles from the desired areas is also accomplished, in analogy to the original "capture-and-hold" operations, by simply embedding the corresponding structure in the Si/SiOx interface by UV-mediated oxide regrowth. In the example of FIGS. 2e and 2d, this is achieved, under conditions otherwise identical to those described above, with respect to FIGS. 2a and 2b, by applying 20V (pp) at 10 kHz. While the oxide thickness in the non designated areas 24 is approximately 30 Angstroms, the value in the designated square areas 26 is approximately 40 Angstroms, implying a correspondingly higher impedance at the applied frequency.

The "capture-and-hold" operation enables the spatial compartmentalization of the substrate surface into functionally distinct regions. For example, particles of distinct chemical type, introduced into the electrochemical cell at different times or injected in different locations, can be kept in spatially isolated locations by utilizing this operation.

The fundamental two-terminal operation is translocation (FIG. 1c), or the controlled transport of a set of particles from location O to location F on the surface; here, O and F are target areas to which the above-described one-terminal operations may be applied. The one-dimensional, lateral bead transport used in translocation is achieved by imposing a lateral current along a conduit connecting areas O and F, as shown in FIGS. 3a and 3b or by projecting a corresponding linear pattern of illumination. In this channeling operation, beads move in the direction of lower impedance in the direction of the arrow shown in FIGS. 3a and 3b, in accordance with the underlying electrokinetic flow.

Figure 3C:
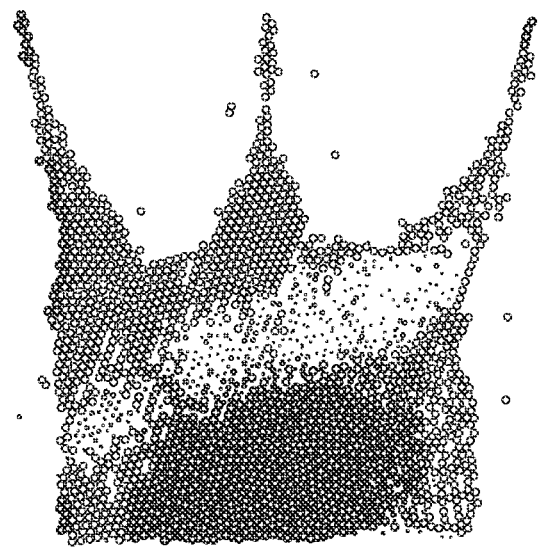
FIGS. 3C and 3D are photographs of the channeling of particles along conduits.
Figure 3D:

Oxide patterning may be utilized in two ways to create a lateral current along the Si/SiOx interface. The simplest method is depicted in FIG. 3c and shows a large open holding area 32 fed by three narrow conduits 34 defined by etching a thermal oxide. Beads move to the holding area 32 along the narrow conduits 34 to form a bead array. FIG. 3d is a large scale view of the array of FIG. 3c. The principle invoked in creating transport is that of changing the aspect ratio (narrow conduit connected to wide holding area) of the embedded pattern with constant values of thin oxide thickness inside and thick oxide outside, as illustrated in FIG. 3a. In FIGS. 3c and 3d, the applied voltage was 10V (pp) at 10 kHz. An alternative approach for creating bead transport, enabled by UV-mediated oxide regrowth, is to vary the oxide thickness along the conduit in a controlled fashion. This is readily accomplished by UV exposure through a graduated filter. Differences in the oxide thickness between O and F of as little as 5-10 Angstroms suffice to effect lateral transport. In this situation, the aspect ratio of the conduit and holding areas need not be altered. This is illustrated in FIG. 3b.

The use of external illumination to define conduits, by varying the illumination intensity along the conduit to create the requisite impedance gradient, has the advantage that the conduit is only a temporary structure, and that the direction of motion may be modified or reversed if so desired. The present invention provides for mechanisms of light-mediated active linear transport of planar aggregates of beads under interactive control. This is achieved by adjusting an external pattern of illumination in real time, either by moving the pattern across the substrate surface in such a way as to entrain the illuminated bead array or by electronically modulating the shape of the pattern to induce motion of particles.

Two modes of light-mediated, active transport are:

i) Direct Translocation ("tractor beam") which is a method of translocating arrays and of delineating their overall shape by adjusting parameters so as to favor particle assembly within illuminated areas of the surface, as described herein. Arrays simply follow the imposed pattern. The rate of motion is limited by the mobility of particles in the fluid and thus depends on particle diameter and fluid viscosity.

ii) Transverse Array Constriction is a bead transport mechanism related to peristaltic pumping of fluids through flexible tubing. The light-control component of the present invention may be used for a simple implementation of this very general concept. A multi-component planar aggregate of beads is confined to a rectangular channel, by UV-patterning if so desired, or simply by light. Beads are free to move along the channel by diffusion (in either direction). An illumination pattern matching the transverse channel dimension is set up and is then varied in time so as to produce a transverse constriction wave that travels in one direction along the channel. Such a constriction wave may be set up in several ways. A conceptually simple method is to project a constricting mask onto the sample and move the projected mask pattern in the desired fashion. This method also may be implemented electronically by controlling the illumination pattern of a suitable array of light sources, thus obviating the need for moving parts in the optical train.

The control of lateral bead transport by changing or moving patterns of illumination has the advantage that it may be applied whenever and wherever (on a given substrate surface) required, without the need to impose gradients in impedance by predefined UV patterning. On the other hand, a predefined impedance pattern can provide additional capabilities in conjunction with light-control. For example, it may be desirable to transport beads against a substrate-embedded impedance gradient to separate beads on the basis of mobility.

Conduits connecting O and F need not be straight: as with tracks directing the motion of trains, conduits may be shaped in any desirable fashion (FIG. 1d). A gated version of translocation (FIG. 1e) permits the transport of particles from O to F only after the conduit is opened (or formed in real time) by a gating signal. This operation utilizes UV oxide patterning to establish two holding areas, O and F, and also light control to temporarily establish a conduit connecting O and F. An alternative implementation is based on an oxide embedded impedance gradient. A zone along the conduit is illuminated with sufficiently high intensity to keep out particles, thereby blocking the passage. Removal (or reduction in intensity) of the illumination opens the conduit. In the former case, light enables the transport of beads, while in the latter case, light prevents the transport of beads.

The fundamental three-terminal operations are the merging and splitting of sets or arrays of beads (FIGS. 1f and 1g). The merging of two arrays (FIG. 1f) involves the previous two fundamental operations of "capture-and-hold", applied to two spatially isolated sets of beads in locations O1 and O2, and their respective channeling along merging conduits into a common target area, and their eventual channeling, subsequent to mixing, or a chemical reaction, into the final destination, a third holding area, F. This is accomplished, under the conditions stated above, by invoking one-terminal and gated two-terminal operations.

The splitting of an array into two subways (FIG. 1g) is a special case of a generally more complex sorting operation. Sorting involves the classification of beads in a given set or array into one of two subsets, for example according to their fluorescence intensity. In the simpler special case, a given array, held in area O, is to be split into two subarrays along a demarcation line, and subarrays are to be moved to target areas F1 and F2. Under the conditions stated above, this is accomplished by applying the "capture-and-hold" operation to the array in O. Conduits connect O to F1 and F2. High intensity illumination along a narrowly focused line serves to divide the array in a defined fashion, again relying on gated translocation to control transport along conduits away from the holding area O. An even simpler version, leaned indiscriminate splitting, randomly assigns particles into F1 and F2 by gated translocation of the array in O into F1 and F2 after conduits are opened as described above.

Figure 4A:
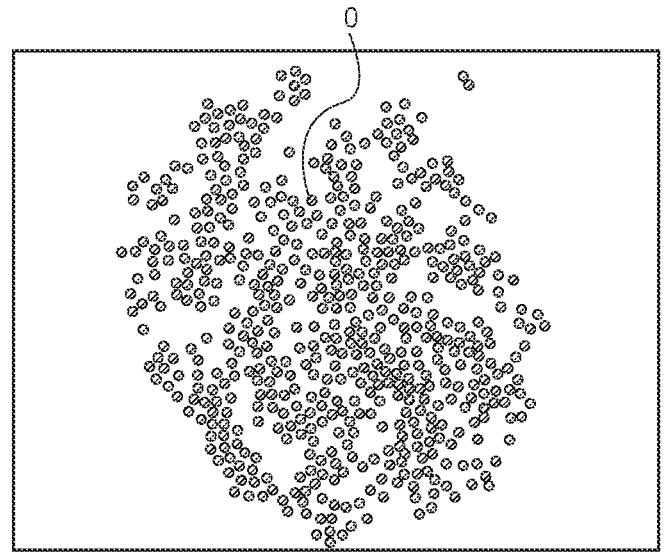
FIGS. 4A and 4B are photographs of the splitting of an existing aggregate into small clusters.
Figure 4B:
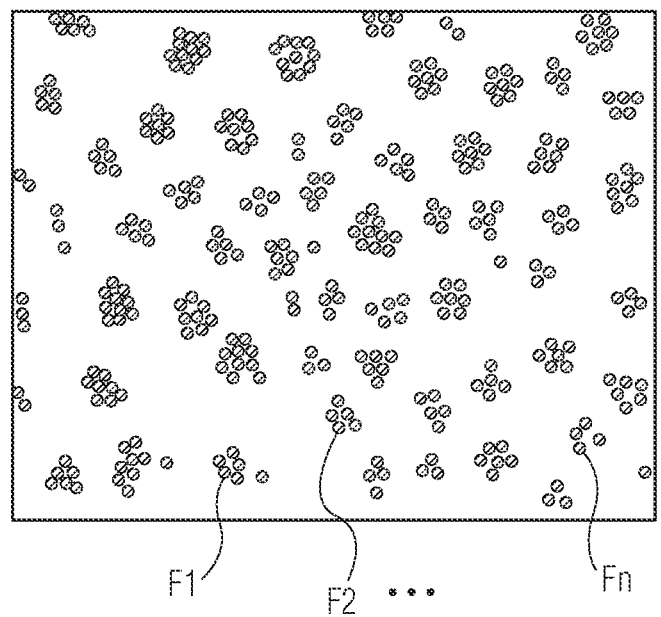

FIGS. 4a and 4b show a variant in which beads in region O (FIG. 4a) are split into multiple regions F1, F2, ... Fn (FIG. 4b). This reversible splitting of an aggregate or array into n subarrays, or clusters, is accomplished, for carboxylated polystyrene spheres of 2 micron diameter at a concentration corresponding to an electrode coverage of a small fraction of a monolayer, at a frequency of 500 Hz, by raising the applied voltage from typically 5V (pp) to 20V (pp). This fragmentation of an array into smaller clusters reflects the effect of a field-induced particle polarization. The splitting is useful to distribute particles in an array over a wider area of substrate for presentation to possible analytes in solution, and for subsequent scanning of the individual clusters with analytical instruments to make individual readings.

The three functional elements of the present invention described berth may be also combined to yield additional fundamental operations to control the orientation of anisotropic objects embedded in the electroosmotic flow created by the applied electric field at the electrode surface. The direction of the flow, in the plane of the substrate, is controlled by gradients in the impedance that are shaped in the manner described in connection with the channeling operation. This is used to controllably align anisotropic objects as illustrated in FIG. 1h, and may be applied to stretch out and align biomolecules, such as DNA.

An additional fundamental operation that complements the previous set is that of permanently anchoring an array to the substrate. This is best accomplished by invoking anchoring chemistries analogous to those relying on heterobifunctional cross-linking agents invoked to anchor proteins via amide bond formation. Molecular recognition, for example between biotinylated particles and surface-anchored streptavidin, provides another class of coupling chemistries for permanent anchoring.

General Experimental Conditions

The functional elements, namely the electric-field induced assembly of planar particle arrays, the spatial modulation of the interfacial impedance by means of UV-mediated oxide or surface-chemical patterning and finally, the control over the state of the interfacial impedance by light which are used in the present invention, have been demonstrated in experimental studies. These studies employed n-doped silicon wafers (resistivities in the range of 0.01 Ohm cm), capped with either thermally grown oxide layers of several thousand Angstrom thickness, or with thin oxide layers, regrown after removal of the original "native" oxide in HF, under UV illumination from a deuterium source in the presence of oxygen to typical thicknesses between 10 and 50 Angstroms. Lithographic patterning of thermally grown oxide employed standard procedures implemented on a bench top (rather than a clean room) to produce features in the range of several microns.

Surfaces were carefully cleaned in adherence with industry standard RCA and Piranha cleaning protocols. Substrates were stored in water produced by a Millipore cleaning system prior to use. Surfaces were characterized by measuring the contact angle exhibited by a 20 microliter droplet of water placed on the surface and viewed (from the side) through a telescope. The contact angle is defined as the angle subtended by the surface and the tangent to the droplet contour (in side view) at the point of contact with the surface. For example, a perfectly hemispherical droplet shape would correspond to a contact angle of 90 degrees. Surface chemical derivatization with mercapto-propyl-trimethoxysilane (2% in dry toluene) produced surfaces giving typical contact angles of 70 degrees. Oxidation of the terminal thiol functionality under UV irradiation in the presence of oxygen reduced the contact angle to zero in less than 10 min of exposure to UV from the deuterium source. Other silane reagents were used in a similar manner to produce hydrophobic surfaces, characterized by contact angles in excess of 110 degrees.

Simple "sandwich" electrochemical cells were constructed by employing kapton film as a spacer between Si/SiOx and conductive indium tin oxide (ITO), deposited on a thin glass substrate. Contacts to platinum leads were made with silver epoxy directly to the top of the ITO electrode and to the (oxide-stripped) backside of the Si electrode. In this two-electrode configuration, AC fields were produced by a function generator, with applied voltages ranging up to 20 V and frequencies varying from DC to 1 MHz, high frequencies favoring the formation of particle chains connecting the electrodes. Currents were monitored with a potentiostat and displayed on an oscilloscope. For convenience, epi-fluorescence as well as reflection differential interference contrast microscopy employed laser illumination. Light-induced modulations in EIS impedance were also produced with a simple 100 W microscope illuminator as well as with a 3 mW laser diode emitting light at 650-680 nm.

Colloidal beads, both anionic and cationic as well as nominally neutral, with a diameter in the range from several hundred Angstroms to 20 microns, stored in a $NaN_2$ solution, were employed.

Close attention was paid to colloidal stability to avoid non-specific interactions between particles and between particles and the electrode surface. Bacterial contamination of colloidal suspensions was scrupulously avoided.

Typical operating conditions producing, unless otherwise indicated, most of the results described herein, were: 0.2 mM $NaN_2$ (sodium azide) solutions, containing particles at a concentration so as to produce not more than a complete monolayer of particles when deposited on the electrode; applied DC potentials in the range of 1-4V, and AC potentials in the range of 1-10V (peak-to-peak) and 500 Hz-10 kHz, with an electrode gap of 50 microns; anionic (carboxylated polystyrene) beads of 2 micron diameter, as well as (nominally neutral) polystyrene beads of 2-20 micron diameter.

The method and apparatus of the present invention may be used in several different areas, examples of which are discussed in detail. Each example includes background information followed by the application of the present invention to that particular application.

Example I

Fabrication of Surfaces and Coatings with Designed Properties

The present invention may be used to fabricate planar surfaces and coatings with designed properties. Specifically, the functional elements of the present invention enable the formation of arrays composed of particles of a wide range of sizes (approximately 100 Angstrom to 10 microns) and chemical composition or surface functionality in response to AC or DC electric fields. These arrays may be placed and delineated in designated areas of the substrate, and the inter-particle spacing and internal state of order within the array may be controlled by adjusting the applied field prior to anchoring the array to the substrate. The newly formed surfaces display pre-designed mechanical, optical and chemical characteristics, and they may be subjected to further modification by subsequent treatment such as chemical cross-linking.

The mechanical and/or chemical modification of surfaces and coatings principally determines the interaction between materials in a wide range of applications that depend on low adhesion (e.g., the familiar "non-stick" surfaces important in housewares) or low friction (e.g., to reduce wear in computer hard disks), hydrophobicity (the tendency to repel water, e.g., of certain fabrics), catalytic activity or specific chemical functionality to either suppress molecular interactions with surfaces or to promote them. The latter area is of particular importance to the development of reliable and durable biosensors and bioelectronic devices. Finally, a large number of applications depend on surfaces of defined topography and/or chemical functionality to act as templates controlling the growth morphology of deposited materials or as "command surfaces" directing the alignment of optically active molecules in deposited thin organic films, as in liquid crystal display applications.

Extensive research has been devoted to the formation of surfaces by adsorption of thin organic films of known composition from the liquid or gas phase by several methods. Notwithstanding their seeming simplicity and wide-spread use, these methods can be difficult to handle in producing reliable and reproducible results. In addition, molecular films are not well suited to produce surfaces displaying playing a regular topography.

An alternative approach to the problem is the modification of conductive surfaces by electrophoretic deposition of suspended particulates. This is a widely used technique in industrial settings to produce paint coatings of metal parts, and to deposit phosphor for display screens. The active deposition process significantly enhances the kinetics of formation (in contrast to passive adsorption of organic films from solution), an important consideration in practical applications. Electrophoretic deposition requires high DC electric fields and produces layers in which particles are permanently adsorbed to the surface. While particles in so-deposited monolayers are usually randomly distributed, the formation of polycrystalline monolayers of small (150 Angstrom) gold colloids on carbon-coated copper grids is also known. However, the use of carbon-coated copper grids as substrates is not desirable in most applications.

Prior art methods have been described for the formation of ordered planar arrays of particles under certain conditions. For example, the formation of ordered colloidal arrays in response to AC electric fields on conductive indium tin oxide (ITO) electrodes is known. However, the resulting layers were composed of small patches of ordered arrays, randomly distributed over the surface of the otherwise bare ITO substrate. Arrays of monodisperse colloidal beads and globular proteins also have been previously fabricated by using convective flow and capillary forces. However, this latter process has the disadvantage of leaving deposited particle arrays immobilized and exposed to air, making it difficult to modify arrays by subsequent liquid phase chemistry.

The present invention provides a method of forming planar arrays with precise control over the mechanical, optical and chemical properties of the newly created layer. This method has several distinct advantages over the prior art. These result from the combination of AC electric field-induced array formation on insulating electrodes (Si/SiOx) that are patterned by UV-mediated oxide regrowth. The process of the present invention enables the formation of ordered planar arrays from the liquid phase (in which particles are originally suspended) in designated positions, and in accordance with a given overall outline. This eliminates the above-stated disadvantages of the prior art, i.e., dry state; irregular or no topography, random placement within an aggregate, immobilization of particles and uncontrolled, random placement of ordered patches on the substrate.

An advantage of the present invention is that arrays are maintained by the applied electric field in a liquid environment. The process leaves the array in a state that may be readily disassembled, subjected to further chemical modification such as cross-linking, or made permanent by chemical anchoring to the substrate. Furthermore, the liquid environment is favorable to ensure the proper functioning of many proteins and protein supramolecular assemblies of which arrays may be composed. It also facilitates the subsequent liquid-phase deposition of additional layers of molecules (by chemical binding to beads or proteins in the deposited layer), the cycling of arrays between states of different density and internal order (including complete disassembly of the array) in response to electric fields and the chemical cross-linking of particles into two-dimensionally connected layers, or gels, formed, for example, of chemically functionalized silica spheres. The present invention can be practiced on insulating electrodes such as oxide-capped silicon, to minimize Faradaic processes that might adversely affect chemical reactions involved in the gelation process or in anchoring the array to the substrate. The use of Si/SiOx electrodes also enables the control of array placement by external illumination.

The formation of colloidal arrays composed of small particles in accordance with the present invention provides a route to the fabrication of surfaces with relief structure on the scale of the particle diameter. Aside from their optical properties, such "micro-rough" surfaces are of interest as substrates for the deposition of DNA in such a way as to alleviate steric constraints and thus to facilitate enzyme access.

Particles to which the invention applies include silica spheres, polymer colloids, lipid vesicles (and related assemblies) containing membrane proteins such as bacteriorhodopsin $(bR)^-$ a light-driven proton pump that can be extracted in the form of membrane patches and disks or vesicles. Structured and functionalized surfaces composed of photoactive pigments are of interest in the context of providing elements of planar optical devices for the development of innovative display and memory technology. Other areas of potential impact of topographically structured and chemically functionalized surfaces are the fabrication of template surfaces for the controlled nucleation of deposited layer growth and command surfaces for liquid crystal alignment. The present invention also enables the fabrication of randomly heterogeneous composite surfaces. For example, the formation of arrays composed of a mixture of hydrophobic and hydrophilic beads of the same size creates a surface whose wetting and lubrication characteristics may be controlled by the composition of the deposited mixed head array. In this way, the location of the individual-beads is random, but the relative proportion of each type of bead within the allay is controllable.

Example II

Assembly of Lens Arrays and Optical Diffraction Elements

The present invention can be used to fabricate lens arrays and other surface-mounted optical elements such as diffraction gratings. The functional elements of the present invention enable the placement and delineation of these elements on ITO, facilitating integration with existing planar display technology, and on Si/SiOx, facilitating integration with existing silicon-based device technology.

Silica or other oxide particles, polymer latex beads or other objects of high refractive index suspended in an aqueous solution, will refract light. Ordered planar arrays of beads also diffract visible light, generating a characteristic diffraction pattern of sharp spots. This effect forms the basis of holographic techniques in optical information processing applications.

A.—The present invention provides for the use of arrays of refractive colloidal beads as light collection elements in planar array formats in conjunction with low light level detection and CCD imaging. CCD and related area detection schemes will benefit from the enhanced light collection efficiency in solid-phase fluorescence or luminescence binding assays.

This assay format relies on the detection of a fluorescence signal indicating the binding of probes to bead-anchored targets in the vicinity of the detector. To maximize through-put, it is desirable to monitor simultaneously as many binding events as possible. It is here that any formation by the methods of the present invention is particularly valuable because it facilitates the placement and tight packing of beads in the target area monitored by the CCD detector, while simultaneously providing for the additional benefit of lensing action and the resulting increase in light collection efficiency.

Figure 5:
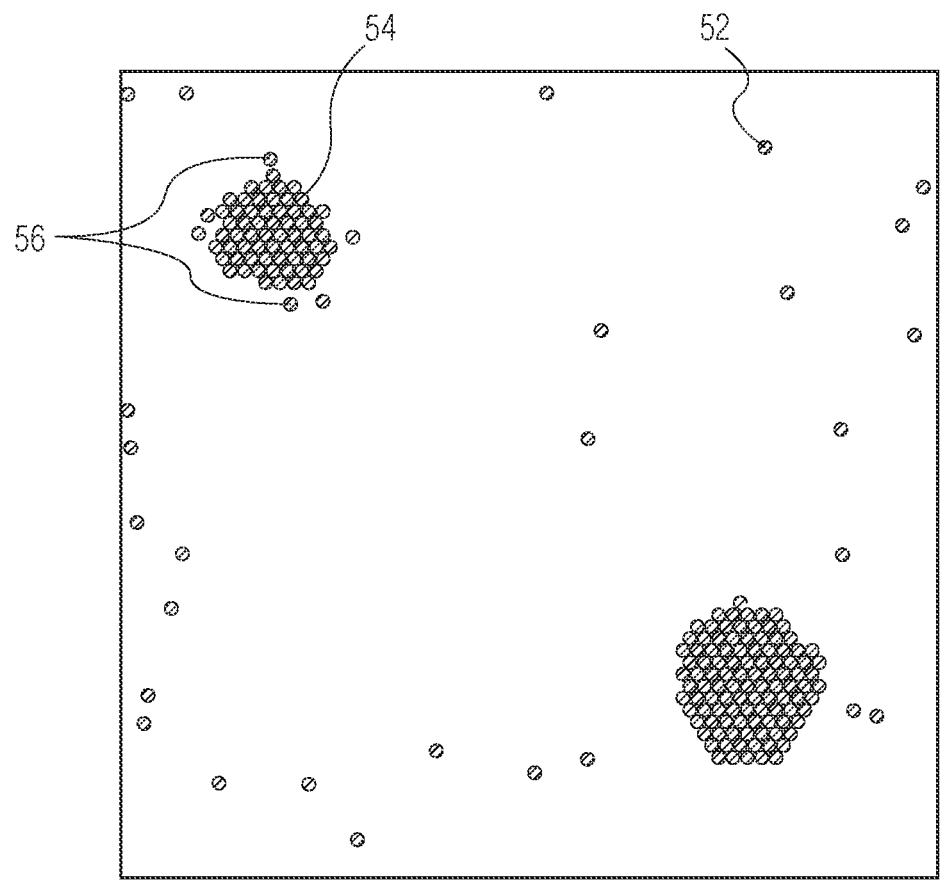
FIG. 5 is a photograph of the lensing action of individual colloidal beads.

Increased collection efficiency has been demonstrated in experiments employing individual, large (10 micron diameter) polystyrene beads as lensing elements to image small (1 micron diameter) fluorescent polystyrene beads. Under the experimental conditions set forth dove an applied voltage of 5V (pp) at 300 Hz induced the collection of small particles under individual large beads within a second. This is shown in FIG. 5, where small beads alone, e.g., 52, appear dim, whereas small beads, e.g., 54, gathered under a large bead 56 appear brighter and magnified. The small beads redisperse when the voltage is turned off.

B.—The use of colloidal bead arrays as diffraction gratings and thus as holographic elements is brown. Diffraction gratings have the property of diffracting light over a narrow range of wavelengths so that for given angle of incidence and wavelength of the illuminating light, the array will pass only a specific wavelength (or a narrow band of wavelengths centered on the nominal value) that is determined by the inter-particle spacing. Widely discussed applications of diffraction gratings range from simple wavelength filtering to the more demanding realization of spatial filters and related holographic elements that are essential in optical information processing.

The present invention provides for a rapid and well controlled process of forming planar arrays in a state of crystalline order which will function as surface-mounted optical diffraction elements. In addition, the resulting surfaces may be designed to display topographical relief to enhance wavelength selective reflectivity. These arrays may be formed in designated areas on a substrate surface. In contrast to the slow and cumbersome prior art method of fabricating such arrays by way of forming equilibrium crystals in aqueous solutions of low salt content, the present invention provides a novel approach to rapidly and reliably fabricate particle arrays at a solid-liquid interface. This approach relies on field-induced formation of arrays to bigger the process, and on UV-mediated patterning or light control to position and shape the arrays. In addition, the inter-particle distance, and internal state of order and hence the diffraction characteristics of the array, may be fine-tuned by adjusting the applied electric field. For example, a field-induced, reversible order-disorder transition in the array will alter the diffraction pattern from one composed of sharp spots to one composed of a diffuse ring. The assembly of such arrays on the surface of silicon wafers, as described herein, provides a direct method of integration into existing microelectronic designs. Arrays may be locked in place by chemical coupling to the substrate surface, or by relying on van der Waals attraction between beads and substrate.

Example III

A Novel Mechanism for the Realization of a Particle-Based Display

The present invention provides the elements to implement lateral particle motion as a novel approach to the realization of a particle-based display. The elements of the present invention provide for the control of the lateral motion of small particles in the presence of a pre-formed lens array composed of large, refractive particles.

Colloidal particulates have been previously employed in flat-panel display technology. The operating principle of these designs is based on electrophoretic motion of pigments in a colored fluid confined between two planar electrodes. In the OFF (dark) state, pigments are suspended in the fluid, and the color of the fluid defines the appearance of the display in that state. To attain the ON (bright) state, particles are assembled near the front (transparent) electrode under the action of an electric field. In this latter state, incident light is reflected by the layer of particles assembled near the electrode, and the display appears bright. Prototype displays employing small reflective particles in accordance with this design are known. However, these displays suffered from a number of serious problems including: electrochemical degradation and lack of colloidal stability as a result of prolonged exposure to the high DC electric fields required to achieve acceptable switching speeds; and non-uniformities introduced by particle migration in response to field gradients inherent in the design of the addressing scheme.

The present invention provides a novel mechanism for the design of a particle-based display which takes advantage of electric field-induced array formation as well as controlled, field-induced lateral particle displacements. First, a lens array composed of colloidal beads is formed. This lens array also serves as a spacer array to maintain a well-defined gap between the bottom electrode and the top electrode that may now be placed over the (pre-formed) array. This facilitates fabrication of uniform flat panel displays with a narrow gap that is determined by the particle diameter.

Next, small colloidal particles are added to the electrolyte solution in the gap. These may be fluorescent, or may be reflecting incident white light. Under the action of an AC electric field of appropriate frequency, these small particles can be moved laterally to assemble preferentially within the footprint of a larger bead. When viewed through a larger bead, small fluorescent beads assembled under a large bead appear bright as a result of the increased light collection efficiency provided by the leasing action of the huge bead; this is the ON state (FIG. 5). When moved outside the footprint of the larger bead, particles appear dim, and may be made entirely invisible by appropriate masking; this is the OFF state. The requisite lateral particle motion may be induced by a change in the applied voltage or a change in light intensity. Each large or leasing bead introduces a lateral nonuniformity in the current distribution within the electrolyte because the current is perturbed by the presence of each lensing bead.

In contrast to the prior art displays, the present invention employs AC, not DC fields, and insulating (rather than conductive) electrodes, thereby minimizing electrochemical degradation. The lateral non-uniformity introduced by the lens array is desirable because it introduces lateral gradients in the current distribution within the display cell. These gradients mediate the lateral motion of small beads over short characteristic distances set by the diameter of the large lensing beads, to effect a switching between ON and OFF states. Thus, the present invention readily accommodates existing technology for active matrix addressing.

Example IV

Layout-Preserving Transfer of Bead Suspensions from Microtiter Plate to Planar Cell The present invention provides a method to transfer suspensions of heads or biomolecules to the electrode surface in such a way as to preserve the spatial encoding in the original arrangement of reservoirs, most commonly the conventional 8×12 arrangement of wells in a microtiter plate. Such a fluid transfer scheme is of significant practical importance given that compound libraries are commonly handled and shipped in 8×12 wells.

The present invention utilizes chemical patterning to define individual compartments for each of M×N sets of beads and confine them accordingly. In the present instance, patterning is achieved by UV-mediated photochemical oxidation of a monolayer of thiol terminated alkylsilane that is chemisorbed to the Si/SiOx substrate. Partial oxidation of thiol moities produces sulfonate moities and renders the exposed surface charged and hydrophilic. The hydrophilic portions of the surface, in the form of a grid of squares or circles, will serve as holding areas.

In accordance with the present invention, the first function of surface-chemical patterning into hydrophilic sections surrounded by hydrophobic portions is to ensure that droplets, dispensed from different wells, will not fuse once they are in contact with the substrate. Consequently, respective bead suspensions will remain spatially isolated and preserve the layout of the original M×N well plate. The second role of the surface chemical patterning of the present invention is to impose a surface charge distribution, in the form of the M×N grid pattern, which ensures that individual bead arrays will remain confined to their respective holding areas even as the liquid phase becomes contiguous.

Figure 6A:
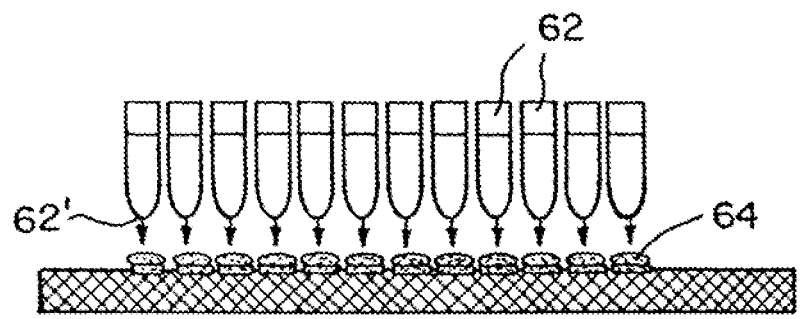
FIGS. 6A-6C are side view illustrations of a layout-preserving transfer process from a microtiter plate to a planar cell.
Figure 6B:
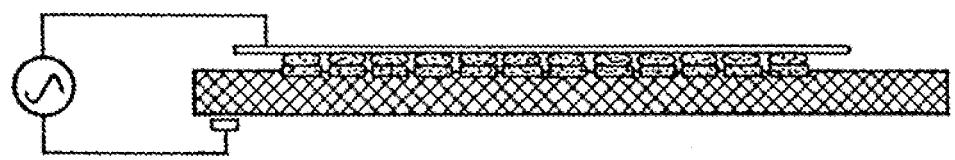
Figure 6C:
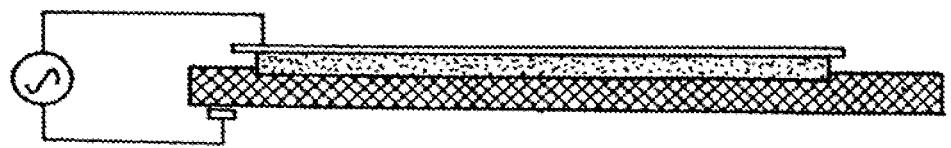

The transfer procedure involves the steps illustrated in FIGS. 6a-c. First, as shown in sideview in FIG. 6a, the M×N plate of wells 62 is registered with the pattern 64 on the planar substrate surface. Well bottoms 62 are pierced to allow for the formation of pendant drops of suspension or, preferably, the process is facilitated by a fixture (not shown) providing M×N effective funnels to match the geometric dimensions of the M×N plate on the top and reduce the size of the dispensing end. Such a dispensing fixture will also ensure the precise control of droplet volumes, adjusted so as to slightly overfill the target holding area on the patterned substrate surface. The set of M×N drops is then deposited by bringing them in contact with the hydrophilic holding areas of the pre-patterned substrate and relying on capillary action.

Next, the plate is retracted, and the top electrode is carefully lowered to form the electrochemical cell, first making contact as shown in FIG. 6b, with individual liquid-filled holding areas on the substrate to which suspensions are confined. Overfilling ensures that contact is made with individual suspensions. The electric field is now turned on to induce array formation in the M×N holding areas and to ensure the preservation of the overall configuration of the M×N sets of beads while the gap is closed further (or filled with additional buffer) to eventually fuse the individual droplets of suspension into a contiguous liquid phase as shown in FIG. 6c. In the fully assembled cell of FIG. 6c, while the droplets are fused together, the beads from each droplet are maintained in and isolated in their respective positions, reflecting the original M×N arrangement of wells. The present invention thus provides for the operations required in this implementation of a layout-preserving transfer procedure to load planar electrochemical cells.

Example V

Preparation of Heterogeneous Panels of Particles

The present invention provides a method to produce a heterogeneous panel of beads and potentially of biochemicals for presentation to analytes in an adjacent liquid. A heterogeneous panel contains particles or biomolecules which differ in the nature of the chemical or biochemical binding sites they offer to analytes in solution. In the event of binding, the analyte is identified by the coordinates of the bead, or cluster of beads, scoring positive. The present method relies on the functional elements of the invention to assemble a planar array of a multi-component mixture of beads which carry chemical labels in the form of tag molecules and may be so identified subsequent to performing the assay.

Diagnostic assays are frequently implemented in a planar format of a heterogeneous panel, composed of simple ligands, proteins and other biomolecular targets. For example, in a diagnostic test kit, a heterogeneous panel facilitates the rapid testing of a given analyte, added in solution, against an entire set of targets. Heterogeneous panels or proteins are of great current interest in connection with the emerging field of proteome research. The objective of this research is to identify, by scanning the panel with sensitive analytical techniques such as mass spectrometry, each protein in a multi-component mixture extracted from a cell and separated by two-dimensional gel electrophoresis. Ideally, the location of each spot uniquely corresponds to one particular protein. This analysis would permit, for example, the direct monitoring of gene expression levels in a cell during a particular point in its cycle or at a given stage during embryonic development.

The fabrication of an array of heterogeneous targets is central to recently proposed strategies of drug screening and DNA mutation analysis in a planar format. The placement of ligands in a specific configuration on the surface of a planar substrate serves to maintain a key to the identity of any one in a large set of targets presented simultaneously to an analyte in solution for binding or hybridization. In an assay relying on fluorescence, binding to a specific target will create bright spots on the substrate whose spatial coordinates directly indicate the identity of the target.

Three principal strategies have been previously employed to fabricate heterogeneous panels. First, protein panels may be created by two-dimensional gel electrophoresis, relying on a DC electric field to separate proteins first by charge and then by size (or molecular weight). Even after many years of refinement, this technique yields results of poor reproducibility which are generally attributed to the poorly defined properties of the gel matrix.

Second, individual droplets, drawn from a set of reservoirs containing solutions of the different targets, may be dispensed either by hand or by employing one of several methods of automated dispensing (or "printing"; see e.g., Schena et al., Science 270, 467-470 (1995), the contents of which are incorporated herein by reference). Printing has been applied to create panels of oligonucleotides intended for screening assays based on hybridization. Printing leaves a dried sample and may thus not be suitable for proteins that would denature under such conditions. In addition, the attendant fluid handling problems, inherent in maintaining, and drawing samples from a large number of reservoirs are formidable.

Third, target ligands may be created by invoking a variant of solid phase synthesis based on a combinatorial strategy of photochemically activated elongation reactions. This approach has been limited by very formidable technical problems in the chemical synthesis of even the simplest, linear oligomers. The synthesis of non-linear compounds in this planar geometry is extremely difficult.

The present invention of forming heterogeneous panels requires the chemical attachment of target ligands to beads. Ligands may be coupled to beads "off-line" by a variety of well established coupling reactions. For present purposes, the bead identity must be chemically encoded so it may be determined as needed. Several methods of encoding, or binary encoding, of beads are available. For example, short oligonucleotides may serve the purpose of identifying a bead via their sequence which may be determined by microscale sequencing techniques. Alternatively, chemically inert molecular tags may be employed that are readily identified by standard analytical techniques.

Figure 7:
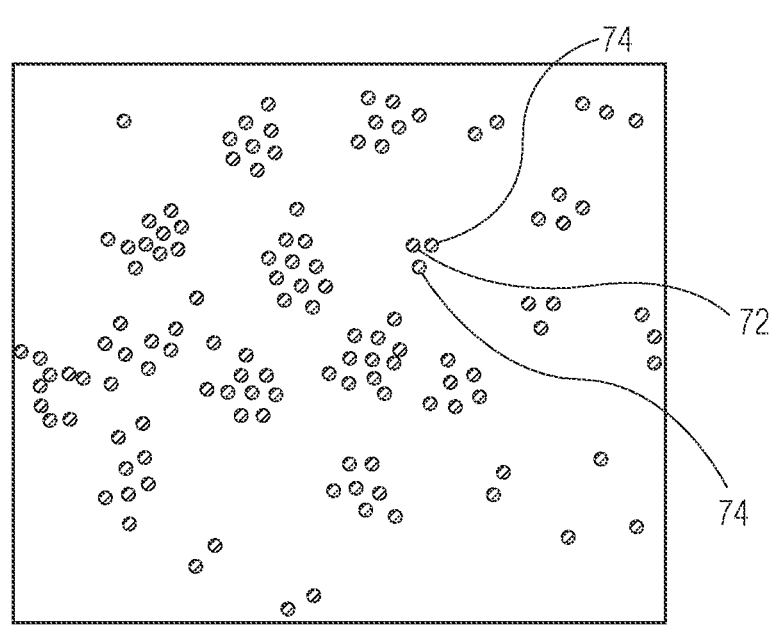
FIG. 7 is a photograph of the inclusion of spacer particles within bead clusters.

In contrast to all prior art methods, the present invention provides a novel method to create heterogeneous panels by in-situ, reversible formation of a planar array of "encoded" beads in solution adjacent to an electrode. The array may be random with suspect to chemical identity but is ordered with respect to spatial position. This procedure offers several advantages. First, it is reversible so that the panel may be disassembled following the binding assay to discard beads scoring negative. Positive beads may be subjected to additional analysis without the need for intermediate steps of sample retrieval, purification or transfer between containers. Second, the panel is foraged when needed, that is, either prior to performing the actual binding assay, or subsequent to performing the assay on the surface of individual beads in suspension. The latter mode minimizes potential adverse effects that can arise when probes bind to planar target surfaces with a high concentration of target sites. Third, to accommodate scanning probe analysis of individual beads, interparticle distances within the array may be adjusted by field-induced polarization or by the addition of inert spacer particles that differ in size front the encoded beads. FIG. 7 shows the use of small spacer beads 72 for separating encoded beads 74. As shown, the spacing of beads 74 is greater than the spacing of comparable beads in FIG. 4b. Finally, UV-mediated oxide regrowth, as provided by the present invention, readily facilitates the embedding of a grid pattern of selected dimension into the substrate to ensure the formation of small, layout-preserving subarrays in the low-impedance fields of the grid.

To create the panel, a multi-component mixture of beads carrying, for example, compounds produced by bead-based combinatorial chemistry, is placed between electrodes. Each type of bead may be present in multiple copies. Arrays are formed in response to an external field in a designated area of the electrode surface. This novel approach of in-situ assembly of panels relies on beads that carry a unique chemical label, or code, to permit their identification subsequent to the completion of a binding assay. This invention facilitates on-line tagging of bouts by way of a photochemical bead-coloring method. Selected beads in an array are individually illuminated by a focused light source to trigger a coloring reaction on the bead surface or in the bead interior to indicate a positive assay score. Beads so marked can be subsequently separated from unmarked beads by a light-activated sorting method described herein. Numerous UV-activated reactions are available to implement this bead-coloring method.

The present invention provides for several methods of discarding beads with negative scores, typically the vast majority, while retaining those with positive scores. This method take advantage of the fact that, in contrast to all prior it methods, the array represents a temporary configuration of particles that is maintained by the applied electric field and may be rearranged or disassembled at will. This capability, along with the fact that biomolecules are never exposed to air (as in the prior art method of printing) facilitates the in-situ concatenation of analytical procedures that require the heterogeneous panel in conjunction with subsequent, "downstream" analysis.

First, if positive beads are clustered in a subsection of the array, the light-controlled array splitting operation of the present invention may be invoked to dissect the array so as to discard negative portions of the array (or recycle them for subsequent use). Second, if positive and negative beads are randomly interspersed, a fluorescence-activated sorting method, implemented on the basis of the present invention in a planar format, as described herein, may be invoked. In the case of fluorescence-activated sorting, positive and negative beads may be identified as bright and dark objects, respectively. In the special case that only a few positive beads stand out, these may be removed from the array by locking onto them with optical tweezers, a tool to trap and/or manipulate individual refractive particles under illumination, and disassembling the array by removing the field, or subjecting the entire array to lateral displacement by the fundamental operations of the present invention.

The typical task in screening a large set of compounds is one of Looking for a very small number of positive events in a vast number of tests. The set of discarded beads will typically involve the majority at each stage in the assay. The procedure of the present invention therefore minimizes the effort invested in negative events, such as the challenging in-situ synthesis of target ligands irrespective of whether or not they will prove to be of interest by binding a probe offered in solution.

The method of forming a heterogeneous panel according to the present invention contains beads of each type in generally random assembly. The creation of a heterogeneous panel with each position in the panel containing a cluster of beads of the same type, that is, beads originating in the same reservoir (FIG. 6a), may be desirable so as to ensure a sufficiently large number of positive events to facilitate detection. A practical solution follows from the application of the layout-preserving fluidic transfer scheme described herein. In this procedure, beads from an M×N well plate are transferred layout-preservingly onto a chemically patterned substrate in such a way as to preserve the spatial encoding of bead identities.

Example VI

Binding and Functional Assays in Planar Bead Array Format

Figure 8:
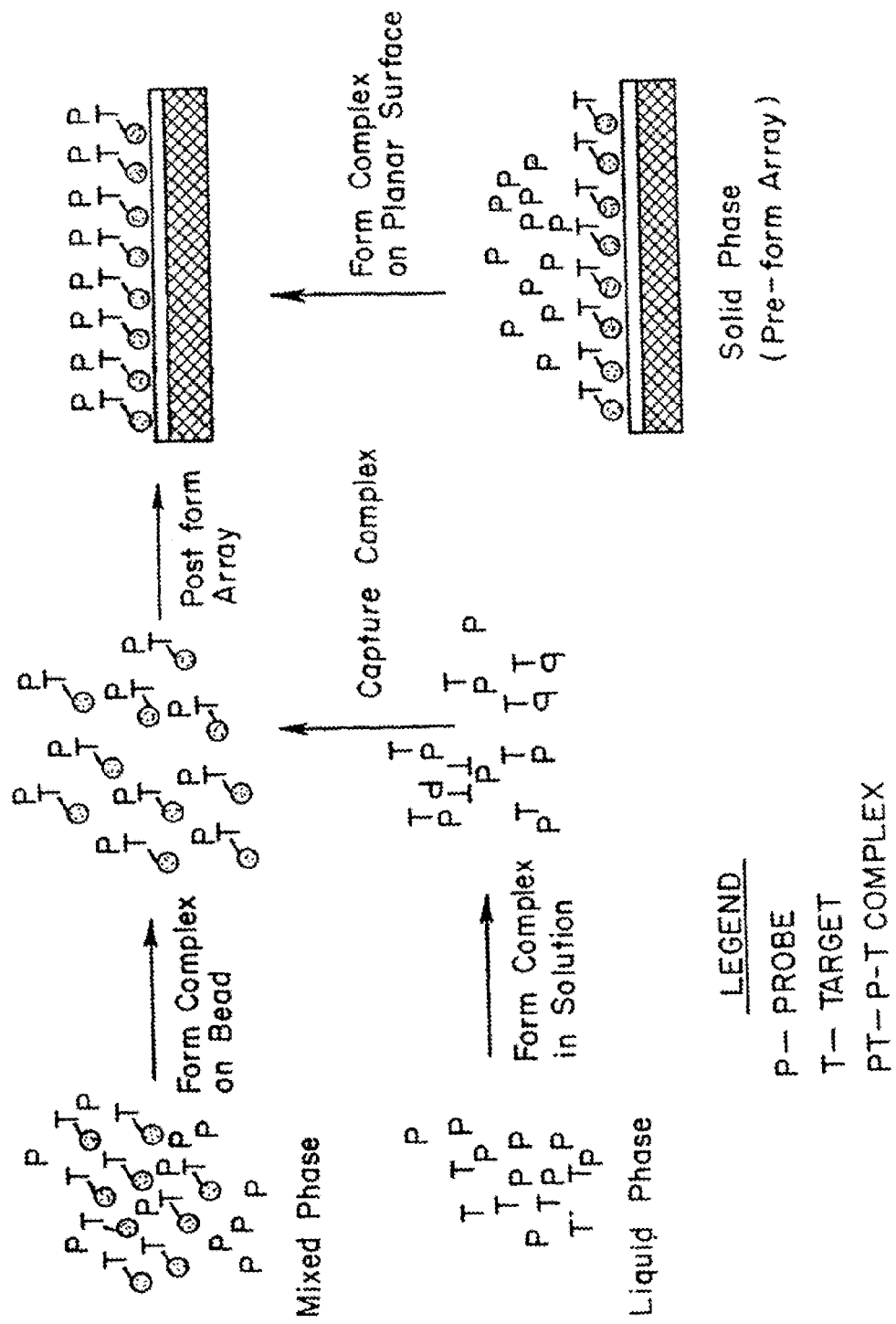
FIG. 8 is an illustration of binding assay variations.
Figure 11A:
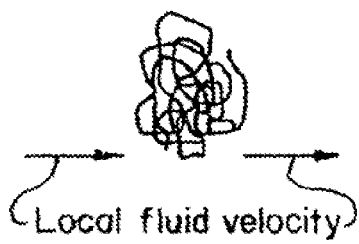
FIGS. 11A-11E are illustrations of DNA stretching in accordance with the present invention.
Figure 11B:
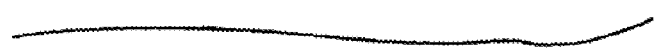
Figure 11C:
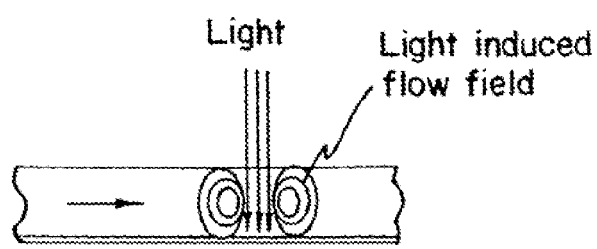
Figure 11D:
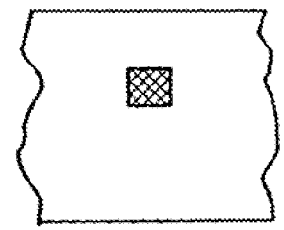
Figure 11E:
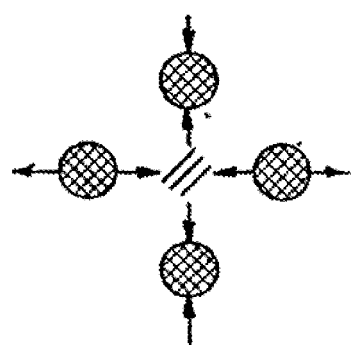

The present invention can be used to implement mixed-phase binding assays as well as certain functional assays in a planar array format. Several combinations are possible reflecting the presence of probe or target in solution, on the surface of colloidal beads, or on the electrode surface. The methods of the present invention facilitate the formation of a planar array to present targets to probes in solution prior to performing the binding assay ("preformed" array; FIG. 8). Alternatively, a planar array of beads may be formed in front of a detector surface subsequent to performing the binding assay in suspension ("postformed" array; FIG. 8). The present invention also provides the methods to implement functional assays by enabling the assembly of certain cell types adjacent to a planar detector or sensor surface to monitor the effects of exposure of the cells to small molecule drugs in solution.

Binding assays, particularly those involving proteins such as enzymes and antibodies, represent a principal tool of medical diagnostics. They are based on the specific biochemical interaction between a probe, such as a small molecule, and a target, such as a protein. Assays facilitate the rapid detection of small quantities of an analyte in solution with high molecular specificity. Many procedures have been designed to produce signals to indicate binding, either yielding a qualitative answer (binding or no binding) or quantitative results in the form of binding or association constants. For example, when an enzyme binds an analyte, the resulting catalytic reaction may be used to generate a simple color change to indicate binding, or it may be coupled to other processes to produce chemical or electrical signals from which binding constants are determined. Monoclonal antibodies, raised from a single common precursor, may be prepared to recognize virtually any given target, and immunoassays, based on antibody-antigen recognition and binding, have developed into an important diagnostic tool. As with enzyme binding, antibody binding of an antigenic analyte may be detected by a variety of techniques including the classic method of enzyme-linked immunoassays (ELISA) in which the reaction of an antibody-coupled enzyme is exploited as an indicator. A common and conceptually simple scheme ensures the detection of antibody binding to a target analyte by supplying a fluorescently labeled second antibody that recognizes the first (or primary) antibody.

Binding assays involving soluble globular proteins are often performed in solution to ensure unbiased interactions between protein and target. Such liquid phase assays, especially when performed at low concentrations of target or probe, minimize potential difficulties that may arise when either target or probe are present in abundance or in close proximity. By the same token, the kinetics tend to be slow. Cooperative effects, such as crowding, arising from the close proximity of probes must be carefully controlled when either probe or target is chemically anchored to a solid substrate.

Nonetheless, this latter solid phase format of binding assays is also very commonly employed whenever the situation demands it. For example, the presence of a protein on the surface of a cell may be exploited in "panning" for the cells that express this protein in the presence of many other cells in a culture that do not: desired cells attach themselves to the surface of a container that is pre-coated with a layer of a secondary antibody directed against a primary antibody decorating the desired cell-surface protein. Similarly, certain phages may be genetically manipulated to display proteins on their surface, and these may be identified by a binding assay involving a small molecule probe such as an antigen if the protein displayed is an antibody (Watson et al., "Recombinant DNA", 2nd Edition (Scientific American Book, Freeman and Co., New York, N.Y., 1983), the contents of which are incorporated herein by reference). In addition, the planar geometry accommodates a variety of optical and electrical detection schemes implemented in transducers and sensors.

A combination of liquid phase and solid phase assay may be developed by using beads that are decorated with either probe or target, as in procedures that employ decorated magnetic beads for sample preparation or purification by isolating binding from non-binding molecules in a given multi-component mixture. Recent examples of the use of these beads include the purification of templates for DNA sequencing applications or the extraction of mRNAs from (lysed) cells by hybridization to beads that are decorated with poly-adenine (polyA) residues.

Functional assays involving suitable types of cells are employed to monitor extracellular effects of small molecule drugs on cell metabolism. Cells are placed in the immediate vicinity of a planar sensor to maximize the local concentration of agents released by the cell or to monitor the pH.

The present invention provides the means to implement mixed phase binding assays in a planar geometry with a degree of flexibility and control that is not available by prior art methods. Thus, it offers the flexibility of forming, in-situ, reversibly and under external spatial control, either a planar panel of target sites for binding of analyte present in an adjacent liquid phase, or a planar array of probe-target complexes subsequent to performing a binding assay in solution. Binding may take place at the surface of individual beads suspended in solution, at the surface of beads pre-assembled into arrays adjacent to the electrode surface, or at the electrode surface itself. Either the target or probe molecule must be located on a bead to allow for a bead-based assay according to the present invention. As shown in FIG. 8, if the probe molecule P is located on a bead, then the target molecule T may be either in solution, on a bead or on the electrode surface. The converse is also true.

For example, the methods of the present invention may be used to implement panning, practiced to clone cell surface receptors, in a far more expeditious and controlled manner than is possible by the prior art method. Given a substrate that has been coated with a layer of antibody directed against the sought-after cell surface protein, the present invention facilitates the rapid assembly of a planar array of cells or decorated beads in proximity to the layer of antibodies and the subsequent disassembly of the away to leave behind only those cells or beads capable of forming a complex with the surface-bound antibody.

A further example of interest in this category pertains to phage displays. This technique may be employed to present a layer of protein targets to bead-anchored probes. Bead arrays may now be employed to identify a protein of interest. That is, beads are decorated with small molecule probes and an array is formed adjacent to the phage display. Binding will result in a probe-target complex that retains beads while others are removed when the electric field is turned off, or when light-control is applied to remove beads from the phage display. If beads are encoded, many binding tests may be carried out in parallel because retained beads may be individually identified subsequent to binding.

The methods of the present invention readily facilitate competitive binding assays. For example, subsequent to binding of a fluorescent probe to a target-decorated bead in solution and the formation of a planar bead array adjacent to the electrode, fluorescent areas within the array indicate the position of positive targets, and these may be further probed by subjecting them to competitive binding. That is, while monitoring the fluorescence of a selected section of the planar array, an inhibitor (for enzyme assays) or other antagonist (of known binding constant) is added to the electrochemical cell, and the decrease in fluorescence originating from the region of interest is measured as a function of antagonist concentration to determine a binding constant for the original probe. This is an example of a concatenation of analytical steps that is enabled by the methods of the present invention.

The fact that a probe-target complex is fixed to a colloidal bead, as in the methods of the present invention, conveys practical advantages because this facilitates separation of positive from negative events. Particularly when solid phase assays are performed on a planar substrate, an additional advantage of planar bead arrays is the enhancement of light collection efficiency provided by the beads, as discussed herein.

If desired, beads may serve strictly as delivery vehicles for small molecule probes. That is, an array of probe-decorated beads is formed adjacent to a target-decorated surface in accordance with the methods of the present invention UV-activated cleavage of the probe from the bead support will ensure that the probe is released in close proximity to the target layer, thereby enhancing speed and efficiency of the assay. The identity of the particular probe interacting with the target may be ascertained from the positional location of the bead delivering the probe.

The methods of the present invention apply not only to colloidal beads of a wide variety (bat need no special preparative procedures to make there magnetic, for example), but also to lipid vesicles and cells that are decorated with, or contain embedded in their outer wall, either probe or target. The methods of the present invention may therefore be applied not only to bead-anchored soluble proteins but potentially to integral membrane receptors or to cell surface receptors.

In particular, the rapid assembly of cells in a designated area of the substrate surface facilitates the implementation of highly parallel cell-based functional assays. The present invention makes it possible to expose cells to small molecule drug candidates in solution and rapidly assemble them in the vicinity of a sensor embedded in the electrode surface, or to expose pre-assembled cells to such agents that are released into the adjacent liquid phase. In the simplest case, all cells will be of the same type, and agents will be administered sequentially. Even in this sequential version, electrokinetic mixing will enhance through-put. However, as described herein, the methods of the present invention also enable the parallel version of binding assays and thus of functional assays in a planar format by encoding the identity of different cells by a "Layout-Preserving Transfer" process from an 8×12 well plate, as discussed herein, and to isolate cells scoring positive by providing feed-back from a spatially resolved imaging or sensing process to target a specific location in the array of cells.

Example VII

Separation and Sorting of Beads and Particles

The present invention can be used to implement several procedures for the separation and sorting of colloidal particles and biomolecules in a planar geometry. Specifically, these include techniques of lateral separation of beads in mixtures. Individual beads may be removed from an array formed in response to an electric field by the application of optical tweezers.

The separation of components in a given mixture of chemical compounds is a fundamental task of analytical chemistry. Similarly, biochemical analysis frequently calls for the separation of biomolecules, beads or cells according to size and/or surface charge by electrophoretic techniques, while the sorting (most commonly into just two sub-classes) of suspended cells or whole chromosomes according to optical properties such as fluorescence emission is usually performed using field-flow fractionation including flow cytometry and fluorescence-activated cell sorting.

In a planar geometry, bead mixtures undergoing diffusion have been previously separated according to mobility by application of an AC electric field in conjunction with lithographic patterning of the electrode surface designed to promote directional drift. Essentially, the AC or pulsing electric field is used to move small beads in a particular direction over a period of time. Capillary electrophoresis has been implemented in a planar geometry, see e.g., B. B. Haab and R. A. Mathies, Anal. Chem. 67, 3253-3260 (1995), the contents of which are incorporated herein by reference.

The methods of the present invention may be applied in several ways to implement the task of separation, sorting or isolation in a planar geometry. In contrast to the prior art approaches, the present invention provides a significant degree of flexibility in selecting from among several available procedures, the one best suited to the particular task at hand. In some cases, more than one separation technique may be applied, and this provides the basis for the implementation of two-dimensional separation. That is, beads may be separated according to two different physical-chemical characteristics. For example, beads may first be separated by size and subsequently, by raising the applied frequency to induce chain formation, by polarizability. This flexibility offers particular advantages in the context of integrating analytical functionalities in a planar geometry. Several techniques will now be described.

i) The present invention may be used to implement "sieving" in lateral, electric field-induced flow on surfaces patterned by UV-mediated oxide regrowth to sort beads in a mixture by size. The fundamental operations of the invention are invoked to set up directed lateral particle motion along conduits laid out by UV-mediated oxide regrowth. Conduits are designed to contain successively narrower constrictions through which particles must pass. Successively finer stages allow only successively smaller particles to pass in this "sieving" mechanism (FIG. 9a). As shown in FIG. 9a, the primary particle flow is in the direction left to right, while a transverse flow is established in the top to bottom direction utilizing an oxide profile as shown. Additionally, rows of barriers 92 made from thick oxide are positioned along the conduit with the spacing between the barriers in each row decreasing in the transverse direction. As the particles move along the conduit, the rows of barriers act to separate out smaller particles in the transverse direction. In contrast to previous methods based on electrophoretic separation, large DC electric fields, and the attendant potential problem of electrolysis and interference from electroosmotic flow in a direction opposite to the field-directed particle transport, the present invention uses AC electric fields and lateral gradients in interfacial impedance to produce transport. The present method has the advantage of avoiding electrolysis and it takes explicit advantage of electroosmotic flow to produce and control particle transport.

In addition, the use of Si/SiOx electrodes enables the use of the light-control component of the present invention to modify lateral transport of beads in real time. For example, external illumination may be employed to locally neutralize the lateral impedance gradient induced by UV-mediated oxide regrowth. Particles in these neutral "zones" would no longer experience any net force and come to rest. This principle may be used as a basis for the implementation of a scheme to locally concentrate particles into sharp bands and thereby to improve resolution in subsequent separation.

ii) The present invention may be used to implement "zone refining", a process of excluding minority components of a mixture by size or shape from a growing crystalline array of majority component. This process explicitly depends on the capabilities of the present invention to induce directional crystallization.

The process of zone refining is employed with great success in producing large single crystals of silicon of very high purity by excluding impurities from the host lattice. The concept is familiar from the standard chemical procedure of purification by recrystallization in which atoms or molecules that are sufficiently different in size, shape or charge from the host species so as not to fit into the forming host crystal lattice as a substitutional impurity, are ejected into solution.

By enabling the growth of planar arrays, in a given direction and at a controlled rate, the present invention facilitates the implementation of an analogous zone refining process for planar arrays. The most basic geometry is the linear geometry. A multi-component mixture of beads of different sizes and/or shapes is first captured in a rectangular holding area on the surface, laid out by UV-patterning. Next, crystallization is initiated at one end of the holding area by illumination and allowed to slowly advance across the entire holding area in response to an advancing pattern of illumination. In general, differences of approximately 10% in bead radius trigger ejection.

iii) The present invention may be used to implement fractionation in a transverse flow in a manner that separates particles according to mobility.

Field-flow fractionation refers to an entire class of techniques that are in wide use for the separation of molecules or suspended particles. The principle is to separate particles subjected to fluid flow in a field acting transverse to the flow. A category of such techniques is subsumed under the heading of electric-field flow fractionation of which free-flow electrophoresis is a pertinent example because it is compatible with a planar geometry. Free-flow electrophoresis employs the continuous flow of a replenished buffer between two narrowly spaced plates in the presence of a DC electric field that is applied in the plane of the bounding plates transverse to the direction of fluid flow. As they traverse the electric field, charged particles are deflected in proportion to their electrophoretic mobility and collected in separate outlets for subsequent analysis. In contrast to conventional electrophoresis, free-flow electrophoresis is a continuous process with high throughput and it requires no supporting medium such as a gel.

The present invention enables the implementation of field-flow fractionation in a planar geometry. As previously discussed herein, impedance gradients imposed by UV-oxide profiling serve to mediate particle motion along the electrode surface in response to the external electric field. In a cell with a narrow gap, the resulting electrokinetic flow has a "plug" profile and this has the advantage of exposing all particles to identical values of the flow velocity field, thereby minimizing band distortions introduced by the parabolic velocity profile of the laminar flow typically employed in free-flow electrophoresis.

A second flow field, transverse to the primary flow direction, may be employed to mediate particle separation. This deflecting flow may be generated in response to a second impedance gradient. A convenient method of imposing this second gradient is to take advantage of UV-oxide patterning to design appropriate flow fields. Both longitudinal and transverse flow would be recirculating and thus permit continuous operation even in a closed cell, in contrast to any related prior art technique.

Additional flexibility is afforded by invoking the light-control component of the present invention to illuminate the substrate with a stationary pattern whose intensity profile in the direction transverse to the primary fluid flow is designed to induce the desired impedance gradient and hence produce a transverse fluid flow. (FIG. 9b). This has the significant advantage of permitting selective activation of the transverse flow in response to the detection of a fluorescent bead crossing a monitoring window upstream. Non-fluorescent beads would not activate the transverse flow and would not be deflected. This procedure represents a planar analog of flow cytometry, or fluorescence-activated cell sorting.

iv) The invention may be used to induce the formation of particle chains in the direction normal to the plane of the electrode. The chains represent conduits for current transport between the electrodes and their formation may reflect a field-induced polarization. Chains are much less mobile in transverse flow than are individual particles so that this effect may be used to separate particles according to the surface properties that contribute to the net polarization. The effect of reversible chain formation has been demonstrated under the experimental conditions stated herein. For example, the reversible formation of chains occurs, for carboxylated polystyrene beads of 1 micron diameter, at a voltage of 15 V (pp) at frequencies in excess of 1 MHz.

v) The invention may be used to isolate individual beads from a planar array.

Fluorescence binding assays in a planar array format, as described herein, may produce singular, bright beads within a large array, indicating particularly strong binding. To isolate and retrieve the corresponding beads, optical tweezers in the form of a sharply focused laser spot, may be employed to lock onto an individual bead of interest. The light-control component of the present invention may be used in conjunction with the optical tweezers to retrieve such an individual bead by moving the array relative to the bead, or vice versa, or by disassembling the array and retaining only the marked bead. This is a rather unique capability that will be particularly useful in the context of isolating beads in certain binding assays.

Commercial instrumentation is available to position optical tweezers in the field of a microscope. Larger scale motion is facilitated by translocating the array in-situ or simply by moving the external sample fixture. This process lends itself to automation in conjunction with the use of peak-finding image analysis software and feedback control.

vi) The invention may be used to implement a light-induced array sectioning ("shearing") operation to separate fluorescent, or otherwise delineated portions of an array from the remainder. This operation makes it possible to segment a given array and to isolate the corresponding beads for downstream analysis.

The basis for the implementation of this array segmentation is the light-control component of the present invention, in the mode of driving particles from an area of a Si/SiOx interface that is illuminated with high intensity. It is emphasized here that this effect is completely unrelated to the light-induced force on beads that underlies the action of optical tweezers. The present effect which operates on large sets of particles, was demonstrated under the experimental conditions stated herein using a 100 W illuminator on a Zeiss UEM microscope operated in epi-illumination. A simple implementation is to superimpose, on the uniform illumination pattern applied to the entire array, a line-focused beam that is positioned by manipulation of beam steering elements external to the microscope. Beads are driven out of the illuminated linear portion. Other implementations take advantage of two separately controlled beams that are partially superimposed. The linear sectioning can be repeated in different relative orientations of shear and array.

Example VIII

Screening for Drug Discovery in Planar Geometry

The functional elements of the present invention may be combined to implement procedures for handling and screening of compound and combinatorial libraries in a planar format. The principal requisite elements of this task are: sample and reagent delivery from the set of original sample reservoirs, commonly in a format of 8×12 wells in a microliter plate, into a planar cell; fabrication of planar arrays of targets or of probe-target complexes adjacent to the planar electrode surface prior to or subsequent to performing a binding assay; evaluation of the binding assay by imaging the spatial distribution of marker fluorescence or radioactivity, optionally followed by quantitative pharmacokinetic measurements of affinity or binding constants; isolation of beads scoring positive, and removal from further processing of other beads; and collection of specific beads for additional downstream analysis. The present invention relates to all of these elements, and the fundamental operations of the invention provide the means to concatenate these procedures in a planar format.

A central issue in the implementation of cost-effective strategies for modern therapeutic drug discovery is the design and implementation of screening assays in a manner facilitating high throughput while providing pharmacokinetic data as a basis to select promising drug leads from a typically vast library of compounds. That is, molecular specificity for the target, characterized by a binding constant, is an important factor in the evaluation of a new compound as a potential therapeutic agent. Common targets include enzymes and receptors as well as nucleic acid ligands displaying characteristic secondary structure.

The emerging paradigm for lead discovery in pharmaceutical and related industries such as agricultural biotechnology, is the assembly of novel synthetic compound libraries by a broad variety of new methods of solid state "combinatorial" synthesis. Combinatorial chemistry refers to a category of strategies for the parallel synthesis and testing of multiple compounds or compound mixtures in solution or on solid supports. For example, a combinatorial synthesis of a linear oligopeptide containing n amino acids would simultaneously create all compounds representing the possible sequence permutations of n amino acids. The most commonly employed implementation of combinatorial synthesis relies on colloidal bead supports to encode reaction steps and thus the identity of each compound. Beads preferred in current practice tend to be large (up to 500 microns in diameter) and porous to maximize their compound storage capacity, and they must be encoded to preserve the identity of the compound they carry.

Several methods of encoding, or binary encoding, of beads are available. Two examples are as follows. First, beads may be labeled with short oligonucleotides such as the 17-mers typically employed in hybridization experiments. The sequence of such short probes may be determined by microscale sequencing techniques such as direct Maxam-Gilbert sequencing or mass spectrometry. This encoding scheme is suitable when the task calls for screening of libraries of nucleic acid ligands or oligopeptides. Second, members of a combinatorial library may be associated with chemically inert molecular tags. In contrast to the previous case, these tag molecules are not sequentially linked. Instead, the sequence of reaction steps is encoded by the formal assignment of a binary code to individual tag molecules and their mixtures that are attached to the bead in each successive reaction step. The tags are readily identified by standard analytical techniques such as gas chromatography. This general encoding strategy is currently employed in the synthesis of combinatorial libraries on colloidal beads.

Commercial compound libraries are large, given that even for the aforementioned 17-mer, the number of sequence permutations is $4^{17}$, or approximately $10^{10}$. However, the high specificity of typical biological substrate-target interactions implies that the vast majority of compounds in the collection will be inactive for any one particular target. The task of screening is to select from this large set the few potential lead compounds displaying activity in binding or in functional assays. The principal drug discovery strategy widely applied to natural compound libraries in the pharmaceutical industry is to select individual compounds from the library at random and subject them to a series of tests. Systematic screening procedures are thus required to implement the rapid screening and scoring of an entire library of synthetic compounds, in practice often containing on the order of $10^7$ items.

In current practice, compounds are first cleaved and doted from their solid supports and are stoned in microtiter plates. Further sample handling in the course of screening relies primarily on robotic pipetting and transfer between different containers, typically wells in microtiter plates. While robotic workstations represent a step in the direction of automating the process, they rely on the traditional format of microliter plates containing 8×12 wells and sample handling by pipetting and thus represent merely an incremental operational improvement. A significant additional consideration is the need to conserve reagent and sample by reducing the spatial scale of the analytical procedures.

The present invention provides a set of operations to realize integrated sample handling and screening procedures for bead-based compound libraries in a planar format. This will significantly reduce time and cost due to reagent and sample volumes. The principal advantage of the methods of the present invention is that they provide a large set of fundamental operations to manipulate sets of beads in a planar format, permitting the handling of beads between stations in a multistep analytical procedure.

In particular, as previously described herein, the methods of the present invention facilitate the implementation of the following pertinent procedures: transfer of samples from microliter plates to a planar electrochemical cell; formation of heterogeneous panels of target sites adjacent to the substrate surface; solid phase, binding assays; and isolation of specific beads from an array. In addition, the fundamental operations of the present invention provide the means to concatenate these procedures on the surface of a planar electrode.

As described herein for hybridization assays, several variants are possible. That is, binding assays may be performed by allowing protein targets such as enzymes to bind to compounds on the surface of a bead, either in suspension or arranged in a planar array. The common practice of combinatorial chemistry based on large porous carrier beads accommodates the concurrent handling of smaller beads to whose outer surface compounds are anchored via inert chemical spacers. Such small beads (up to 10 microns in diameter) are readily manipulated by the methods of the present invention. Large beads are used as labeled compound storage containers.

Alternatively, binding between target and a radioactively or otherwise labelled probe may occur in solution, within microtiter plate wells, if compounds have already been cleaved from their synthesis support. In that case, probe-target complexes may be captured by complexation to encoded beads in each well, for example via the secondary antibody method of coupling the protein target to a bead-anchored antibody. Bead-captured probe-target complexes are then transferred to the planar cell for proximity analysis and further processing as illustrated in FIG. 10. As shown in FIG. 10, probe-target complexes 102 are allowed to form in solution. Antibody coated beads 104 are added to the solution, resulting in a bead anchored complex 106. The bead anchored complexes 106 are deposited onto electrode 108 from wells 110, and a planar array of bead anchored complexes is formed. When fluorescent probes 114 are used, these impart fluorescence to the bead anchored complex, facilitating detection.

The methods and apparatus of the present invention are well suited to the task of identifying a small number of positive events in a large set. The imaging of an entire array of probe-target complexes is further enhanced by proximity to an area detector, and by bead lensing action. The isolation of a small number of positive scores from the array is readily achieved, for example by applying optical tweezers, as described herein. The large remainder of the array may then be discarded. This in turn considerably reduces the complexity of applying more stringent tests, such as the determination of binding constants, because these may be restricted to the few retained beads. These tests may be directly applied, without the need for additional sample transfer to new containers, to the samples surviving the first screening pass.

Example IX

Hybridization Assays in Planar Array Format

The present invention can be used to implement solid phase hybridization assays in a planar array format in a configuration related to that of a protein binding assay in which target molecules are chemically attached to colloidal beads. The methods of the present invention facilitate the formation of a planar array of different target oligonucleotides for presentation to a mixture of strands in solution. Alternatively, the array may be formed subsequent to hybridization in solution to facilitate detection and analysis of the spatial distribution of fluorescence or radioactivity in the array.

Considerable research and development is presently being invested in an effort to develop miniaturized instrumentation for DNA sample extraction and preparation including amplification, transcription, labeling and fragmentation, with subsequent analysis based on hybridization assays as well as electrophoretic separation. Hybridization assays in planar array format are being developed as a diagnostic tool for the rapid detection of specific single be pair mutations in a brown segment of DNA, and for the determination of expression levels of cellular genes via analysis of the levels of corresponding mRNAs or cDNAs. Hybridization of two complementary single strands of DNA involves molecular recognition and subsequent hydrogen bond formation between corresponding nucleobases in the two opposing strands according to the rules A-T and G-C; here A, T, G and C respectively represent the four nucleobases Adenine, Thymine, Guanosine and Cytosine found in DNA; in RNA, Thymine is replaced by Uracil. The formation of double-strand, or duplex, DNA requires the pairing of two highly negatively charged strands of DNA, and the ionic strength of the buffer, along with temperature, plays a decisive role.

As previously discussed herein, two principal methods to prepare heterogeneous arrays of target strands on the surface of a planar substrate are micro-dispensing ("printing") and in-situ, spatially encoded synthesis of oligonucleotides representing all possible sequence permutations for a given total length of strand. In this context, hybridization must necessarily occur in close proximity to a planar substrate surface and this condition requires care if complications from steric hindrance and from nonspecific binding of strands to the substrate are to be avoided. Nonspecific adsorption can be a serious problem, especially in the presence of DC electric fields employed in current commercial designs that rely on electrophoretic deposition to accelerate the kinetics of hybridization on the surface. In addition, there are the technical difficulties, previously discussed herein, resulting from steric hindrance and from collective effects reflecting the crowding of probe strands near the surface.

In the context of DNA analysis, colloidal (magnetic) beads are commonly used. For example, they are employed to capture DNA in a widely used screening procedure to select cDNAs from clone libraries. Specifically, cDNAs are allowed to hybridize to sequences within long genomic DNA that is subsequently anchored to magnetic beads to extract the hybridized cDNA from the mixture.

The present invention facilitates the formation of planar arrays of oligonucleotide-decorated colloidal beads, either prior to or subsequent to hybridization of a fluorescence probe strand to the bead-anchored target strand or subsequent to hybridization in free solution and bead capture of the end-functionalized target strand. In contrast to prior art methods, the present invention does not require hybridization to occur in the vicinity of planar substrate surface, although this is an option if bead-anchored probe strands are to be delivered to substrate-anchored target strands.

The ability to perform hybridization either in solution, on the surface of individual beads, or at the substrate surface provides an unprecedented degree of flexibility. In addition, the advantages of bead arrays, as described herein, make it feasible to select and isolate individual beads, or groups of beads, from a larger array on the basis of the score in a hybridization assay. This isolation facilitates the implementation of subsequent assays on the strands of interest. The fact that beads remain mobile also means that beads of interest may be collected in designated holding areas for microsequencing, or may be moved to an area of substrate designated for PCR amplification.

The methods of the present invention may be used to implement a hybridization assay in a planar array format in one of two principal variations. All involve the presence of the entire repertoire of beads in the planar array or panel formed adjacent to the electrode surface for parallel read-out. As with heterogeneous panels in general, the arrangement of beads within the array is either random (with respect to chemical identity), and the identity of beads scoring high in the binding assay must be determined subsequently, or it is spatially encoded by invoking the "Layout-Preserving Transfer" method of sample loading described herein.

The former variant is readily implemented and accommodates array formation either prior to or subsequent to performing the binding assay. For example, binding may be performed in suspension before beads are assembled into the array. As with the aforementioned cDNA selection procedure, the method of the present invention also accommodates the use of beads as capture elements for end-functionalized target DNA, for example, via biotin-streptavidin complexation. In this latter case, beads serve as a delivery vehicle to collect all probe-target complexes to the electrode surface where they are assembled into an array for ease of analysis. In particular, proximity CCD detection of beads on electrodes will benefit from the lensing action of the beads in the array. This version of the assay is preferably used if only a small number of positive scores are expected.

Hybridization to a pre-formed bead array can take advantage of a variant of the assay which preserves spatial encoding. An array of bead clusters is formed by the "Layout-Preserving Transfer" method previously described herein, and exposed to a mixture of cDNAs. The resulting spatial distribution of fluorescence intensity or radioactivity reflects the relative abundance of cDNAs in the mixture. This procedure relies on the detection of a characteristic fluorescence or other signal from the probe-target complex on the surface of a single bead. Given the fact that the array is readily held stationary by the methods of the present invention, image acquisition may be extended to attain robust signal-to-noise for detection of low level signals. For example, a signal generated by a bead of 10 micron diameter with at most $10^8$ probe-target complexes on the surface of the bead may be detected. Bead lensing action also aids in detection.

As with the implementation of drug screening, the functional elements of the present invention may be combined to perform multiple preparative and analytical procedures on DNA.

Example X

Alignment and Stretching of DNA in Electric Field-Induced Flow

The present invention can be used to position high-molecular weight DNA in its coiled configuration by invoking the fundamental operations as they apply to other colloidal particles. However, in addition, the electrokinetic flow induced by an electric field at a patterned electrode surface may be employed to stretch out the DNA into a linear configuration in the direction of the flow.

Procedures have been recently introduced which rely on optical imaging to construct a map of cleavage sites for restriction enzymes along the contour of an elongated DNA molecule. This is generally known as a "restriction map". These procedures, which facilitate the study of the interaction of these and other proteins with DNA and may also lead to the development of techniques of DNA sequencing, depend on the ability to stretch and align DNA on a planar substrate.

For individual DNA molecules, this has been previously achieved by subjecting the molecule to elongational forces such as those exerted by fluid flow, magnetic fields acting on DNA-anchored magnetic beads or capillary forces. For example, DNA "combs" have been produced by simply placing DNA molecules into an evaporating droplet of electrolyte. If provisions are made to promote the chemical attachment of one end of the molecule to the surface, the DNA chain is stretched out as the receding line of contact between the shrinking droplet and the surface passes over the tethered molecules. This leaves behind dry DNA molecules that are attached in random positions within the substrate area initially covered by the droplet, stretched out to varying degrees and generally aligned in a pattern of radial symmetry reflecting the droplet shape. Linear "brushes", composed of a set of DNA molecules chemically tethered by one end to a common line of anchoring points, have also been previously made by aligning and stretching DNA molecules by dielectrophoresis in AC electric fields applied between two metal electrodes previously evaporated onto the substrate.

The present invention invokes electrokinetic flow adjacent to an electrode patterned by UV-mediated regrowth of oxide to provide a novel approach to the placement of DNA molecules in a predetermined arrangement on a planar electrode surface, and to the stretching of the molecules from their native coil configuration into a stretched, linear configuration that is aligned in a pre-determined direction. This process is shown in FIG. 11 and is accomplished by creating controlled gradients in the flow vicinity across the dimension of the DNA coil. The velocity gradient causes different portions of the coil to move at different velocities thereby stretching out the coil. By maintaining a stagnation point at zero velocity, the stretched coil will be fixed in position. This method has several advantages over the prior art approaches. First, DNA molecules in their coiled state are subjected to light control to form arrays of desired shape in any position on the surface. This is possible because large DNA from cosmids or YACs forms coils with a radius in the range of one micron, and thus acts in a manner analogous to colloidal heads. A set of DNA molecules may thus be steered into a desired initial arrangement. Second, UV-patterning ensures that the elongational force created by the electrokinetic flow is directed in a pre-determined direction. The presence of metal electrodes in contact with the sample, a disadvantage of the dielectrophoretic prior art method, is avoided by eliminating this source of contamination that is difficult to control especially in the presence of an electric field. On patterned Si/SiOx electrodes, flow velocities in the range of several microns/second have been generated, as required for the elongation of single DNA molecules in flow. Thus, gradients in the flow field determines both the fractional elongation and the orientation of the emerging linear configurations. Third, the present invention facilitates direct, real-time control of the velocity of the electric field-induced flow, and this in turn conveys explicit control over the fractional elongation.

While the invention has been particularly shown and described with reference to a preferred embodiment thereof, it will be understood by those skilled the art that various changes in form and details may be made therein without departing from the spirit and scope of the invention.

What is claimed is:

1. A method of making a bead array comprising: a) contacting a substrate having a planar surface with a suspension comprising populations of several differently-encoded beads having diameters of up to 10 microns, wherein each population of differently-encoded beads has a different biomolecule attached thereto and the beads comprise hydrophilic beads; and b) applying energy to said substrate or said suspension, or both, such that the populations of differently-encoded beads form an ordered array on the planar surface and the beads are at pre-determined distances from each other.

2. The method according to claim 1 wherein the biomolecule is a protein or an oligonucleotide.

3. The method according to claim 1 wherein the beads are immobilized to the substrate following step b).

4. The method according to claim 3 wherein the beads are immobilized by anchoring to the substrate.

5. The method according to claim 3 wherein the beads are immobilized by chemical attachment, heterobifunctional cross-linking agents, or physical attraction to the substrate.

6. The method according to claim 5 wherein physical attraction is through van der Waals forces.

7. The method according to claim 1 wherein the beads are in a planar crystalline arrangement.

8. The method according to claim 1 wherein the beads are in a hexagonally crystalline configuration.

9. The method according to claim 1 wherein the beads are in a bubble raft arrangement.

10. The method according to claim 1 wherein the beads are encoded using oligonucleotides.

11. The method according to claim 1 wherein the beads are binary encoded.

12. The method according to claim 1 wherein the substrate has a patterned surface.

13. The method according to claim 1 wherein the ordered array of beads comprises subarrays of beads.

14. The method according to claim 1 wherein the beads have a 2-20 micron diameter.

15. The method according to claim 1 wherein the beads range in size from approximately 100 Angstroms to 10 microns.

16. The method according to claim 1 wherein the energy is a magnetic field.

17. The method according to claim 1 wherein the energy is electrical energy.

18. The method according to claim 1 wherein the beads are magnetic.

19. The method according to claim 1 wherein the beads comprise hydrophilic beads and hydrophobic beads.

20. The method according to claim 19 wherein the beads are the same size.

21. The method according to claim 1 wherein the beads are the same size.

* * * * *